US009486472B2

(12) United States Patent
Wang et al.

(10) Patent No.: US 9,486,472 B2
(45) Date of Patent: Nov. 8, 2016

(54) METHODS FOR MODULATING NEURONAL RESPONSES

(75) Inventors: Yu Tian Wang, Vancouver (CA); Yushan Wang, Medicine Hat (CA); Anthony Phillips, Vancouver (CA); Lidong Liu, Richmond (CA); Yitao Liu, Richmond (CA)

(73) Assignee: UNIVERSITY OF BRITISH COLUMBIA CANADA, Vancouver, BC (CA)

( * ) Notice: Subject to any disclaimer, the term of this patent is extended or adjusted under 35 U.S.C. 154(b) by 1236 days.

(21) Appl. No.: 13/066,700

(22) Filed: Apr. 22, 2011

(65) Prior Publication Data

US 2012/0077751 A1  Mar. 29, 2012

Related U.S. Application Data

(63) Continuation of application No. 11/399,840, filed on Apr. 6, 2006, now abandoned, which is a continuation of application No. PCT/CA2004/001813, filed on Oct. 8, 2004.

(60) Provisional application No. 60/509,249, filed on Oct. 8, 2003.

(51) Int. Cl.
*A61K 38/00* (2006.01)
*A61K 38/08* (2006.01)
*A61K 38/10* (2006.01)
*C07K 7/06* (2006.01)
*A61K 31/7088* (2006.01)
*C07K 14/705* (2006.01)
*C12N 9/12* (2006.01)

(52) U.S. Cl.
CPC ............ *A61K 31/7088* (2013.01); *C07K 7/06* (2013.01); *C07K 14/705* (2013.01); *C12N 9/1205* (2013.01); *A61K 38/00* (2013.01); *G01N 2333/705* (2013.01); *G01N 2500/02* (2013.01); *G01N 2500/04* (2013.01)

(58) Field of Classification Search
CPC ...... A61K 38/00; A61K 38/08; A61K 38/10; C07K 14/705; C07K 7/06
USPC .............................. 514/17.7, 21.4, 21.5, 21.6
See application file for complete search history.

(56) References Cited

U.S. PATENT DOCUMENTS

| | | | |
|---|---|---|---|
| 5,731,410 A * | 3/1998 | Rogers et al. ................. | 530/325 |
| 6,383,764 B1 | 5/2002 | Civelli et al. | |
| 2004/0005579 A1 | 1/2004 | Birse et al. | |
| 2014/0038842 A1 * | 2/2014 | Tam et al. ........................ | 506/9 |

OTHER PUBLICATIONS

SEQ ID No. 300 from 2014/0038842, 2014.*

Iwakura Y, Nagano T, Kawamurat M, Horikawa H, Ibaraki K, Takei N, Nawa H, "N-Methyl-D-aspartate-induced alpha-amino-3-hydroxy-5-methyl-4-isoxazoleproprionic acid (AMPA) receptor down-regulation involves interaction of the carboxyl terminus of GluR2/3 with Pick 1," The Journal of Biological Chemistry, 2001, 276(4): 40025-40032.*
A.V. Vieira, C. Lamaze, S. L. Schmid, Science 274, 2086-2089 (1996).
Ahmed N, Nasman P, Wahlgren NG: Effect of intravenous nimodipine on blood pressure and outcome after acute stroke. Strode 31 :1250-1255, 2000.
Albers GW, Goldstein LB, Hall D, Lesko LM: Aptiganel hydrochloride in acute ischemic stroke: a randomized controlled trial. Jama 286:2673-2682, 2001.
Altschul, S.F. 1991. "Amino acid substitution matrices from an information theoretic perspective." Journal of Molecular Biology, 219: 555-665.
Arundine M, Tymianski M. Molecular mechanisms of calcium-dependent neurodegeneration in excitotoxicity. Cell Calcium. Oct.-Nov. 2003;34(4-5):325-37.
B. Marks and H. T. McMahon, Curr.Biol. 8, 740-749 (1998).
Beattie E.C. et al: "Regulation of AMPA receptor endocytosis by a signalling mechanism shared with LTD" Nature Neuroscience, vol. 3, No. 12, Dec. 2000 , pp. 129.
Becker-Hapak M, McAllister SS, Dowdy SF: TAT-mediated protein transduction into mammalian cells. Methods 24:247-256, 2001.
Benke,T.A., Luthi,A., Isaac,J.T., and Collingridge,G.L. (1998) Modulation of AMPA receptor unitary conductance by synaptic activity. Nature, 393, 793-797.
Bensimon G, Lacomblez L, Meininger V: A controlled trial of riluzole in amyotrophic lateral sclerosis. ALS/Riluzole Study Group. N Engl JMed 330:585-591, 1994.
Berke JD, Hyman SE (2000) Addiction, dopamine and the molecular mechanisms of memory. Neuron 25: 515-532.
Bonifacino,J.S. and DeH'Angelica,E.C. (1999) Molecular bases for the recognition of tyrosine-based sorting signals. J.CellBiol., 145, 923-926.
Boxall,A.R., Lancaster,B., and Garthwaite,J. (1996) Tyrosine kinase is required for long-term depression in the cerebellum. Neuron, 16, 805-813.
C. Luscher et al., Neuron 24, 649-658 (1999).
Chan S.L. et al: "Evidence for caspase-mediated cleavage of AMPA receptor subunits in neural apoptosis and Alzheimer's disease" J. Neurosci. Res., vol. 57, No. 3, Aug. 1999.
Cheramy A, Barbeito L, Godeheu G, Glowinski J: Riluzole inhibits the release of glutamate in the caudate nucleus of the cat in vivo. Neurosci Lett 147:209-212, 1992.
Colledge M. et al: "Ubiquitination regulates PSO-95 degradation and AMPA receptor surface expression"Neuron, vol. 40, No. 3, Oct. 2003 , pp. 595-607, XP00300925.
Doble A: The role of excitotoxicity in neurodegenerative disease: implications for therapy. Pharmacol Ther 81 :163-221, 1999.
Doraiswamy PM: Alzheimer's disease and the glutamate NMDA receptor. Psychopharmacol Bull 37:41-49, 2003.
E. Chalecka-Franaszek and D. M. Chuang, Proc.Natl.Acad.Sci.U. S.A 96, 8745-8750 (1999).

(Continued)

*Primary Examiner* — Julie Ha
(74) *Attorney, Agent, or Firm* — Jeffrey T. King; Patent Networks Law Group PLLC

(57) ABSTRACT

Methods and compositions for treating neurological damage or dysfunction are described, including methods implemented by administration of peptide inhibitors of AMPA receptor endocytosis.

6 Claims, 22 Drawing Sheets

(56) References Cited

OTHER PUBLICATIONS

Ellenbroek BA (2003), Animal models in the genomic era: possibilities and limitations with special emphasis on schizophrenia. Behav Pharmacol 14(5-6): 409-17.
Everitt BJ, Wolf ME (2002) Psychomotor stimulant addiction: a neural systems perspective. JNeurosci 22(9):3312-3320.
Everitt, BJ, Dickinson A, Robbins TW (2001) The neuropsychological basis of addictive behaviour. Brain Res Rev 36:129-138.
F.J. Dominique et al, Stress and glucocorticoids impair retrieval of long-term spatial memory, Nature 394:787, 1998.
Geyer MA, Ellenbroek B (2003) Animal behavior models of the mechanisms underlying antipsychotic atypicality. Prog Neuropsychopharmacol Biol Psychiatry 27(7): 1071-9.
Graham S. H. and J. Chen, J.Cereb.Blood Flow Metab 21, 99-109 (2001).
H. Dudek et al, Science 275, 661-665 (1997).
H. Y. Man et al., Neuron 25, 649-662 (2000).
H. Y. Man, W. Ju, G. Ahmadian, Y. T. Wang, Cell Mol.Life Sci. 57, 1526-1534 (2000).
Hollmann,M. and Heinemann,S. (1994) Cloned glutamate receptors. Annu.Rev.Neurosci., 17, 31-108.
Honer WG et al (2002) Abnormalities of SNARE mechanism proteins in anterior frontal cortex in severe mental illness. Cereb Cortex 12(4): 349-56.
Horn J, Limburg M: Calcium antagonists for ischemic stroke: a systematic review. Stroke 32:570-576, 2001.
Hyman SE, Malenka RC (2001) Addiction and the brain: the neurobiology of compulsion and its persistence. Nat Rev Neurosci 2:695-703.
J. W. Lin et al, Nat.Neurosci. 3, 1282-1290 (2000).
Jarousse, N. and Kelly, R.B. (2000) Selective inhibition of adaptor complex-mediated vesiculation. Traffic 1:378-384.
Johnston MV, Jeon OH, Pevsner J, Blue ME, Naidu S. Neurobiology of Rett syndrome: a genetic disorder of synapse development. Brain Dev. Dec. 2001;23 Suppl 1.S206-13.
K. L. Pierce and R. J. Lefkowitz, Nat.Rev.Neurosci. 2, 727-733 (2001).
Kabouridis, PS, Biological Applications of Protein Transduction Technology TIBS 21: 498503, 2003.
Kiselev, A. et al., Neuron 28, 139-152 (2000).
Koob GF, LeMoal M (1997) Drug abuse: Hedonic homeostatic dysregulation Science 278:52-58.
Koob GF, LeMoal M (2001) Drug addiction, dysregulation of reward, and allostasis. Neuropsychopharmacology 24:97-129.
Lau E, Bungard TJ, Tsuyuki RT: Stroke prophylaxis in institutionalized elderly patients with atrial fibrillation. J Am Geriatr Soc 52:428-433, 2004.
Lau,L.F. and Huganir,R.L. (1995) Differential tyrosine phosphorylation of N-methyl-D-aspartate receptor subunits. Journal of Biological Chemistry, 270, 20036-20041.
Lees KR: Cerestat and other NMDA antagonists in ischemic stroke. Neurology 49:S66-69, 1997.
Liang,F. and Huganir,R.L. (2001) Coupling of agonist-induced AMPA receptor internalization with receptor recycling. JNeurochem., 77, 1626-1631.
Longa EZ, Weinstein PR, Carlson S, Cummins R: Reversible middle cerebral artery occlusion without craniectomy in rats. Stroke 20: 84-91 , 1989.
Luscher,C, Nicoll,R.A., Malenka,R.C, and Muller,D. (2000) Synaptic plasticity and dynamic modulation of the postsynaptic membrane. Nat.Neurosci., 3, 545-550.
M. C. Morris, J. Depollier, J. Mery, F. Heitz, G. Divita, Nat. Biotechnol. 19, 1173-1176 (2001).
M. D. Ehlers, Neurora 28, 511-525 (2000).
M.S. Johnson and J.P. Overington. 1993. "A Structural Basis of Sequence Comparisons: An evaluation of scoring methodologies." Journal of Molecular Biology. 233: 716-738.
Malinow,R., Mainen,Z.F., and Hayashi,Y. (2000) LTP mechanisms: from silence to four-lane traffic. Curr.Opin.Neurobiol., 10, 352-357.
Mattson M. V ., Nat.Rev.Mol.Cell Biol. 1, 120-129 (2000).
Miguel-Hidalgo JJ, Alvarez XA, Cacabelos R, Quack G: Neuroprotection by memantine against neurodegeneration induced by beta-amyloid(I-40). Brain Res 958:210-221, 2002.
Mimics K et al (2000), Molecular characterization of schizophrenia viewed by microarray analysis of gene expression in prefrontal cortex. Neuron 28(1): 53-67.
P. G. Alloway, L. Howard, P. J. Dolph, Neuron 28, 129-138 (2000).
P. J. Coffer, J. Jin, J. R. Woodgett, Biochem.J. 335 ( Pt 1), 1-13 (1998).
Passafaro,M., Piech,V., and Sheng,M. (2001) Subunit-specific temporal and spatial patterns of AMPA receptor exocytosis in hippocampal neurons. Nat.Neurosci., 4, 917-926.
Pellow S, Chopin P, File SE, Briley M. Validation of opemclosed arm entries in an elevated plus-maze as a measure of anxiety in the rat. J Neurosci Methods. Aug. 1985;14(3):149.
R. Malinow and R. C. Malenka, Annu.Rev.Neurosci. 25, 103-126 (2002).
Reglodi D, Tamas A, Lengvari I: Examination of sensorimotor performance following middle cerebral artery occlusion in rats. Brain Res Bull 59:459-466, 2003.
Robinson, T.E. & Berridge, K.L. (1993). The neural basis of drug craving: an incentive-sensitization theory of addiction. Brain Res., Brain Res. Rev., 18, 247-291.
Rolling, F. Recombinant AAV-mediated gene transfer to the retina: gene therapy perspectives, Gene Ther. Oct. 2004; I Suppl S26-32.
S. H. Hansen, K. Sandvig, B. van Deurs, J.CellBiol. 121, 61-72 (1993).
S. L. Budd, L. Tenneti, T. Lishnak, S. A. Lipton, Proc.Natl.Acad.Sci. U.S.A 97, 6161-6166 (2000).
S. S. Okamoto et al., Proc.Natl.Acad.Sci. U.S.A 99, 3974-3979 (2002).
Song,L, Kamboj,S., Xia,J., Dong,H., Liao,D., and Huganir,R.L. (1998) Interaction of the N-ethylmaleimide-sensitive factor with AMPA receptors. Neuron, 21, 393-400.
Stern-Bach,Y., Russo,S., Neuman,M., and Rosenmund,C. (1998) A point mutation in the glutamate binding site blocks desensitization of AMPA receptors. Neuron, 21, 907-918.
Steven Henikoff and Jorja G. Henikoff. 1992 "Amino acid substitution matrices from protein blocks." Proc. Natl. Acad. Sci. USA. 89(biochemistry): 10915-10919.
Steven Henikoff and Jorja G. Henikoff. 1993. "Performance Evaluation of Amino Acid Substitution Matrices." Proteins: Structure, Function, and Genetics. 17: 49-61.
Thornhill J, Corbett D: Therapeutic implications of hypothermic and hyperthermic temperature conditions in stroke patients. Can JPhysiol Pharmacol 79:254-261, 2001.
Use of anti-ICAM-1 therapy in ischemic stroke: results of the Enlimomab Acute Stroke Trial. Neurology 57: 1428-1434, 2001.
Wang Y, Lim LL, Levi C, Heller RF, Fisher J: Influence of admission body temperature on stroke mortality. Stroke 31 :404-409, 2000.
Wang Y.S. et al: "Requirement for clathrin-mediated endocytosis in NMOA-induced neural apoptosis" Society for Neuroscience, No. 303.11,2002 , XP008077746.
X. Lin et al, Behavioural stress facilitates the induction of long-term depression in the hippocampus, Nature 387:497, 1997.
Y. T. Wang and D. J. Linden, Neuron 25, 635-647 (2000).
Y. T. Wang and M. W. Salter, Nature 369, 233-235 (1994).
Yen W, Williamson J, Bertram EH, Kapur J. A comparison of three NMDA receptor antagonists in the treatment of prolonged status epilepticus. Epilepsy Res. Mar. 2004;59(1):43-50.
Rudinger J, "Characteristics of the amino acids as components of a peptide hormone sequence," Peptide Hormones, J.A. Parsons Edition, University Park Press, Jun. 1976, pp. 1-7.
ISR & Written Opinion from PCT/CA2004/001813 dated Mar. 4, 2005.
Restriction Requirement for U.S. Appl. No. 11/399,840 dated Sep. 18, 2008.
Search Report for European Patent Application No. 04789721.0 dated Jun. 20, 2007.

(56) References Cited

OTHER PUBLICATIONS

Office Action for European Patent Application No. 04789721.0 dated Jun. 23, 2009.
Office Action for European Patent Application No. 04789721.0 dated May 7, 2010.
Office Action for European Patent Application No. 04789721.0 dated Sep. 28, 2011.
Office Action for European Patent Application No. 04789721.0 dated Oct. 23, 2012.
Office Action for European Patent Application No. 04789721.0 dated Apr. 10, 2014.
Office Action for European Patent Application No. 04789721.0 dated Jan. 8, 2015.
Office Action for U.S. Appl. No. 11/399,840 dated Nov. 3, 2009.
Office Action for U.S. Appl. No. 11/399,840 dated Oct. 14, 2010.

* cited by examiner

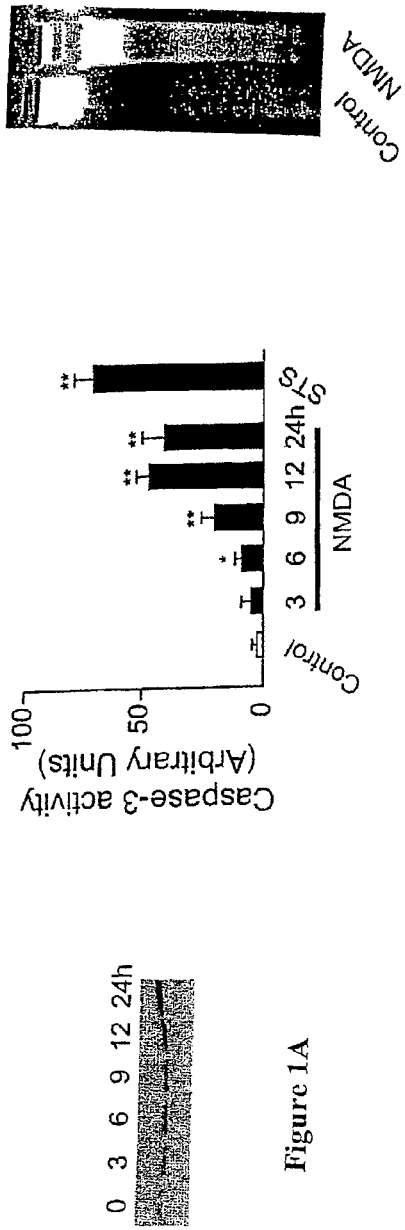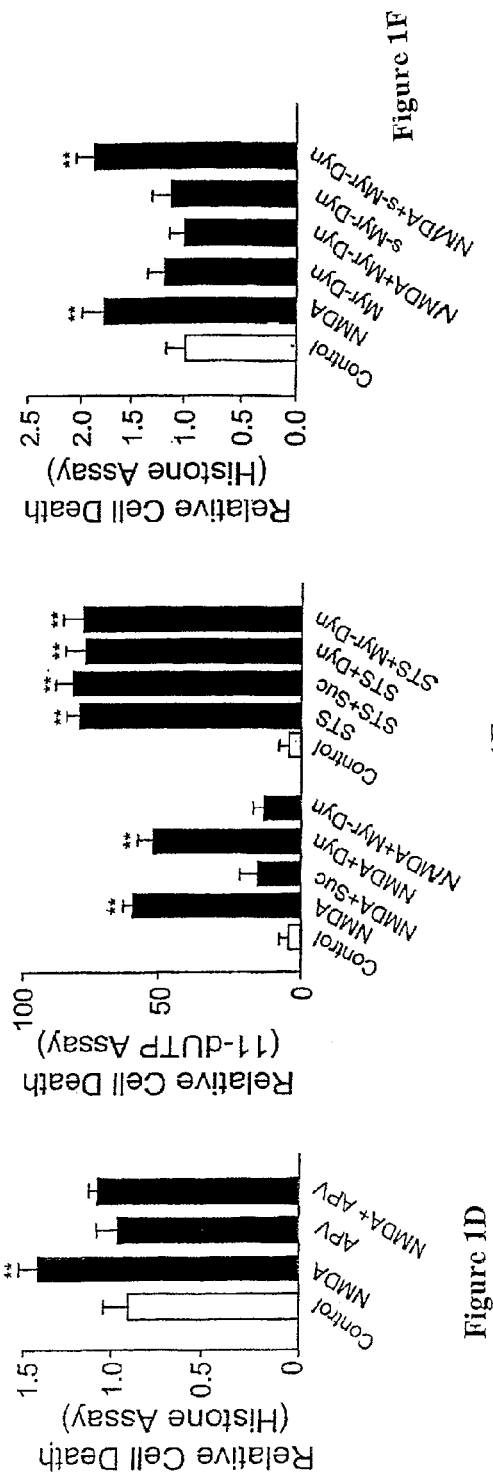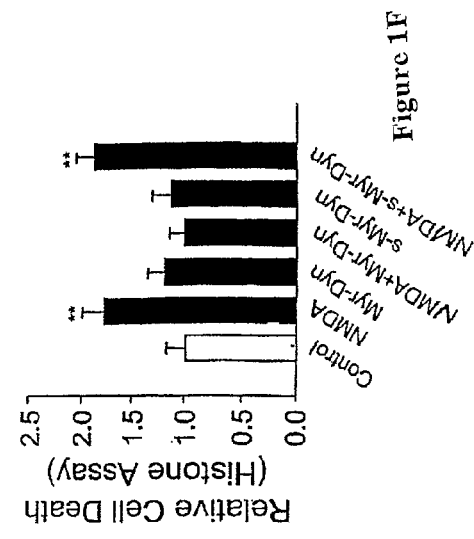

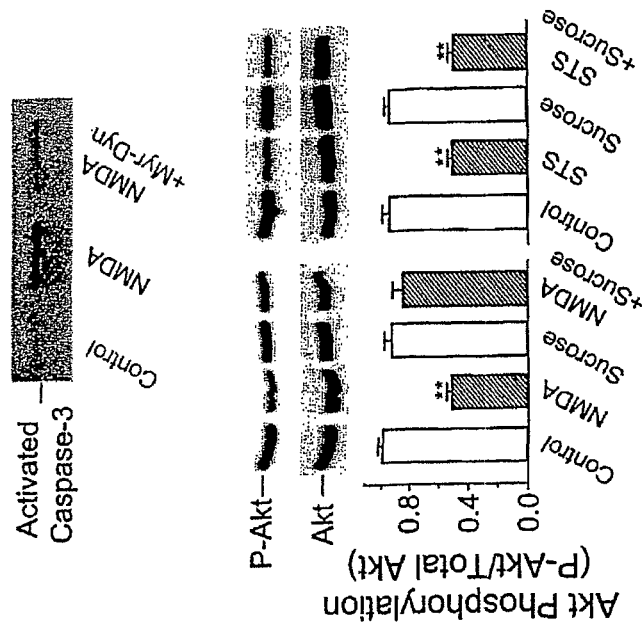
Figure 2C
Figure 2D
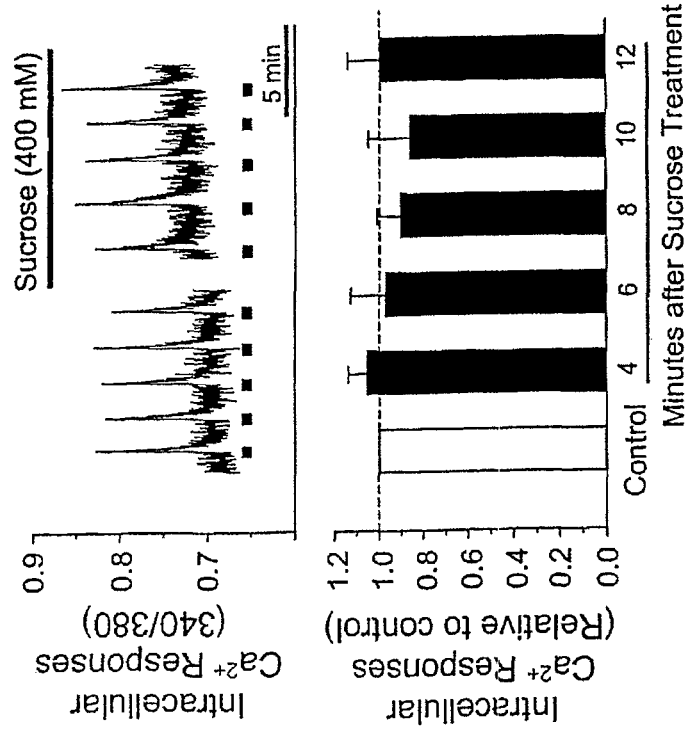
Figure 2A
Figure 2B

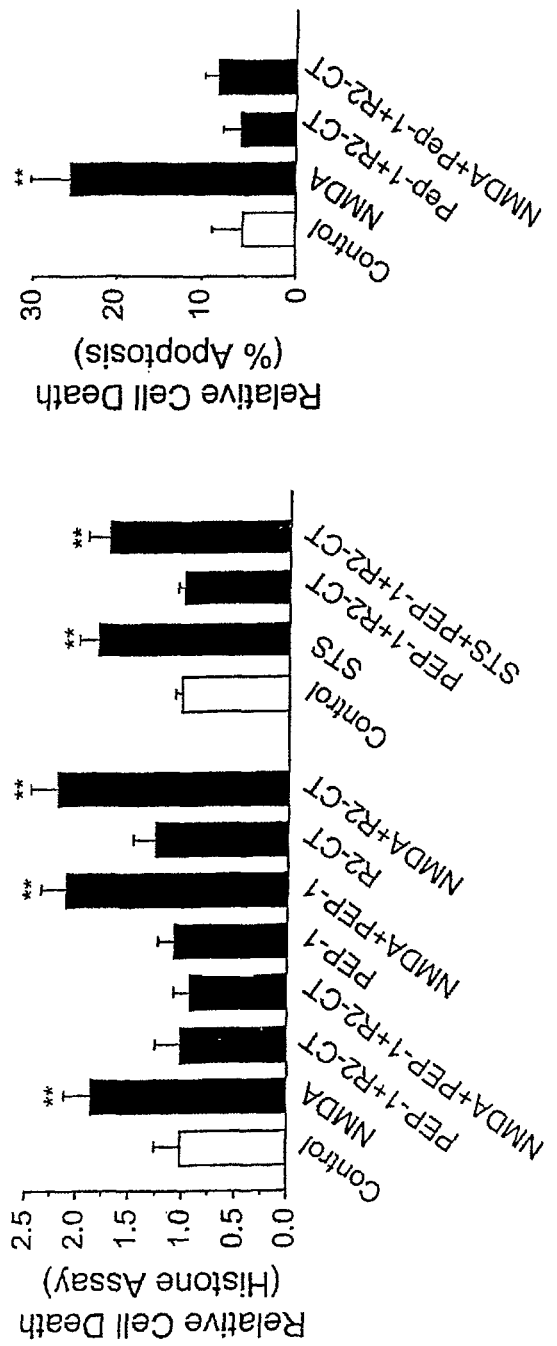

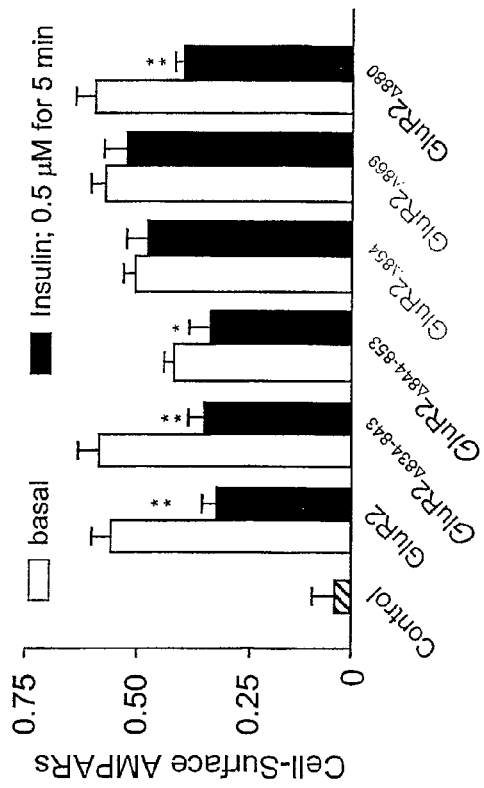
Figure 5A
Figure 5B

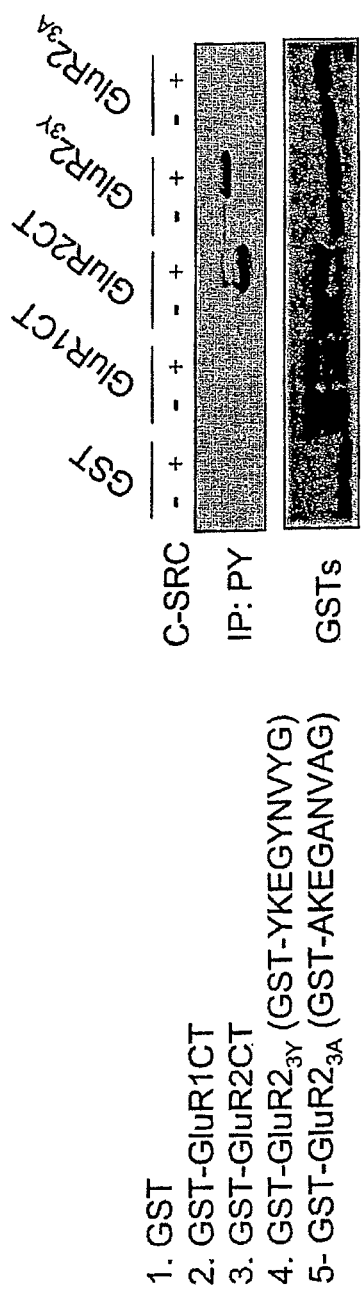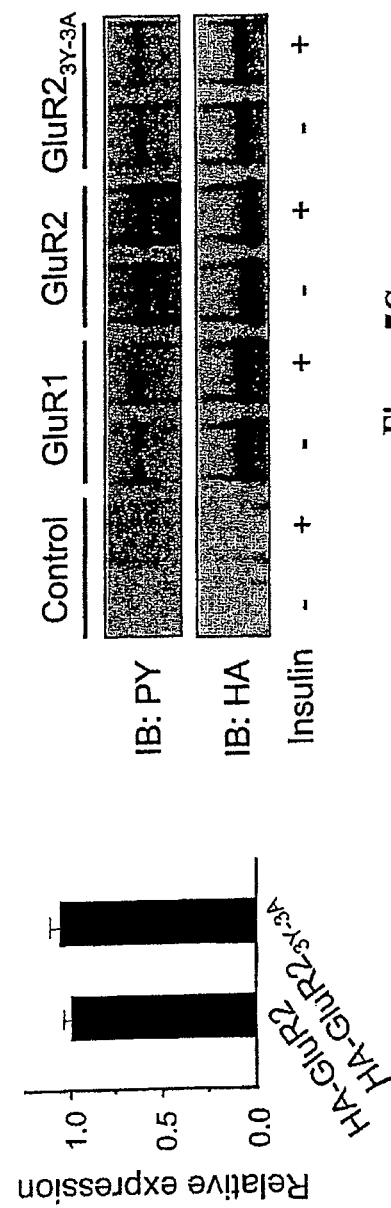
Figure 7A
Figure 7B
Figure 7C

Figure 10C
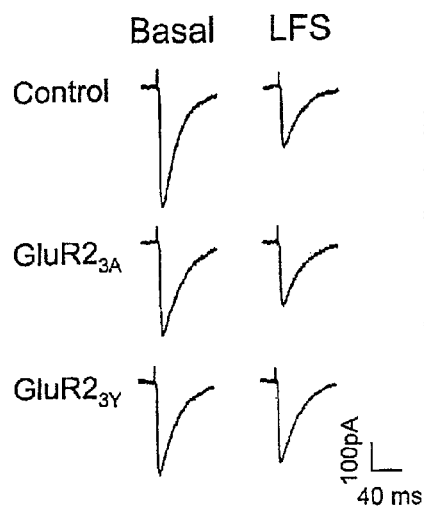
Figure 10D
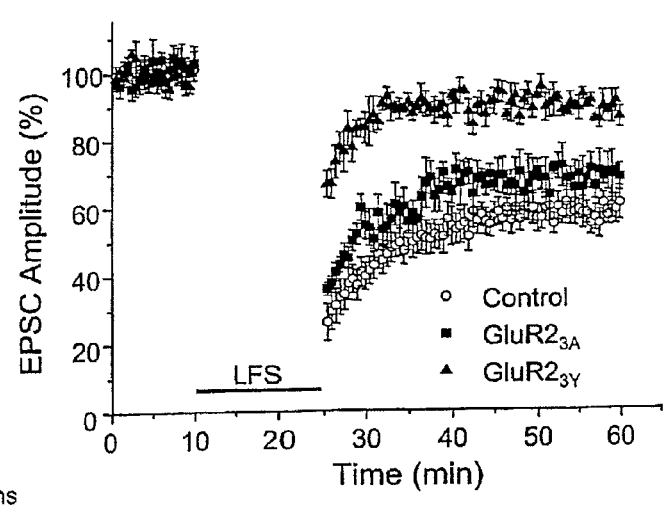
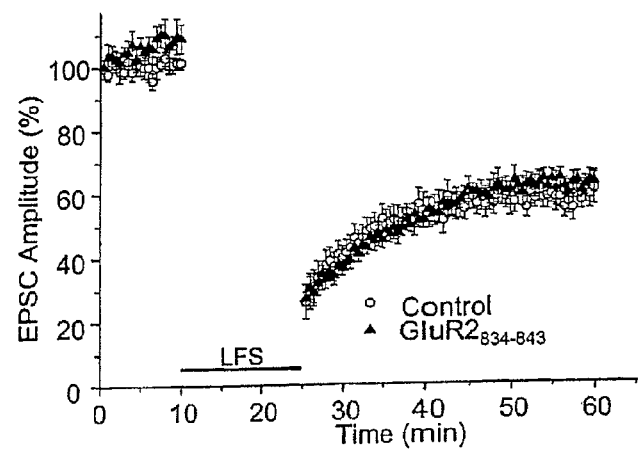
Figure 10E

Figure 12A
Figure 12B
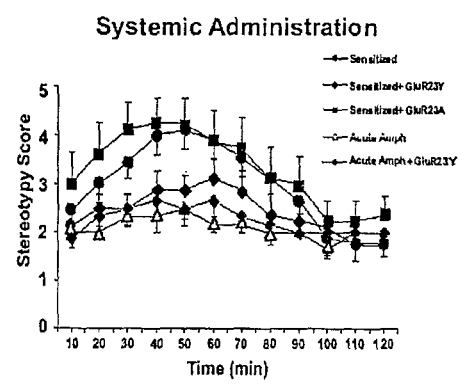
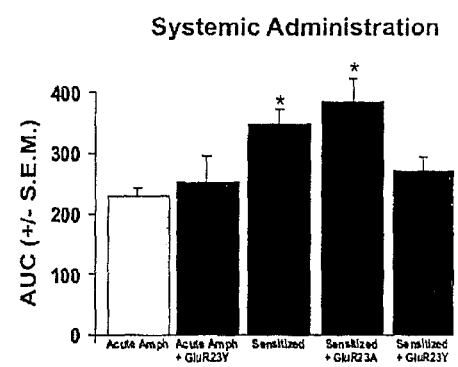
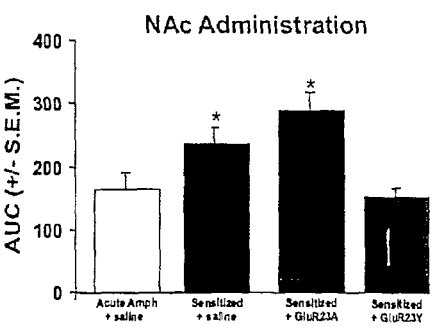
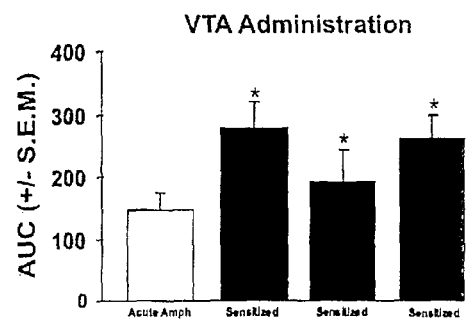
Figure 12C
Figure 12D

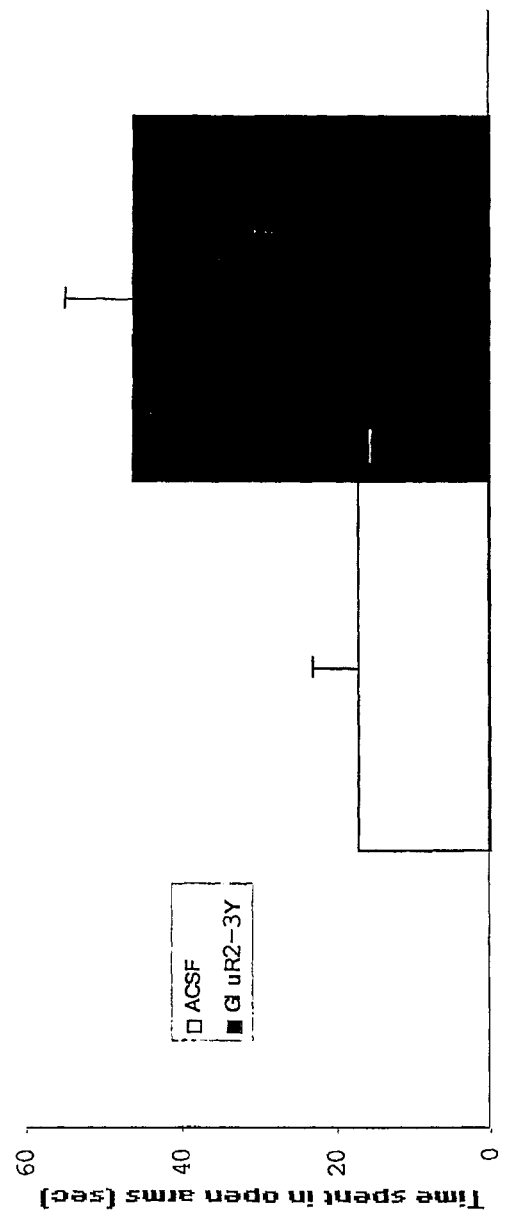

SEQUENCE LISTING

<160> NUMBER OF SEQ ID NOS: 510

<210> SEQ ID NO 1
<211> LENGTH: 11
<212> TYPE: PRT
<213> ORGANISM: Artificial
<220> FEATURE:
<223> OTHER INFORMATION: Synthetic Peptide

<400> SEQUENCE: 1

Tyr Arg Glu Gly Tyr Asn Val Tyr Gly Ile Glu
1               5                   10

<210> SEQ ID NO 2
<211> LENGTH: 11
<212> TYPE: PRT
<213> ORGANISM: Artificial
<220> FEATURE:
<223> OTHER INFORMATION: Synthetic Peptide

<400> SEQUENCE: 2

Tyr Lys Glu Gly Tyr Asn Val Tyr Gly Ile Glu
1               5                   10

<210> SEQ ID NO 3
<211> LENGTH: 9
<212> TYPE: PRT
<213> ORGANISM: Artificial
<220> FEATURE:
<223> OTHER INFORMATION: Synthetic Peptide

<400> SEQUENCE: 3

Tyr Arg Glu Gly Tyr Asn Val Tyr Gly
1               5

<210> SEQ ID NO 4
<211> LENGTH: 9
<212> TYPE: PRT
<213> ORGANISM: Artificial
<220> FEATURE:
<223> OTHER INFORMATION: Synthetic Peptide

<400> SEQUENCE: 4

Tyr Lys Glu Gly Tyr Asn Val Tyr Gly
1               5

<210> SEQ ID NO 5
<211> LENGTH: 11
<212> TYPE: PRT
<213> ORGANISM: Artificial
<220> FEATURE:
<223> OTHER INFORMATION: Synthetic Peptide

<400> SEQUENCE: 5

Tyr Gly Arg Lys Lys Arg Arg Gln Arg Arg
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic Peptide

<400> SEQUENCE: 6

Gly Ser Thr Tyr Lys Glu Gly Tyr Asn Val Tyr Gly
1               5                   10

```
<210> SEQ ID NO 7
<211> LENGTH: 12
<212> TYPE: PRT
<213> ORGANISM: Artificial
<220> FEATURE:
<223> OTHER INFORMATION: Synthetic Peptide

<400> SEQUENCE: 7

Gly Ser Thr Ala Lys Glu Gly Ala Asn Val Ala Gly
1               5                   10

<210> SEQ ID NO 8
<211> LENGTH: 9
<212> TYPE: PRT
<213> ORGANISM: Artificial
<220> FEATURE:
<223> OTHER INFORMATION: Synthetic Peptide

<400> SEQUENCE: 8

Tyr Lys Glu Gly Tyr Asn Val Asp Gly
1               5

<210> SEQ ID NO 9
<211> LENGTH: 9
<212> TYPE: PRT
<213> ORGANISM: Artificial
<220> FEATURE:
<223> OTHER INFORMATION: Synthetic Peptide

<400> SEQUENCE: 9

Tyr Lys Glu Gly Tyr Asn Val Glu Gly
1               5

<210> SEQ ID NO 10
<211> LENGTH: 9
<212> TYPE: PRT
<213> ORGANISM: Artificial
<220> FEATURE:
<223> OTHER INFORMATION: Synthetic Peptide

<400> SEQUENCE: 10

Tyr Lys Glu Gly Tyr Asn Val Ser Gly
1               5

<210> SEQ ID NO 11
<211> LENGTH: 9
<212> TYPE: PRT
<213> ORGANISM: Artificial
<220> FEATURE:
<223> OTHER INFORMATION: Synthetic Peptide

<400> SEQUENCE: 11

Tyr Lys Glu Gly Tyr Asn Val Thr Gly
1               5

<210> SEQ ID NO 12
<211> LENGTH: 9
<212> TYPE: PRT
<213> ORGANISM: Artificial
<220> FEATURE:
<223> OTHER INFORMATION: Synthetic Peptide

<400> SEQUENCE: 12

Tyr Lys Glu Gly Asp Asn Val Tyr Gly
1               5
```

<210> SEQ ID NO 13
<211> LENGTH: 9
<212> TYPE: PRT
<213> ORGANISM: Artificial
<220> FEATURE:
<223> OTHER INFORMATION: Synthetic Peptide

<400> SEQUENCE: 13

Tyr Lys Glu Gly Asp Asn Val Asp Gly
1               5

<210> SEQ ID NO 14
<211> LENGTH: 9
<212> TYPE: PRT
<213> ORGANISM: Artificial
<220> FEATURE:
<223> OTHER INFORMATION: Synthetic Peptide

<400> SEQUENCE: 14

Tyr Lys Glu Gly Asp Asn Val Glu Gly
1               5

<210> SEQ ID NO 15
<211> LENGTH: 9
<212> TYPE: PRT
<213> ORGANISM: Artificial
<220> FEATURE:
<223> OTHER INFORMATION: Synthetic Peptide

<400> SEQUENCE: 15

Tyr Lys Glu Gly Asp Asn Val Ser Gly
1               5

<210> SEQ ID NO 16
<211> LENGTH: 9
<212> TYPE: PRT
<213> ORGANISM: Artificial
<220> FEATURE:
<223> OTHER INFORMATION: Synthetic Peptide

<400> SEQUENCE: 16

Tyr Lys Glu Gly Asp Asn Val Thr Gly
1               5

<210> SEQ ID NO 17
<211> LENGTH: 9
<212> TYPE: PRT
<213> ORGANISM: Artificial
<220> FEATURE:
<223> OTHER INFORMATION: Synthetic Peptide

<400> SEQUENCE: 17

Tyr Lys Glu Gly Glu Asn Val Tyr Gly
1               5

<210> SEQ ID NO 18
<211> LENGTH: 9
<212> TYPE: PRT
<213> ORGANISM: Artificial
<220> FEATURE:
<223> OTHER INFORMATION: Synthetic Peptide

<400> SEQUENCE: 18

Tyr Lys Glu Gly Glu Asn Val Asp Gly
1               5

```
<210> SEQ ID NO 19
<211> LENGTH: 9
<212> TYPE: PRT
<213> ORGANISM: Artificial
<220> FEATURE:
<223> OTHER INFORMATION: Synthetic Peptide

<400> SEQUENCE: 19

Tyr Lys Glu Gly Glu Asn Val Glu Gly
1               5

<210> SEQ ID NO 20
<211> LENGTH: 9
<212> TYPE: PRT
<213> ORGANISM: Artificial
<220> FEATURE:
<223> OTHER INFORMATION: Synthetic Peptide

<400> SEQUENCE: 20

Tyr Lys Glu Gly Glu Asn Val Ser Gly
1               5

<210> SEQ ID NO 21
<211> LENGTH: 9
<212> TYPE: PRT
<213> ORGANISM: Artificial
<220> FEATURE:
<223> OTHER INFORMATION: Synthetic Peptide

<400> SEQUENCE: 21

Tyr Lys Glu Gly Glu Asn Val Thr Gly
1               5

<210> SEQ ID NO 22
<211> LENGTH: 9
<212> TYPE: PRT
<213> ORGANISM: Artificial
<220> FEATURE:
<223> OTHER INFORMATION: Synthetic Peptide

<400> SEQUENCE: 22

Tyr Lys Glu Gly Ser Asn Val Tyr Gly
1               5

<210> SEQ ID NO 23
<211> LENGTH: 9
<212> TYPE: PRT
<213> ORGANISM: Artificial
<220> FEATURE:
<223> OTHER INFORMATION: Synthetic Peptide

<400> SEQUENCE: 23

Tyr Lys Glu Gly Ser Asn Val Asp Gly
1               5

<210> SEQ ID NO 24
<211> LENGTH: 9
<212> TYPE: PRT
<213> ORGANISM: Artificial
<220> FEATURE:
<223> OTHER INFORMATION: Synthetic Peptide

<400> SEQUENCE: 24

Tyr Lys Glu Gly Ser Asn Val Glu Gly
1               5

<210> SEQ ID NO 25
```

```
<211> LENGTH: 9
<212> TYPE: PRT
<213> ORGANISM: Artificial
<220> FEATURE:
<223> OTHER INFORMATION: Synthetic Peptide

<400> SEQUENCE: 25

Tyr Lys Glu Gly Ser Asn Val Ser Gly
1               5

<210> SEQ ID NO 26
<211> LENGTH: 9
<212> TYPE: PRT
<213> ORGANISM: Artificial
<220> FEATURE:
<223> OTHER INFORMATION: Synthetic Peptide

<400> SEQUENCE: 26

Tyr Lys Glu Gly Ser Asn Val Thr Gly
1               5

<210> SEQ ID NO 27
<211> LENGTH: 9
<212> TYPE: PRT
<213> ORGANISM: Artificial
<220> FEATURE:
<223> OTHER INFORMATION: Synthetic Peptide

<400> SEQUENCE: 27

Tyr Lys Glu Gly Thr Asn Val Tyr Gly
1               5

<210> SEQ ID NO 28
<211> LENGTH: 9
<212> TYPE: PRT
<213> ORGANISM: Artificial
<220> FEATURE:
<223> OTHER INFORMATION: Synthetic Peptide

<400> SEQUENCE: 28

Tyr Lys Glu Gly Thr Asn Val Asp Gly
1               5

<210> SEQ ID NO 29
<211> LENGTH: 9
<212> TYPE: PRT
<213> ORGANISM: Artificial
<220> FEATURE:
<223> OTHER INFORMATION: Synthetic Peptide

<400> SEQUENCE: 29

Tyr Lys Glu Gly Thr Asn Val Glu Gly
1               5

<210> SEQ ID NO 30
<211> LENGTH: 9
<212> TYPE: PRT
<213> ORGANISM: Artificial
<220> FEATURE:
<223> OTHER INFORMATION: Synthetic Peptide

<400> SEQUENCE: 30

Tyr Lys Glu Gly Thr Asn Val Ser Gly
1               5

<210> SEQ ID NO 31
<211> LENGTH: 9
```

```
<212> TYPE: PRT
<213> ORGANISM: Artificial
<220> FEATURE:
<223> OTHER INFORMATION: Synthetic Peptide

<400> SEQUENCE: 31

Tyr Lys Glu Gly Thr Asn Val Thr Gly
1               5

<210> SEQ ID NO 32
<211> LENGTH: 9
<212> TYPE: PRT
<213> ORGANISM: Artificial
<220> FEATURE:
<223> OTHER INFORMATION: Synthetic Peptide

<400> SEQUENCE: 32

Asp Lys Glu Gly Tyr Asn Val Tyr Gly
1               5

<210> SEQ ID NO 33
<211> LENGTH: 9
<212> TYPE: PRT
<213> ORGANISM: Artificial
<220> FEATURE:
<223> OTHER INFORMATION: Synthetic Peptide

<400> SEQUENCE: 33

Asp Lys Glu Gly Tyr Asn Val Asp Gly
1               5

<210> SEQ ID NO 34
<211> LENGTH: 9
<212> TYPE: PRT
<213> ORGANISM: Artificial
<220> FEATURE:
<223> OTHER INFORMATION: Synthetic Peptide

<400> SEQUENCE: 34

Asp Lys Glu Gly Tyr Asn Val Glu Gly
1               5

<210> SEQ ID NO 35
<211> LENGTH: 9
<212> TYPE: PRT
<213> ORGANISM: Artificial
<220> FEATURE:
<223> OTHER INFORMATION: Synthetic Peptide

<400> SEQUENCE: 35

Asp Lys Glu Gly Tyr Asn Val Ser Gly
1               5

<210> SEQ ID NO 36
<211> LENGTH: 9
<212> TYPE: PRT
<213> ORGANISM: Artificial
<220> FEATURE:
<223> OTHER INFORMATION: Synthetic Peptide

<400> SEQUENCE: 36

Asp Lys Glu Gly Tyr Asn Val Thr Gly
1               5

<210> SEQ ID NO 37
<211> LENGTH: 9
<212> TYPE: PRT
```

<213> ORGANISM: Artificial
<220> FEATURE:
<223> OTHER INFORMATION: Synthetic Peptide

<400> SEQUENCE: 37

Asp Lys Glu Gly Asp Asn Val Tyr Gly
1               5

<210> SEQ ID NO 38
<211> LENGTH: 9
<212> TYPE: PRT
<213> ORGANISM: Artificial
<220> FEATURE:
<223> OTHER INFORMATION: Synthetic Peptide

<400> SEQUENCE: 38

Asp Lys Glu Gly Asp Asn Val Asp Gly
1               5

<210> SEQ ID NO 39
<211> LENGTH: 9
<212> TYPE: PRT
<213> ORGANISM: Artificial
<220> FEATURE:
<223> OTHER INFORMATION: Synthetic Peptide

<400> SEQUENCE: 39

Asp Lys Glu Gly Asp Asn Val Glu Gly
1               5

<210> SEQ ID NO 40
<211> LENGTH: 9
<212> TYPE: PRT
<213> ORGANISM: Artificial
<220> FEATURE:
<223> OTHER INFORMATION: Synthetic Peptide

<400> SEQUENCE: 40

Asp Lys Glu Gly Asp Asn Val Ser Gly
1               5

<210> SEQ ID NO 41
<211> LENGTH: 9
<212> TYPE: PRT
<213> ORGANISM: Artificial
<220> FEATURE:
<223> OTHER INFORMATION: Synthetic Peptide

<400> SEQUENCE: 41

Asp Lys Glu Gly Asp Asn Val Thr Gly
1               5

<210> SEQ ID NO 42
<211> LENGTH: 9
<212> TYPE: PRT
<213> ORGANISM: Artificial
<220> FEATURE:
<223> OTHER INFORMATION: Synthetic Peptide

<400> SEQUENCE: 42

Asp Lys Glu Gly Glu Asn Val Tyr Gly
1               5

<210> SEQ ID NO 43
<211> LENGTH: 9
<212> TYPE: PRT
<213> ORGANISM: Artificial

```
<220> FEATURE:
<223> OTHER INFORMATION: Synthetic Peptide

<400> SEQUENCE: 43

Asp Lys Glu Gly Glu Asn Val Asp Gly
1               5

<210> SEQ ID NO 44
<211> LENGTH: 9
<212> TYPE: PRT
<213> ORGANISM: Artificial
<220> FEATURE:
<223> OTHER INFORMATION: Synthetic Peptide

<400> SEQUENCE: 44

Asp Lys Glu Gly Glu Asn Val Glu Gly
1               5

<210> SEQ ID NO 45
<211> LENGTH: 9
<212> TYPE: PRT
<213> ORGANISM: Artificial
<220> FEATURE:
<223> OTHER INFORMATION: Synthetic Peptide

<400> SEQUENCE: 45

Asp Lys Glu Gly Glu Asn Val Ser Gly
1               5

<210> SEQ ID NO 46
<211> LENGTH: 9
<212> TYPE: PRT
<213> ORGANISM: Artificial
<220> FEATURE:
<223> OTHER INFORMATION: Synthetic Peptide

<400> SEQUENCE: 46

Asp Lys Glu Gly Glu Asn Val Thr Gly
1               5

<210> SEQ ID NO 47
<211> LENGTH: 9
<212> TYPE: PRT
<213> ORGANISM: Artificial
<220> FEATURE:
<223> OTHER INFORMATION: Synthetic Peptide

<400> SEQUENCE: 47

Asp Lys Glu Gly Ser Asn Val Tyr Gly
1               5

<210> SEQ ID NO 48
<211> LENGTH: 9
<212> TYPE: PRT
<213> ORGANISM: Artificial
<220> FEATURE:
<223> OTHER INFORMATION: Synthetic Peptide

<400> SEQUENCE: 48

Asp Lys Glu Gly Ser Asn Val Asp Gly
1               5

<210> SEQ ID NO 49
<211> LENGTH: 9
<212> TYPE: PRT
<213> ORGANISM: Artificial
<220> FEATURE:
```

<223> OTHER INFORMATION: Synthetic Peptide

<400> SEQUENCE: 49

Asp Lys Glu Gly Ser Asn Val Glu Gly
1               5

<210> SEQ ID NO 50
<211> LENGTH: 9
<212> TYPE: PRT
<213> ORGANISM: Artificial
<220> FEATURE:
<223> OTHER INFORMATION: Synthetic Peptide

<400> SEQUENCE: 50

Asp Lys Glu Gly Ser Asn Val Ser Gly
1               5

<210> SEQ ID NO 51
<211> LENGTH: 9
<212> TYPE: PRT
<213> ORGANISM: Artificial
<220> FEATURE:
<223> OTHER INFORMATION: Synthetic Peptide

<400> SEQUENCE: 51

Asp Lys Glu Gly Ser Asn Val Thr Gly
1               5

<210> SEQ ID NO 52
<211> LENGTH: 9
<212> TYPE: PRT
<213> ORGANISM: Artificial
<220> FEATURE:
<223> OTHER INFORMATION: Synthetic Peptide

<400> SEQUENCE: 52

Asp Lys Glu Gly Thr Asn Val Tyr Gly
1               5

<210> SEQ ID NO 53
<211> LENGTH: 9
<212> TYPE: PRT
<213> ORGANISM: Artificial
<220> FEATURE:
<223> OTHER INFORMATION: Synthetic Peptide

<400> SEQUENCE: 53

Asp Lys Glu Gly Thr Asn Val Asp Gly
1               5

<210> SEQ ID NO 54
<211> LENGTH: 9
<212> TYPE: PRT
<213> ORGANISM: Artificial
<220> FEATURE:
<223> OTHER INFORMATION: Synthetic Peptide

<400> SEQUENCE: 54

Asp Lys Glu Gly Thr Asn Val Glu Gly
1               5

<210> SEQ ID NO 55
<211> LENGTH: 9
<212> TYPE: PRT
<213> ORGANISM: Artificial
<220> FEATURE:
<223> OTHER INFORMATION: Synthetic Peptide

```
<400> SEQUENCE: 55

Asp Lys Glu Gly Thr Asn Val Ser Gly
1               5

<210> SEQ ID NO 56
<211> LENGTH: 9
<212> TYPE: PRT
<213> ORGANISM: Artificial
<220> FEATURE:
<223> OTHER INFORMATION: Synthetic Peptide

<400> SEQUENCE: 56

Asp Lys Glu Gly Thr Asn Val Thr Gly
1               5

<210> SEQ ID NO 57
<211> LENGTH: 9
<212> TYPE: PRT
<213> ORGANISM: Artificial
<220> FEATURE:
<223> OTHER INFORMATION: Synthetic Peptide

<400> SEQUENCE: 57

Glu Lys Glu Gly Tyr Asn Val Tyr Gly
1               5

<210> SEQ ID NO 58
<211> LENGTH: 9
<212> TYPE: PRT
<213> ORGANISM: Artificial
<220> FEATURE:
<223> OTHER INFORMATION: Synthetic Peptide

<400> SEQUENCE: 58

Glu Lys Glu Gly Tyr Asn Val Asp Gly
1               5

<210> SEQ ID NO 59
<211> LENGTH: 9
<212> TYPE: PRT
<213> ORGANISM: Artificial
<220> FEATURE:
<223> OTHER INFORMATION: Synthetic Peptide

<400> SEQUENCE: 59

Glu Lys Glu Gly Tyr Asn Val Glu Gly
1               5

<210> SEQ ID NO 60
<211> LENGTH: 9
<212> TYPE: PRT
<213> ORGANISM: Artificial
<220> FEATURE:
<223> OTHER INFORMATION: Synthetic Peptide

<400> SEQUENCE: 60

Glu Lys Glu Gly Tyr Asn Val Ser Gly
1               5

<210> SEQ ID NO 61
<211> LENGTH: 9
<212> TYPE: PRT
<213> ORGANISM: Artificial
<220> FEATURE:
<223> OTHER INFORMATION: Synthetic Peptide
```

<400> SEQUENCE: 61

Glu Lys Glu Gly Tyr Asn Val Thr Gly
1               5

<210> SEQ ID NO 62
<211> LENGTH: 9
<212> TYPE: PRT
<213> ORGANISM: Artificial
<220> FEATURE:
<223> OTHER INFORMATION: Synthetic Peptide

<400> SEQUENCE: 62

Glu Lys Glu Gly Asp Asn Val Tyr Gly
1               5

<210> SEQ ID NO 63
<211> LENGTH: 9
<212> TYPE: PRT
<213> ORGANISM: Artificial
<220> FEATURE:
<223> OTHER INFORMATION: Synthetic Peptide

<400> SEQUENCE: 63

Glu Lys Glu Gly Asp Asn Val Asp Gly
1               5

<210> SEQ ID NO 64
<211> LENGTH: 9
<212> TYPE: PRT
<213> ORGANISM: Artificial
<220> FEATURE:
<223> OTHER INFORMATION: Synthetic Peptide

<400> SEQUENCE: 64

Glu Lys Glu Gly Asp Asn Val Glu Gly
1               5

<210> SEQ ID NO 65
<211> LENGTH: 9
<212> TYPE: PRT
<213> ORGANISM: Artificial
<220> FEATURE:
<223> OTHER INFORMATION: Synthetic Peptide

<400> SEQUENCE: 65

Glu Lys Glu Gly Asp Asn Val Ser Gly
1               5

<210> SEQ ID NO 66
<211> LENGTH: 9
<212> TYPE: PRT
<213> ORGANISM: Artificial
<220> FEATURE:
<223> OTHER INFORMATION: Synthetic Peptide

<400> SEQUENCE: 66

Glu Lys Glu Gly Asp Asn Val Thr Gly
1               5

<210> SEQ ID NO 67
<211> LENGTH: 9
<212> TYPE: PRT
<213> ORGANISM: Artificial
<220> FEATURE:
<223> OTHER INFORMATION: Synthetic Peptide

<400> SEQUENCE: 67

```
Glu Lys Glu Gly Glu Asn Val Tyr Gly
1               5

<210> SEQ ID NO 68
<211> LENGTH: 9
<212> TYPE: PRT
<213> ORGANISM: Artificial
<220> FEATURE:
<223> OTHER INFORMATION: Synthetic Peptide

<400> SEQUENCE: 68

Glu Lys Glu Gly Glu Asn Val Asp Gly
1               5

<210> SEQ ID NO 69
<211> LENGTH: 9
<212> TYPE: PRT
<213> ORGANISM: Artificial
<220> FEATURE:
<223> OTHER INFORMATION: Synthetic Peptide

<400> SEQUENCE: 69

Glu Lys Glu Gly Glu Asn Val Glu Gly
1               5

<210> SEQ ID NO 70
<211> LENGTH: 9
<212> TYPE: PRT
<213> ORGANISM: Artificial
<220> FEATURE:
<223> OTHER INFORMATION: Synthetic Peptide

<400> SEQUENCE: 70

Glu Lys Glu Gly Glu Asn Val Ser Gly
1               5

<210> SEQ ID NO 71
<211> LENGTH: 9
<212> TYPE: PRT
<213> ORGANISM: Artificial
<220> FEATURE:
<223> OTHER INFORMATION: Synthetic Peptide

<400> SEQUENCE: 71

Glu Lys Glu Gly Glu Asn Val Thr Gly
1               5

<210> SEQ ID NO 72
<211> LENGTH: 9
<212> TYPE: PRT
<213> ORGANISM: Artificial
<220> FEATURE:
<223> OTHER INFORMATION: Synthetic Peptide

<400> SEQUENCE: 72

Glu Lys Glu Gly Ser Asn Val Tyr Gly
1               5

<210> SEQ ID NO 73
<211> LENGTH: 9
<212> TYPE: PRT
<213> ORGANISM: Artificial
<220> FEATURE:
<223> OTHER INFORMATION: Synthetic Peptide

<400> SEQUENCE: 73
```

```
Glu Lys Glu Gly Ser Asn Val Asp Gly
1               5

<210> SEQ ID NO 74
<211> LENGTH: 9
<212> TYPE: PRT
<213> ORGANISM: Artificial
<220> FEATURE:
<223> OTHER INFORMATION: Synthetic Peptide

<400> SEQUENCE: 74

Glu Lys Glu Gly Ser Asn Val Glu Gly
1               5

<210> SEQ ID NO 75
<211> LENGTH: 9
<212> TYPE: PRT
<213> ORGANISM: Artificial
<220> FEATURE:
<223> OTHER INFORMATION: Synthetic Peptide

<400> SEQUENCE: 75

Glu Lys Glu Gly Ser Asn Val Ser Gly
1               5

<210> SEQ ID NO 76
<211> LENGTH: 9
<212> TYPE: PRT
<213> ORGANISM: Artificial
<220> FEATURE:
<223> OTHER INFORMATION: Synthetic Peptide

<400> SEQUENCE: 76

Glu Lys Glu Gly Ser Asn Val Thr Gly
1               5

<210> SEQ ID NO 77
<211> LENGTH: 9
<212> TYPE: PRT
<213> ORGANISM: Artificial
<220> FEATURE:
<223> OTHER INFORMATION: Synthetic Peptide

<400> SEQUENCE: 77

Glu Lys Glu Gly Thr Asn Val Tyr Gly
1               5

<210> SEQ ID NO 78
<211> LENGTH: 9
<212> TYPE: PRT
<213> ORGANISM: Artificial
<220> FEATURE:
<223> OTHER INFORMATION: Synthetic Peptide

<400> SEQUENCE: 78

Glu Lys Glu Gly Thr Asn Val Asp Gly
1               5

<210> SEQ ID NO 79
<211> LENGTH: 9
<212> TYPE: PRT
<213> ORGANISM: Artificial
<220> FEATURE:
<223> OTHER INFORMATION: Synthetic Peptide

<400> SEQUENCE: 79

Glu Lys Glu Gly Thr Asn Val Glu Gly
```

```
1               5
```

<210> SEQ ID NO 80
<211> LENGTH: 9
<212> TYPE: PRT
<213> ORGANISM: Artificial
<220> FEATURE:
<223> OTHER INFORMATION: Synthetic Peptide

<400> SEQUENCE: 80

```
Glu Lys Glu Gly Thr Asn Val Ser Gly
1               5
```

<210> SEQ ID NO 81
<211> LENGTH: 9
<212> TYPE: PRT
<213> ORGANISM: Artificial
<220> FEATURE:
<223> OTHER INFORMATION: Synthetic Peptide

<400> SEQUENCE: 81

```
Glu Lys Glu Gly Thr Asn Val Thr Gly
1               5
```

<210> SEQ ID NO 82
<211> LENGTH: 9
<212> TYPE: PRT
<213> ORGANISM: Artificial
<220> FEATURE:
<223> OTHER INFORMATION: Synthetic Peptide

<400> SEQUENCE: 82

```
Ser Lys Glu Gly Tyr Asn Val Tyr Gly
1               5
```

<210> SEQ ID NO 83
<211> LENGTH: 9
<212> TYPE: PRT
<213> ORGANISM: Artificial
<220> FEATURE:
<223> OTHER INFORMATION: Synthetic Peptide

<400> SEQUENCE: 83

```
Ser Lys Glu Gly Tyr Asn Val Asp Gly
1               5
```

<210> SEQ ID NO 84
<211> LENGTH: 9
<212> TYPE: PRT
<213> ORGANISM: Artificial
<220> FEATURE:
<223> OTHER INFORMATION: Synthetic Peptide

<400> SEQUENCE: 84

```
Ser Lys Glu Gly Tyr Asn Val Glu Gly
1               5
```

<210> SEQ ID NO 85
<211> LENGTH: 9
<212> TYPE: PRT
<213> ORGANISM: Artificial
<220> FEATURE:
<223> OTHER INFORMATION: Synthetic Peptide

<400> SEQUENCE: 85

```
Ser Lys Glu Gly Tyr Asn Val Ser Gly
1               5
```

<210> SEQ ID NO 86
<211> LENGTH: 9
<212> TYPE: PRT
<213> ORGANISM: Artificial
<220> FEATURE:
<223> OTHER INFORMATION: Synthetic Peptide

<400> SEQUENCE: 86

Ser Lys Glu Gly Tyr Asn Val Thr Gly
1               5

<210> SEQ ID NO 87
<211> LENGTH: 9
<212> TYPE: PRT
<213> ORGANISM: Artificial
<220> FEATURE:
<223> OTHER INFORMATION: Synthetic Peptide

<400> SEQUENCE: 87

Ser Lys Glu Gly Asp Asn Val Tyr Gly
1               5

<210> SEQ ID NO 88
<211> LENGTH: 9
<212> TYPE: PRT
<213> ORGANISM: Artificial
<220> FEATURE:
<223> OTHER INFORMATION: Synthetic Peptide

<400> SEQUENCE: 88

Ser Lys Glu Gly Asp Asn Val Asp Gly
1               5

<210> SEQ ID NO 89
<211> LENGTH: 9
<212> TYPE: PRT
<213> ORGANISM: Artificial
<220> FEATURE:
<223> OTHER INFORMATION: Synthetic Peptide

<400> SEQUENCE: 89

Ser Lys Glu Gly Asp Asn Val Glu Gly
1               5

<210> SEQ ID NO 90
<211> LENGTH: 9
<212> TYPE: PRT
<213> ORGANISM: Artificial
<220> FEATURE:
<223> OTHER INFORMATION: Synthetic Peptide

<400> SEQUENCE: 90

Ser Lys Glu Gly Asp Asn Val Ser Gly
1               5

<210> SEQ ID NO 91
<211> LENGTH: 9
<212> TYPE: PRT
<213> ORGANISM: Artificial
<220> FEATURE:
<223> OTHER INFORMATION: Synthetic Peptide

<400> SEQUENCE: 91

Ser Lys Glu Gly Asp Asn Val Thr Gly
1               5

```
<210> SEQ ID NO 92
<211> LENGTH: 9
<212> TYPE: PRT
<213> ORGANISM: Artificial
<220> FEATURE:
<223> OTHER INFORMATION: Synthetic Peptide

<400> SEQUENCE: 92

Ser Lys Glu Gly Glu Asn Val Tyr Gly
1               5

<210> SEQ ID NO 93
<211> LENGTH: 9
<212> TYPE: PRT
<213> ORGANISM: Artificial
<220> FEATURE:
<223> OTHER INFORMATION: Synthetic Peptide

<400> SEQUENCE: 93

Ser Lys Glu Gly Glu Asn Val Asp Gly
1               5

<210> SEQ ID NO 94
<211> LENGTH: 9
<212> TYPE: PRT
<213> ORGANISM: Artificial
<220> FEATURE:
<223> OTHER INFORMATION: Synthetic Peptide

<400> SEQUENCE: 94

Ser Lys Glu Gly Glu Asn Val Glu Gly
1               5

<210> SEQ ID NO 95
<211> LENGTH: 9
<212> TYPE: PRT
<213> ORGANISM: Artificial
<220> FEATURE:
<223> OTHER INFORMATION: Synthetic Peptide

<400> SEQUENCE: 95

Ser Lys Glu Gly Glu Asn Val Ser Gly
1               5

<210> SEQ ID NO 96
<211> LENGTH: 9
<212> TYPE: PRT
<213> ORGANISM: Artificial
<220> FEATURE:
<223> OTHER INFORMATION: Synthetic Peptide

<400> SEQUENCE: 96

Ser Lys Glu Gly Glu Asn Val Thr Gly
1               5

<210> SEQ ID NO 97
<211> LENGTH: 9
<212> TYPE: PRT
<213> ORGANISM: Artificial
<220> FEATURE:
<223> OTHER INFORMATION: Synthetic Peptide

<400> SEQUENCE: 97

Ser Lys Glu Gly Ser Asn Val Tyr Gly
1               5
```

```
<210> SEQ ID NO 98
<211> LENGTH: 9
<212> TYPE: PRT
<213> ORGANISM: Artificial
<220> FEATURE:
<223> OTHER INFORMATION: Synthetic Peptide

<400> SEQUENCE: 98

Ser Lys Glu Gly Ser Asn Val Asp Gly
1               5

<210> SEQ ID NO 99
<211> LENGTH: 9
<212> TYPE: PRT
<213> ORGANISM: Artificial
<220> FEATURE:
<223> OTHER INFORMATION: Synthetic Peptide

<400> SEQUENCE: 99

Ser Lys Glu Gly Ser Asn Val Glu Gly
1               5

<210> SEQ ID NO 100
<211> LENGTH: 9
<212> TYPE: PRT
<213> ORGANISM: Artificial
<220> FEATURE:
<223> OTHER INFORMATION: Synthetic Peptide

<400> SEQUENCE: 100

Ser Lys Glu Gly Ser Asn Val Ser Gly
1               5

<210> SEQ ID NO 101
<211> LENGTH: 9
<212> TYPE: PRT
<213> ORGANISM: Artificial
<220> FEATURE:
<223> OTHER INFORMATION: Synthetic Peptide

<400> SEQUENCE: 101

Ser Lys Glu Gly Ser Asn Val Thr Gly
1               5

<210> SEQ ID NO 102
<211> LENGTH: 9
<212> TYPE: PRT
<213> ORGANISM: Artificial
<220> FEATURE:
<223> OTHER INFORMATION: Synthetic Peptide

<400> SEQUENCE: 102

Ser Lys Glu Gly Thr Asn Val Tyr Gly
1               5

<210> SEQ ID NO 103
<211> LENGTH: 9
<212> TYPE: PRT
<213> ORGANISM: Artificial
<220> FEATURE:
<223> OTHER INFORMATION: Synthetic Peptide

<400> SEQUENCE: 103

Ser Lys Glu Gly Thr Asn Val Asp Gly
1               5

<210> SEQ ID NO 104
```

```
<211> LENGTH: 9
<212> TYPE: PRT
<213> ORGANISM: Artificial
<220> FEATURE:
<223> OTHER INFORMATION: Synthetic Peptide

<400> SEQUENCE: 104

Ser Lys Glu Gly Thr Asn Val Glu Gly
1               5

<210> SEQ ID NO 105
<211> LENGTH: 9
<212> TYPE: PRT
<213> ORGANISM: Artificial
<220> FEATURE:
<223> OTHER INFORMATION: Synthetic Peptide

<400> SEQUENCE: 105

Ser Lys Glu Gly Thr Asn Val Ser Gly
1               5

<210> SEQ ID NO 106
<211> LENGTH: 9
<212> TYPE: PRT
<213> ORGANISM: Artificial
<220> FEATURE:
<223> OTHER INFORMATION: Synthetic Peptide

<400> SEQUENCE: 106

Ser Lys Glu Gly Thr Asn Val Thr Gly
1               5

<210> SEQ ID NO 107
<211> LENGTH: 9
<212> TYPE: PRT
<213> ORGANISM: Artificial
<220> FEATURE:
<223> OTHER INFORMATION: Synthetic Peptide

<400> SEQUENCE: 107

Thr Lys Glu Gly Tyr Asn Val Tyr Gly
1               5

<210> SEQ ID NO 108
<211> LENGTH: 9
<212> TYPE: PRT
<213> ORGANISM: Artificial
<220> FEATURE:
<223> OTHER INFORMATION: Synthetic Peptide

<400> SEQUENCE: 108

Thr Lys Glu Gly Tyr Asn Val Asp Gly
1               5

<210> SEQ ID NO 109
<211> LENGTH: 9
<212> TYPE: PRT
<213> ORGANISM: Artificial
<220> FEATURE:
<223> OTHER INFORMATION: Synthetic Peptide

<400> SEQUENCE: 109

Thr Lys Glu Gly Tyr Asn Val Glu Gly
1               5

<210> SEQ ID NO 110
<211> LENGTH: 9
```

```
<212> TYPE: PRT
<213> ORGANISM: Artificial
<220> FEATURE:
<223> OTHER INFORMATION: Synthetic Peptide

<400> SEQUENCE: 110

Thr Lys Glu Gly Tyr Asn Val Ser Gly
1               5

<210> SEQ ID NO 111
<211> LENGTH: 9
<212> TYPE: PRT
<213> ORGANISM: Artificial
<220> FEATURE:
<223> OTHER INFORMATION: Synthetic Peptide

<400> SEQUENCE: 111

Thr Lys Glu Gly Tyr Asn Val Thr Gly
1               5

<210> SEQ ID NO 112
<211> LENGTH: 9
<212> TYPE: PRT
<213> ORGANISM: Artificial
<220> FEATURE:
<223> OTHER INFORMATION: Synthetic Peptide

<400> SEQUENCE: 112

Thr Lys Glu Gly Asp Asn Val Tyr Gly
1               5

<210> SEQ ID NO 113
<211> LENGTH: 9
<212> TYPE: PRT
<213> ORGANISM: Artificial
<220> FEATURE:
<223> OTHER INFORMATION: Synthetic Peptide

<400> SEQUENCE: 113

Thr Lys Glu Gly Asp Asn Val Asp Gly
1               5

<210> SEQ ID NO 114
<211> LENGTH: 9
<212> TYPE: PRT
<213> ORGANISM: Artificial
<220> FEATURE:
<223> OTHER INFORMATION: Synthetic Peptide

<400> SEQUENCE: 114

Thr Lys Glu Gly Asp Asn Val Glu Gly
1               5

<210> SEQ ID NO 115
<211> LENGTH: 9
<212> TYPE: PRT
<213> ORGANISM: Artificial
<220> FEATURE:
<223> OTHER INFORMATION: Synthetic Peptide

<400> SEQUENCE: 115

Thr Lys Glu Gly Asp Asn Val Ser Gly
1               5

<210> SEQ ID NO 116
<211> LENGTH: 9
<212> TYPE: PRT
```

```
<213> ORGANISM: Artificial
<220> FEATURE:
<223> OTHER INFORMATION: Synthetic Peptide

<400> SEQUENCE: 116

Thr Lys Glu Gly Asp Asn Val Thr Gly
1               5

<210> SEQ ID NO 117
<211> LENGTH: 9
<212> TYPE: PRT
<213> ORGANISM: Artificial
<220> FEATURE:
<223> OTHER INFORMATION: Synthetic Peptide

<400> SEQUENCE: 117

Thr Lys Glu Gly Glu Asn Val Tyr Gly
1               5

<210> SEQ ID NO 118
<211> LENGTH: 9
<212> TYPE: PRT
<213> ORGANISM: Artificial
<220> FEATURE:
<223> OTHER INFORMATION: Synthetic Peptide

<400> SEQUENCE: 118

Thr Lys Glu Gly Glu Asn Val Asp Gly
1               5

<210> SEQ ID NO 119
<211> LENGTH: 9
<212> TYPE: PRT
<213> ORGANISM: Artificial
<220> FEATURE:
<223> OTHER INFORMATION: Synthetic Peptide

<400> SEQUENCE: 119

Thr Lys Glu Gly Glu Asn Val Glu Gly
1               5

<210> SEQ ID NO 120
<211> LENGTH: 9
<212> TYPE: PRT
<213> ORGANISM: Artificial
<220> FEATURE:
<223> OTHER INFORMATION: Synthetic Peptide

<400> SEQUENCE: 120

Thr Lys Glu Gly Glu Asn Val Ser Gly
1               5

<210> SEQ ID NO 121
<211> LENGTH: 9
<212> TYPE: PRT
<213> ORGANISM: Artificial
<220> FEATURE:
<223> OTHER INFORMATION: Synthetic Peptide

<400> SEQUENCE: 121

Thr Lys Glu Gly Glu Asn Val Thr Gly
1               5

<210> SEQ ID NO 122
<211> LENGTH: 9
<212> TYPE: PRT
<213> ORGANISM: Artificial
```

```
<220> FEATURE:
<223> OTHER INFORMATION: Synthetic Peptide

<400> SEQUENCE: 122

Thr Lys Glu Gly Ser Asn Val Tyr Gly
1               5

<210> SEQ ID NO 123
<211> LENGTH: 9
<212> TYPE: PRT
<213> ORGANISM: Artificial
<220> FEATURE:
<223> OTHER INFORMATION: Synthetic Peptide

<400> SEQUENCE: 123

Thr Lys Glu Gly Ser Asn Val Asp Gly
1               5

<210> SEQ ID NO 124
<211> LENGTH: 9
<212> TYPE: PRT
<213> ORGANISM: Artificial
<220> FEATURE:
<223> OTHER INFORMATION: Synthetic Peptide

<400> SEQUENCE: 124

Thr Lys Glu Gly Ser Asn Val Glu Gly
1               5

<210> SEQ ID NO 125
<211> LENGTH: 9
<212> TYPE: PRT
<213> ORGANISM: Artificial
<220> FEATURE:
<223> OTHER INFORMATION: Synthetic Peptide

<400> SEQUENCE: 125

Thr Lys Glu Gly Ser Asn Val Ser Gly
1               5

<210> SEQ ID NO 126
<211> LENGTH: 9
<212> TYPE: PRT
<213> ORGANISM: Artificial
<220> FEATURE:
<223> OTHER INFORMATION: Synthetic Peptide

<400> SEQUENCE: 126

Thr Lys Glu Gly Ser Asn Val Thr Gly
1               5

<210> SEQ ID NO 127
<211> LENGTH: 9
<212> TYPE: PRT
<213> ORGANISM: Artificial
<220> FEATURE:
<223> OTHER INFORMATION: Synthetic Peptide

<400> SEQUENCE: 127

Thr Lys Glu Gly Thr Asn Val Tyr Gly
1               5

<210> SEQ ID NO 128
<211> LENGTH: 9
<212> TYPE: PRT
<213> ORGANISM: Artificial
<220> FEATURE:
```

<223> OTHER INFORMATION: Synthetic Peptide

<400> SEQUENCE: 128

Thr Lys Glu Gly Thr Asn Val Asp Gly
1               5

<210> SEQ ID NO 129
<211> LENGTH: 9
<212> TYPE: PRT
<213> ORGANISM: Artificial
<220> FEATURE:
<223> OTHER INFORMATION: Synthetic Peptide

<400> SEQUENCE: 129

Thr Lys Glu Gly Thr Asn Val Glu Gly
1               5

<210> SEQ ID NO 130
<211> LENGTH: 9
<212> TYPE: PRT
<213> ORGANISM: Artificial
<220> FEATURE:
<223> OTHER INFORMATION: Synthetic Peptide

<400> SEQUENCE: 130

Thr Lys Glu Gly Thr Asn Val Ser Gly
1               5

<210> SEQ ID NO 131
<211> LENGTH: 9
<212> TYPE: PRT
<213> ORGANISM: Artificial
<220> FEATURE:
<223> OTHER INFORMATION: Synthetic Peptide

<400> SEQUENCE: 131

Thr Lys Glu Gly Thr Asn Val Thr Gly
1               5

<210> SEQ ID NO 132
<211> LENGTH: 9
<212> TYPE: PRT
<213> ORGANISM: Artificial
<220> FEATURE:
<223> OTHER INFORMATION: Synthetic Peptide

<400> SEQUENCE: 132

Tyr Arg Glu Gly Tyr Asn Val Asp Gly
1               5

<210> SEQ ID NO 133
<211> LENGTH: 9
<212> TYPE: PRT
<213> ORGANISM: Artificial
<220> FEATURE:
<223> OTHER INFORMATION: Synthetic Peptide

<400> SEQUENCE: 133

Tyr Arg Glu Gly Tyr Asn Val Glu Gly
1               5

<210> SEQ ID NO 134
<211> LENGTH: 9
<212> TYPE: PRT
<213> ORGANISM: Artificial
<220> FEATURE:
<223> OTHER INFORMATION: Synthetic Peptide

<400> SEQUENCE: 134

Tyr Arg Glu Gly Tyr Asn Val Ser Gly
1               5

<210> SEQ ID NO 135
<211> LENGTH: 9
<212> TYPE: PRT
<213> ORGANISM: Artificial
<220> FEATURE:
<223> OTHER INFORMATION: Synthetic Peptide

<400> SEQUENCE: 135

Tyr Arg Glu Gly Tyr Asn Val Thr Gly
1               5

<210> SEQ ID NO 136
<211> LENGTH: 9
<212> TYPE: PRT
<213> ORGANISM: Artificial
<220> FEATURE:
<223> OTHER INFORMATION: Synthetic Peptide

<400> SEQUENCE: 136

Tyr Arg Glu Gly Asp Asn Val Tyr Gly
1               5

<210> SEQ ID NO 137
<211> LENGTH: 9
<212> TYPE: PRT
<213> ORGANISM: Artificial
<220> FEATURE:
<223> OTHER INFORMATION: Synthetic Peptide

<400> SEQUENCE: 137

Tyr Arg Glu Gly Asp Asn Val Asp Gly
1               5

<210> SEQ ID NO 138
<211> LENGTH: 9
<212> TYPE: PRT
<213> ORGANISM: Artificial
<220> FEATURE:
<223> OTHER INFORMATION: Synthetic Peptide

<400> SEQUENCE: 138

Tyr Arg Glu Gly Asp Asn Val Glu Gly
1               5

<210> SEQ ID NO 139
<211> LENGTH: 9
<212> TYPE: PRT
<213> ORGANISM: Artificial
<220> FEATURE:
<223> OTHER INFORMATION: Synthetic Peptide

<400> SEQUENCE: 139

Tyr Arg Glu Gly Asp Asn Val Ser Gly
1               5

<210> SEQ ID NO 140
<211> LENGTH: 9
<212> TYPE: PRT
<213> ORGANISM: Artificial
<220> FEATURE:
<223> OTHER INFORMATION: Synthetic Peptide

<400> SEQUENCE: 140

Tyr Arg Glu Gly Asp Asn Val Thr Gly
1               5

<210> SEQ ID NO 141
<211> LENGTH: 9
<212> TYPE: PRT
<213> ORGANISM: Artificial
<220> FEATURE:
<223> OTHER INFORMATION: Synthetic Peptide

<400> SEQUENCE: 141

Tyr Arg Glu Gly Glu Asn Val Tyr Gly
1               5

<210> SEQ ID NO 142
<211> LENGTH: 9
<212> TYPE: PRT
<213> ORGANISM: Artificial
<220> FEATURE:
<223> OTHER INFORMATION: Synthetic Peptide

<400> SEQUENCE: 142

Tyr Arg Glu Gly Glu Asn Val Asp Gly
1               5

<210> SEQ ID NO 143
<211> LENGTH: 9
<212> TYPE: PRT
<213> ORGANISM: Artificial
<220> FEATURE:
<223> OTHER INFORMATION: Synthetic Peptide

<400> SEQUENCE: 143

Tyr Arg Glu Gly Glu Asn Val Glu Gly
1               5

<210> SEQ ID NO 144
<211> LENGTH: 9
<212> TYPE: PRT
<213> ORGANISM: Artificial
<220> FEATURE:
<223> OTHER INFORMATION: Synthetic Peptide

<400> SEQUENCE: 144

Tyr Arg Glu Gly Glu Asn Val Ser Gly
1               5

<210> SEQ ID NO 145
<211> LENGTH: 9
<212> TYPE: PRT
<213> ORGANISM: Artificial
<220> FEATURE:
<223> OTHER INFORMATION: Synthetic Peptide

<400> SEQUENCE: 145

Tyr Arg Glu Gly Glu Asn Val Thr Gly
1               5

<210> SEQ ID NO 146
<211> LENGTH: 9
<212> TYPE: PRT
<213> ORGANISM: Artificial
<220> FEATURE:
<223> OTHER INFORMATION: Synthetic Peptide

<400> SEQUENCE: 146

```
Tyr Arg Glu Gly Ser Asn Val Tyr Gly
1               5

<210> SEQ ID NO 147
<211> LENGTH: 9
<212> TYPE: PRT
<213> ORGANISM: Artificial
<220> FEATURE:
<223> OTHER INFORMATION: Synthetic Peptide

<400> SEQUENCE: 147

Tyr Arg Glu Gly Ser Asn Val Asp Gly
1               5

<210> SEQ ID NO 148
<211> LENGTH: 9
<212> TYPE: PRT
<213> ORGANISM: Artificial
<220> FEATURE:
<223> OTHER INFORMATION: Synthetic Peptide

<400> SEQUENCE: 148

Tyr Arg Glu Gly Ser Asn Val Glu Gly
1               5

<210> SEQ ID NO 149
<211> LENGTH: 9
<212> TYPE: PRT
<213> ORGANISM: Artificial
<220> FEATURE:
<223> OTHER INFORMATION: Synthetic Peptide

<400> SEQUENCE: 149

Tyr Arg Glu Gly Ser Asn Val Ser Gly
1               5

<210> SEQ ID NO 150
<211> LENGTH: 9
<212> TYPE: PRT
<213> ORGANISM: Artificial
<220> FEATURE:
<223> OTHER INFORMATION: Synthetic Peptide

<400> SEQUENCE: 150

Tyr Arg Glu Gly Ser Asn Val Thr Gly
1               5

<210> SEQ ID NO 151
<211> LENGTH: 9
<212> TYPE: PRT
<213> ORGANISM: Artificial
<220> FEATURE:
<223> OTHER INFORMATION: Synthetic Peptide

<400> SEQUENCE: 151

Tyr Arg Glu Gly Thr Asn Val Tyr Gly
1               5

<210> SEQ ID NO 152
<211> LENGTH: 9
<212> TYPE: PRT
<213> ORGANISM: Artificial
<220> FEATURE:
<223> OTHER INFORMATION: Synthetic Peptide

<400> SEQUENCE: 152
```

Tyr Arg Glu Gly Thr Asn Val Asp Gly
1               5

<210> SEQ ID NO 153
<211> LENGTH: 9
<212> TYPE: PRT
<213> ORGANISM: Artificial
<220> FEATURE:
<223> OTHER INFORMATION: Synthetic Peptide

<400> SEQUENCE: 153

Tyr Arg Glu Gly Thr Asn Val Glu Gly
1               5

<210> SEQ ID NO 154
<211> LENGTH: 9
<212> TYPE: PRT
<213> ORGANISM: Artificial
<220> FEATURE:
<223> OTHER INFORMATION: Synthetic Peptide

<400> SEQUENCE: 154

Tyr Arg Glu Gly Thr Asn Val Ser Gly
1               5

<210> SEQ ID NO 155
<211> LENGTH: 9
<212> TYPE: PRT
<213> ORGANISM: Artificial
<220> FEATURE:
<223> OTHER INFORMATION: Synthetic Peptide

<400> SEQUENCE: 155

Tyr Arg Glu Gly Thr Asn Val Thr Gly
1               5

<210> SEQ ID NO 156
<211> LENGTH: 9
<212> TYPE: PRT
<213> ORGANISM: Artificial
<220> FEATURE:
<223> OTHER INFORMATION: Synthetic Peptide

<400> SEQUENCE: 156

Asp Arg Glu Gly Tyr Asn Val Tyr Gly
1               5

<210> SEQ ID NO 157
<211> LENGTH: 9
<212> TYPE: PRT
<213> ORGANISM: Artificial
<220> FEATURE:
<223> OTHER INFORMATION: Synthetic Peptide

<400> SEQUENCE: 157

Asp Arg Glu Gly Tyr Asn Val Asp Gly
1               5

<210> SEQ ID NO 158
<211> LENGTH: 9
<212> TYPE: PRT
<213> ORGANISM: Artificial
<220> FEATURE:
<223> OTHER INFORMATION: Synthetic Peptide

<400> SEQUENCE: 158

Asp Arg Glu Gly Tyr Asn Val Glu Gly

```
<210> SEQ ID NO 159
<211> LENGTH: 9
<212> TYPE: PRT
<213> ORGANISM: Artificial
<220> FEATURE:
<223> OTHER INFORMATION: Synthetic Peptide

<400> SEQUENCE: 159

Asp Arg Glu Gly Tyr Asn Val Ser Gly
1               5

<210> SEQ ID NO 160
<211> LENGTH: 9
<212> TYPE: PRT
<213> ORGANISM: Artificial
<220> FEATURE:
<223> OTHER INFORMATION: Synthetic Peptide

<400> SEQUENCE: 160

Asp Arg Glu Gly Tyr Asn Val Thr Gly
1               5

<210> SEQ ID NO 161
<211> LENGTH: 9
<212> TYPE: PRT
<213> ORGANISM: Artificial
<220> FEATURE:
<223> OTHER INFORMATION: Synthetic Peptide

<400> SEQUENCE: 161

Asp Arg Glu Gly Asp Asn Val Tyr Gly
1               5

<210> SEQ ID NO 162
<211> LENGTH: 9
<212> TYPE: PRT
<213> ORGANISM: Artificial
<220> FEATURE:
<223> OTHER INFORMATION: Synthetic Peptide

<400> SEQUENCE: 162

Asp Arg Glu Gly Asp Asn Val Asp Gly
1               5

<210> SEQ ID NO 163
<211> LENGTH: 9
<212> TYPE: PRT
<213> ORGANISM: Artificial
<220> FEATURE:
<223> OTHER INFORMATION: Synthetic Peptide

<400> SEQUENCE: 163

Asp Arg Glu Gly Asp Asn Val Glu Gly
1               5

<210> SEQ ID NO 164
<211> LENGTH: 9
<212> TYPE: PRT
<213> ORGANISM: Artificial
<220> FEATURE:
<223> OTHER INFORMATION: Synthetic Peptide

<400> SEQUENCE: 164

Asp Arg Glu Gly Asp Asn Val Ser Gly
1               5
```

<210> SEQ ID NO 165
<211> LENGTH: 9
<212> TYPE: PRT
<213> ORGANISM: Artificial
<220> FEATURE:
<223> OTHER INFORMATION: Synthetic Peptide

<400> SEQUENCE: 165

Asp Arg Glu Gly Asp Asn Val Thr Gly
1               5

<210> SEQ ID NO 166
<211> LENGTH: 9
<212> TYPE: PRT
<213> ORGANISM: Artificial
<220> FEATURE:
<223> OTHER INFORMATION: Synthetic Peptide

<400> SEQUENCE: 166

Asp Arg Glu Gly Glu Asn Val Tyr Gly
1               5

<210> SEQ ID NO 167
<211> LENGTH: 9
<212> TYPE: PRT
<213> ORGANISM: Artificial
<220> FEATURE:
<223> OTHER INFORMATION: Synthetic Peptide

<400> SEQUENCE: 167

Asp Arg Glu Gly Glu Asn Val Asp Gly
1               5

<210> SEQ ID NO 168
<211> LENGTH: 9
<212> TYPE: PRT
<213> ORGANISM: Artificial
<220> FEATURE:
<223> OTHER INFORMATION: Synthetic Peptide

<400> SEQUENCE: 168

Asp Arg Glu Gly Glu Asn Val Glu Gly
1               5

<210> SEQ ID NO 169
<211> LENGTH: 9
<212> TYPE: PRT
<213> ORGANISM: Artificial
<220> FEATURE:
<223> OTHER INFORMATION: Synthetic Peptide

<400> SEQUENCE: 169

Asp Arg Glu Gly Glu Asn Val Ser Gly
1               5

<210> SEQ ID NO 170
<211> LENGTH: 9
<212> TYPE: PRT
<213> ORGANISM: Artificial
<220> FEATURE:
<223> OTHER INFORMATION: Synthetic Peptide

<400> SEQUENCE: 170

Asp Arg Glu Gly Glu Asn Val Thr Gly
1               5

```
<210> SEQ ID NO 171
<211> LENGTH: 9
<212> TYPE: PRT
<213> ORGANISM: Artificial
<220> FEATURE:
<223> OTHER INFORMATION: Synthetic Peptide

<400> SEQUENCE: 171

Asp Arg Glu Gly Ser Asn Val Tyr Gly
1               5

<210> SEQ ID NO 172
<211> LENGTH: 9
<212> TYPE: PRT
<213> ORGANISM: Artificial
<220> FEATURE:
<223> OTHER INFORMATION: Synthetic Peptide

<400> SEQUENCE: 172

Asp Arg Glu Gly Ser Asn Val Asp Gly
1               5

<210> SEQ ID NO 173
<211> LENGTH: 9
<212> TYPE: PRT
<213> ORGANISM: Artificial
<220> FEATURE:
<223> OTHER INFORMATION: Synthetic Peptide

<400> SEQUENCE: 173

Asp Arg Glu Gly Ser Asn Val Glu Gly
1               5

<210> SEQ ID NO 174
<211> LENGTH: 9
<212> TYPE: PRT
<213> ORGANISM: Artificial
<220> FEATURE:
<223> OTHER INFORMATION: Synthetic Peptide

<400> SEQUENCE: 174

Asp Arg Glu Gly Ser Asn Val Ser Gly
1               5

<210> SEQ ID NO 175
<211> LENGTH: 9
<212> TYPE: PRT
<213> ORGANISM: Artificial
<220> FEATURE:
<223> OTHER INFORMATION: Synthetic Peptide

<400> SEQUENCE: 175

Asp Arg Glu Gly Ser Asn Val Thr Gly
1               5

<210> SEQ ID NO 176
<211> LENGTH: 9
<212> TYPE: PRT
<213> ORGANISM: Artificial
<220> FEATURE:
<223> OTHER INFORMATION: Synthetic Peptide

<400> SEQUENCE: 176

Asp Arg Glu Gly Thr Asn Val Tyr Gly
1               5
```

```
<210> SEQ ID NO 177
<211> LENGTH: 9
<212> TYPE: PRT
<213> ORGANISM: Artificial
<220> FEATURE:
<223> OTHER INFORMATION: Synthetic Peptide

<400> SEQUENCE: 177

Asp Arg Glu Gly Thr Asn Val Asp Gly
1               5

<210> SEQ ID NO 178
<211> LENGTH: 9
<212> TYPE: PRT
<213> ORGANISM: Artificial
<220> FEATURE:
<223> OTHER INFORMATION: Synthetic Peptide

<400> SEQUENCE: 178

Asp Arg Glu Gly Thr Asn Val Glu Gly
1               5

<210> SEQ ID NO 179
<211> LENGTH: 9
<212> TYPE: PRT
<213> ORGANISM: Artificial
<220> FEATURE:
<223> OTHER INFORMATION: Synthetic Peptide

<400> SEQUENCE: 179

Asp Arg Glu Gly Thr Asn Val Ser Gly
1               5

<210> SEQ ID NO 180
<211> LENGTH: 9
<212> TYPE: PRT
<213> ORGANISM: Artificial
<220> FEATURE:
<223> OTHER INFORMATION: Synthetic Peptide

<400> SEQUENCE: 180

Asp Arg Glu Gly Thr Asn Val Thr Gly
1               5

<210> SEQ ID NO 181
<211> LENGTH: 9
<212> TYPE: PRT
<213> ORGANISM: Artificial
<220> FEATURE:
<223> OTHER INFORMATION: Synthetic Peptide

<400> SEQUENCE: 181

Glu Arg Glu Gly Tyr Asn Val Tyr Gly
1               5

<210> SEQ ID NO 182
<211> LENGTH: 9
<212> TYPE: PRT
<213> ORGANISM: Artificial
<220> FEATURE:
<223> OTHER INFORMATION: Synthetic Peptide

<400> SEQUENCE: 182

Glu Arg Glu Gly Tyr Asn Val Asp Gly
1               5

<210> SEQ ID NO 183
```

```
<211> LENGTH: 9
<212> TYPE: PRT
<213> ORGANISM: Artificial
<220> FEATURE:
<223> OTHER INFORMATION: Synthetic Peptide

<400> SEQUENCE: 183

Glu Arg Glu Gly Tyr Asn Val Glu Gly
1               5

<210> SEQ ID NO 184
<211> LENGTH: 9
<212> TYPE: PRT
<213> ORGANISM: Artificial
<220> FEATURE:
<223> OTHER INFORMATION: Synthetic Peptide

<400> SEQUENCE: 184

Glu Arg Glu Gly Tyr Asn Val Ser Gly
1               5

<210> SEQ ID NO 185
<211> LENGTH: 9
<212> TYPE: PRT
<213> ORGANISM: Artificial
<220> FEATURE:
<223> OTHER INFORMATION: Synthetic Peptide

<400> SEQUENCE: 185

Glu Arg Glu Gly Tyr Asn Val Thr Gly
1               5

<210> SEQ ID NO 186
<211> LENGTH: 9
<212> TYPE: PRT
<213> ORGANISM: Artificial
<220> FEATURE:
<223> OTHER INFORMATION: Synthetic Peptide

<400> SEQUENCE: 186

Glu Arg Glu Gly Asp Asn Val Tyr Gly
1               5

<210> SEQ ID NO 187
<211> LENGTH: 9
<212> TYPE: PRT
<213> ORGANISM: Artificial
<220> FEATURE:
<223> OTHER INFORMATION: Synthetic Peptide

<400> SEQUENCE: 187

Glu Arg Glu Gly Asp Asn Val Asp Gly
1               5

<210> SEQ ID NO 188
<211> LENGTH: 9
<212> TYPE: PRT
<213> ORGANISM: Artificial
<220> FEATURE:
<223> OTHER INFORMATION: Synthetic Peptide

<400> SEQUENCE: 188

Glu Arg Glu Gly Asp Asn Val Glu Gly
1               5

<210> SEQ ID NO 189
<211> LENGTH: 9
```

```
<212> TYPE: PRT
<213> ORGANISM: Artificial
<220> FEATURE:
<223> OTHER INFORMATION: Synthetic Peptide

<400> SEQUENCE: 189

Glu Arg Glu Gly Asp Asn Val Ser Gly
1               5

<210> SEQ ID NO 190
<211> LENGTH: 9
<212> TYPE: PRT
<213> ORGANISM: Artificial
<220> FEATURE:
<223> OTHER INFORMATION: Synthetic Peptide

<400> SEQUENCE: 190

Glu Arg Glu Gly Asp Asn Val Thr Gly
1               5

<210> SEQ ID NO 191
<211> LENGTH: 9
<212> TYPE: PRT
<213> ORGANISM: Artificial
<220> FEATURE:
<223> OTHER INFORMATION: Synthetic Peptide

<400> SEQUENCE: 191

Glu Arg Glu Gly Glu Asn Val Tyr Gly
1               5

<210> SEQ ID NO 192
<211> LENGTH: 9
<212> TYPE: PRT
<213> ORGANISM: Artificial
<220> FEATURE:
<223> OTHER INFORMATION: Synthetic Peptide

<400> SEQUENCE: 192

Glu Arg Glu Gly Glu Asn Val Asp Gly
1               5

<210> SEQ ID NO 193
<211> LENGTH: 9
<212> TYPE: PRT
<213> ORGANISM: Artificial
<220> FEATURE:
<223> OTHER INFORMATION: Synthetic Peptide

<400> SEQUENCE: 193

Glu Arg Glu Gly Glu Asn Val Glu Gly
1               5

<210> SEQ ID NO 194
<211> LENGTH: 9
<212> TYPE: PRT
<213> ORGANISM: Artificial
<220> FEATURE:
<223> OTHER INFORMATION: Synthetic Peptide

<400> SEQUENCE: 194

Glu Arg Glu Gly Glu Asn Val Ser Gly
1               5

<210> SEQ ID NO 195
<211> LENGTH: 9
<212> TYPE: PRT
```

```
<213> ORGANISM: Artificial
<220> FEATURE:
<223> OTHER INFORMATION: Synthetic Peptide

<400> SEQUENCE: 195

Glu Arg Glu Gly Glu Asn Val Thr Gly
1               5

<210> SEQ ID NO 196
<211> LENGTH: 9
<212> TYPE: PRT
<213> ORGANISM: Artificial
<220> FEATURE:
<223> OTHER INFORMATION: Synthetic Peptide

<400> SEQUENCE: 196

Glu Arg Glu Gly Ser Asn Val Tyr Gly
1               5

<210> SEQ ID NO 197
<211> LENGTH: 9
<212> TYPE: PRT
<213> ORGANISM: Artificial
<220> FEATURE:
<223> OTHER INFORMATION: Synthetic Peptide

<400> SEQUENCE: 197

Glu Arg Glu Gly Ser Asn Val Asp Gly
1               5

<210> SEQ ID NO 198
<211> LENGTH: 9
<212> TYPE: PRT
<213> ORGANISM: Artificial
<220> FEATURE:
<223> OTHER INFORMATION: Synthetic Peptide

<400> SEQUENCE: 198

Glu Arg Glu Gly Ser Asn Val Glu Gly
1               5

<210> SEQ ID NO 199
<211> LENGTH: 9
<212> TYPE: PRT
<213> ORGANISM: Artificial
<220> FEATURE:
<223> OTHER INFORMATION: Synthetic Peptide

<400> SEQUENCE: 199

Glu Arg Glu Gly Ser Asn Val Ser Gly
1               5

<210> SEQ ID NO 200
<211> LENGTH: 9
<212> TYPE: PRT
<213> ORGANISM: Artificial
<220> FEATURE:
<223> OTHER INFORMATION: Synthetic Peptide

<400> SEQUENCE: 200

Glu Arg Glu Gly Ser Asn Val Thr Gly
1               5

<210> SEQ ID NO 201
<211> LENGTH: 9
<212> TYPE: PRT
<213> ORGANISM: Artificial
```

```
<220> FEATURE:
<223> OTHER INFORMATION: Synthetic Peptide

<400> SEQUENCE: 201

Glu Arg Glu Gly Thr Asn Val Tyr Gly
1               5

<210> SEQ ID NO 202
<211> LENGTH: 9
<212> TYPE: PRT
<213> ORGANISM: Artificial
<220> FEATURE:
<223> OTHER INFORMATION: Synthetic Peptide

<400> SEQUENCE: 202

Glu Arg Glu Gly Thr Asn Val Asp Gly
1               5

<210> SEQ ID NO 203
<211> LENGTH: 9
<212> TYPE: PRT
<213> ORGANISM: Artificial
<220> FEATURE:
<223> OTHER INFORMATION: Synthetic Peptide

<400> SEQUENCE: 203

Glu Arg Glu Gly Thr Asn Val Glu Gly
1               5

<210> SEQ ID NO 204
<211> LENGTH: 9
<212> TYPE: PRT
<213> ORGANISM: Artificial
<220> FEATURE:
<223> OTHER INFORMATION: Synthetic Peptide

<400> SEQUENCE: 204

Glu Arg Glu Gly Thr Asn Val Ser Gly
1               5

<210> SEQ ID NO 205
<211> LENGTH: 9
<212> TYPE: PRT
<213> ORGANISM: Artificial
<220> FEATURE:
<223> OTHER INFORMATION: Synthetic Peptide

<400> SEQUENCE: 205

Glu Arg Glu Gly Thr Asn Val Thr Gly
1               5

<210> SEQ ID NO 206
<211> LENGTH: 9
<212> TYPE: PRT
<213> ORGANISM: Artificial
<220> FEATURE:
<223> OTHER INFORMATION: Synthetic Peptide

<400> SEQUENCE: 206

Ser Arg Glu Gly Tyr Asn Val Tyr Gly
1               5

<210> SEQ ID NO 207
<211> LENGTH: 9
<212> TYPE: PRT
<213> ORGANISM: Artificial
<220> FEATURE:
```

<223> OTHER INFORMATION: Synthetic Peptide

<400> SEQUENCE: 207

Ser Arg Glu Gly Tyr Asn Val Asp Gly
1               5

<210> SEQ ID NO 208
<211> LENGTH: 9
<212> TYPE: PRT
<213> ORGANISM: Artificial
<220> FEATURE:
<223> OTHER INFORMATION: Synthetic Peptide

<400> SEQUENCE: 208

Ser Arg Glu Gly Tyr Asn Val Glu Gly
1               5

<210> SEQ ID NO 209
<211> LENGTH: 9
<212> TYPE: PRT
<213> ORGANISM: Artificial
<220> FEATURE:
<223> OTHER INFORMATION: Synthetic Peptide

<400> SEQUENCE: 209

Ser Arg Glu Gly Tyr Asn Val Ser Gly
1               5

<210> SEQ ID NO 210
<211> LENGTH: 9
<212> TYPE: PRT
<213> ORGANISM: Artificial
<220> FEATURE:
<223> OTHER INFORMATION: Synthetic Peptide

<400> SEQUENCE: 210

Ser Arg Glu Gly Tyr Asn Val Thr Gly
1               5

<210> SEQ ID NO 211
<211> LENGTH: 9
<212> TYPE: PRT
<213> ORGANISM: Artificial
<220> FEATURE:
<223> OTHER INFORMATION: Synthetic Peptide

<400> SEQUENCE: 211

Ser Arg Glu Gly Asp Asn Val Tyr Gly
1               5

<210> SEQ ID NO 212
<211> LENGTH: 9
<212> TYPE: PRT
<213> ORGANISM: Artificial
<220> FEATURE:
<223> OTHER INFORMATION: Synthetic Peptide

<400> SEQUENCE: 212

Ser Arg Glu Gly Asp Asn Val Asp Gly
1               5

<210> SEQ ID NO 213
<211> LENGTH: 9
<212> TYPE: PRT
<213> ORGANISM: Artificial
<220> FEATURE:
<223> OTHER INFORMATION: Synthetic Peptide

<400> SEQUENCE: 213

Ser Arg Glu Gly Asp Asn Val Glu Gly
1               5

<210> SEQ ID NO 214
<211> LENGTH: 9
<212> TYPE: PRT
<213> ORGANISM: Artificial
<220> FEATURE:
<223> OTHER INFORMATION: Synthetic Peptide

<400> SEQUENCE: 214

Ser Arg Glu Gly Asp Asn Val Ser Gly
1               5

<210> SEQ ID NO 215
<211> LENGTH: 9
<212> TYPE: PRT
<213> ORGANISM: Artificial
<220> FEATURE:
<223> OTHER INFORMATION: Synthetic Peptide

<400> SEQUENCE: 215

Ser Arg Glu Gly Asp Asn Val Thr Gly
1               5

<210> SEQ ID NO 216
<211> LENGTH: 9
<212> TYPE: PRT
<213> ORGANISM: Artificial
<220> FEATURE:
<223> OTHER INFORMATION: Synthetic Peptide

<400> SEQUENCE: 216

Ser Arg Glu Gly Glu Asn Val Tyr Gly
1               5

<210> SEQ ID NO 217
<211> LENGTH: 9
<212> TYPE: PRT
<213> ORGANISM: Artificial
<220> FEATURE:
<223> OTHER INFORMATION: Synthetic Peptide

<400> SEQUENCE: 217

Ser Arg Glu Gly Glu Asn Val Asp Gly
1               5

<210> SEQ ID NO 218
<211> LENGTH: 9
<212> TYPE: PRT
<213> ORGANISM: Artificial
<220> FEATURE:
<223> OTHER INFORMATION: Synthetic Peptide

<400> SEQUENCE: 218

Ser Arg Glu Gly Glu Asn Val Glu Gly
1               5

<210> SEQ ID NO 219
<211> LENGTH: 9
<212> TYPE: PRT
<213> ORGANISM: Artificial
<220> FEATURE:
<223> OTHER INFORMATION: Synthetic Peptide

```
<400> SEQUENCE: 219

Ser Arg Glu Gly Glu Asn Val Ser Gly
1               5

<210> SEQ ID NO 220
<211> LENGTH: 9
<212> TYPE: PRT
<213> ORGANISM: Artificial
<220> FEATURE:
<223> OTHER INFORMATION: Synthetic Peptide

<400> SEQUENCE: 220

Ser Arg Glu Gly Glu Asn Val Thr Gly
1               5

<210> SEQ ID NO 221
<211> LENGTH: 9
<212> TYPE: PRT
<213> ORGANISM: Artificial
<220> FEATURE:
<223> OTHER INFORMATION: Synthetic Peptide

<400> SEQUENCE: 221

Ser Arg Glu Gly Ser Asn Val Tyr Gly
1               5

<210> SEQ ID NO 222
<211> LENGTH: 9
<212> TYPE: PRT
<213> ORGANISM: Artificial
<220> FEATURE:
<223> OTHER INFORMATION: Synthetic Peptide

<400> SEQUENCE: 222

Ser Arg Glu Gly Ser Asn Val Asp Gly
1               5

<210> SEQ ID NO 223
<211> LENGTH: 9
<212> TYPE: PRT
<213> ORGANISM: Artificial
<220> FEATURE:
<223> OTHER INFORMATION: Synthetic Peptide

<400> SEQUENCE: 223

Ser Arg Glu Gly Ser Asn Val Glu Gly
1               5

<210> SEQ ID NO 224
<211> LENGTH: 9
<212> TYPE: PRT
<213> ORGANISM: Artificial
<220> FEATURE:
<223> OTHER INFORMATION: Synthetic Peptide

<400> SEQUENCE: 224

Ser Arg Glu Gly Ser Asn Val Ser Gly
1               5

<210> SEQ ID NO 225
<211> LENGTH: 9
<212> TYPE: PRT
<213> ORGANISM: Artificial
<220> FEATURE:
<223> OTHER INFORMATION: Synthetic Peptide

<400> SEQUENCE: 225
```

Ser Arg Glu Gly Ser Asn Val Thr Gly
1               5

<210> SEQ ID NO 226
<211> LENGTH: 9
<212> TYPE: PRT
<213> ORGANISM: Artificial
<220> FEATURE:
<223> OTHER INFORMATION: Synthetic Peptide

<400> SEQUENCE: 226

Ser Arg Glu Gly Thr Asn Val Tyr Gly
1               5

<210> SEQ ID NO 227
<211> LENGTH: 9
<212> TYPE: PRT
<213> ORGANISM: Artificial
<220> FEATURE:
<223> OTHER INFORMATION: Synthetic Peptide

<400> SEQUENCE: 227

Ser Arg Glu Gly Thr Asn Val Asp Gly
1               5

<210> SEQ ID NO 228
<211> LENGTH: 9
<212> TYPE: PRT
<213> ORGANISM: Artificial
<220> FEATURE:
<223> OTHER INFORMATION: Synthetic Peptide

<400> SEQUENCE: 228

Ser Arg Glu Gly Thr Asn Val Glu Gly
1               5

<210> SEQ ID NO 229
<211> LENGTH: 9
<212> TYPE: PRT
<213> ORGANISM: Artificial
<220> FEATURE:
<223> OTHER INFORMATION: Synthetic Peptide

<400> SEQUENCE: 229

Ser Arg Glu Gly Thr Asn Val Ser Gly
1               5

<210> SEQ ID NO 230
<211> LENGTH: 9
<212> TYPE: PRT
<213> ORGANISM: Artificial
<220> FEATURE:
<223> OTHER INFORMATION: Synthetic Peptide

<400> SEQUENCE: 230

Ser Arg Glu Gly Thr Asn Val Thr Gly
1               5

<210> SEQ ID NO 231
<211> LENGTH: 9
<212> TYPE: PRT
<213> ORGANISM: Artificial
<220> FEATURE:
<223> OTHER INFORMATION: Synthetic Peptide

<400> SEQUENCE: 231

Thr Arg Glu Gly Tyr Asn Val Tyr Gly
1               5

<210> SEQ ID NO 232
<211> LENGTH: 9
<212> TYPE: PRT
<213> ORGANISM: Artificial
<220> FEATURE:
<223> OTHER INFORMATION: Synthetic Peptide

<400> SEQUENCE: 232

Thr Arg Glu Gly Tyr Asn Val Asp Gly
1               5

<210> SEQ ID NO 233
<211> LENGTH: 9
<212> TYPE: PRT
<213> ORGANISM: Artificial
<220> FEATURE:
<223> OTHER INFORMATION: Synthetic Peptide

<400> SEQUENCE: 233

Thr Arg Glu Gly Tyr Asn Val Glu Gly
1               5

<210> SEQ ID NO 234
<211> LENGTH: 9
<212> TYPE: PRT
<213> ORGANISM: Artificial
<220> FEATURE:
<223> OTHER INFORMATION: Synthetic Peptide

<400> SEQUENCE: 234

Thr Arg Glu Gly Tyr Asn Val Ser Gly
1               5

<210> SEQ ID NO 235
<211> LENGTH: 9
<212> TYPE: PRT
<213> ORGANISM: Artificial
<220> FEATURE:
<223> OTHER INFORMATION: Synthetic Peptide

<400> SEQUENCE: 235

Thr Arg Glu Gly Tyr Asn Val Thr Gly
1               5

<210> SEQ ID NO 236
<211> LENGTH: 9
<212> TYPE: PRT
<213> ORGANISM: Artificial
<220> FEATURE:
<223> OTHER INFORMATION: Synthetic Peptide

<400> SEQUENCE: 236

Thr Arg Glu Gly Asp Asn Val Tyr Gly
1               5

<210> SEQ ID NO 237
<211> LENGTH: 9
<212> TYPE: PRT
<213> ORGANISM: Artificial
<220> FEATURE:
<223> OTHER INFORMATION: Synthetic Peptide

<400> SEQUENCE: 237

Thr Arg Glu Gly Asp Asn Val Asp Gly

```
1               5

<210> SEQ ID NO 238
<211> LENGTH: 9
<212> TYPE: PRT
<213> ORGANISM: Artificial
<220> FEATURE:
<223> OTHER INFORMATION: Synthetic Peptide

<400> SEQUENCE: 238

Thr Arg Glu Gly Asp Asn Val Glu Gly
1               5

<210> SEQ ID NO 239
<211> LENGTH: 9
<212> TYPE: PRT
<213> ORGANISM: Artificial
<220> FEATURE:
<223> OTHER INFORMATION: Synthetic Peptide

<400> SEQUENCE: 239

Thr Arg Glu Gly Asp Asn Val Ser Gly
1               5

<210> SEQ ID NO 240
<211> LENGTH: 9
<212> TYPE: PRT
<213> ORGANISM: Artificial
<220> FEATURE:
<223> OTHER INFORMATION: Synthetic Peptide

<400> SEQUENCE: 240

Thr Arg Glu Gly Asp Asn Val Thr Gly
1               5

<210> SEQ ID NO 241
<211> LENGTH: 9
<212> TYPE: PRT
<213> ORGANISM: Artificial
<220> FEATURE:
<223> OTHER INFORMATION: Synthetic Peptide

<400> SEQUENCE: 241

Thr Arg Glu Gly Glu Asn Val Tyr Gly
1               5

<210> SEQ ID NO 242
<211> LENGTH: 9
<212> TYPE: PRT
<213> ORGANISM: Artificial
<220> FEATURE:
<223> OTHER INFORMATION: Synthetic Peptide

<400> SEQUENCE: 242

Thr Arg Glu Gly Glu Asn Val Asp Gly
1               5

<210> SEQ ID NO 243
<211> LENGTH: 9
<212> TYPE: PRT
<213> ORGANISM: Artificial
<220> FEATURE:
<223> OTHER INFORMATION: Synthetic Peptide

<400> SEQUENCE: 243

Thr Arg Glu Gly Glu Asn Val Glu Gly
1               5
```

<210> SEQ ID NO 244
<211> LENGTH: 9
<212> TYPE: PRT
<213> ORGANISM: Artificial
<220> FEATURE:
<223> OTHER INFORMATION: Synthetic Peptide

<400> SEQUENCE: 244

Thr Arg Glu Gly Glu Asn Val Ser Gly
1               5

<210> SEQ ID NO 245
<211> LENGTH: 9
<212> TYPE: PRT
<213> ORGANISM: Artificial
<220> FEATURE:
<223> OTHER INFORMATION: Synthetic Peptide

<400> SEQUENCE: 245

Thr Arg Glu Gly Glu Asn Val Thr Gly
1               5

<210> SEQ ID NO 246
<211> LENGTH: 9
<212> TYPE: PRT
<213> ORGANISM: Artificial
<220> FEATURE:
<223> OTHER INFORMATION: Synthetic Peptide

<400> SEQUENCE: 246

Thr Arg Glu Gly Ser Asn Val Tyr Gly
1               5

<210> SEQ ID NO 247
<211> LENGTH: 9
<212> TYPE: PRT
<213> ORGANISM: Artificial
<220> FEATURE:
<223> OTHER INFORMATION: Synthetic Peptide

<400> SEQUENCE: 247

Thr Arg Glu Gly Ser Asn Val Asp Gly
1               5

<210> SEQ ID NO 248
<211> LENGTH: 9
<212> TYPE: PRT
<213> ORGANISM: Artificial
<220> FEATURE:
<223> OTHER INFORMATION: Synthetic Peptide

<400> SEQUENCE: 248

Thr Arg Glu Gly Ser Asn Val Glu Gly
1               5

<210> SEQ ID NO 249
<211> LENGTH: 9
<212> TYPE: PRT
<213> ORGANISM: Artificial
<220> FEATURE:
<223> OTHER INFORMATION: Synthetic Peptide

<400> SEQUENCE: 249

Thr Arg Glu Gly Ser Asn Val Ser Gly
1               5

```
<210> SEQ ID NO 250
<211> LENGTH: 9
<212> TYPE: PRT
<213> ORGANISM: Artificial
<220> FEATURE:
<223> OTHER INFORMATION: Synthetic Peptide

<400> SEQUENCE: 250

Thr Arg Glu Gly Ser Asn Val Thr Gly
1               5

<210> SEQ ID NO 251
<211> LENGTH: 9
<212> TYPE: PRT
<213> ORGANISM: Artificial
<220> FEATURE:
<223> OTHER INFORMATION: Synthetic Peptide

<400> SEQUENCE: 251

Thr Arg Glu Gly Thr Asn Val Tyr Gly
1               5

<210> SEQ ID NO 252
<211> LENGTH: 9
<212> TYPE: PRT
<213> ORGANISM: Artificial
<220> FEATURE:
<223> OTHER INFORMATION: Synthetic Peptide

<400> SEQUENCE: 252

Thr Arg Glu Gly Thr Asn Val Asp Gly
1               5

<210> SEQ ID NO 253
<211> LENGTH: 9
<212> TYPE: PRT
<213> ORGANISM: Artificial
<220> FEATURE:
<223> OTHER INFORMATION: Synthetic Peptide

<400> SEQUENCE: 253

Thr Arg Glu Gly Thr Asn Val Glu Gly
1               5

<210> SEQ ID NO 254
<211> LENGTH: 9
<212> TYPE: PRT
<213> ORGANISM: Artificial
<220> FEATURE:
<223> OTHER INFORMATION: Synthetic Peptide

<400> SEQUENCE: 254

Thr Arg Glu Gly Thr Asn Val Ser Gly
1               5

<210> SEQ ID NO 255
<211> LENGTH: 9
<212> TYPE: PRT
<213> ORGANISM: Artificial
<220> FEATURE:
<223> OTHER INFORMATION: Synthetic Peptide

<400> SEQUENCE: 255

Thr Arg Glu Gly Thr Asn Val Thr Gly
1               5
```

```
<210> SEQ ID NO 256
<211> LENGTH: 11
<212> TYPE: PRT
<213> ORGANISM: Artificial
<220> FEATURE:
<223> OTHER INFORMATION: Synthetic Peptide

<400> SEQUENCE: 256

Tyr Lys Glu Gly Tyr Asn Val Asp Gly Ile Glu
1               5                   10

<210> SEQ ID NO 257
<211> LENGTH: 11
<212> TYPE: PRT
<213> ORGANISM: Artificial
<220> FEATURE:
<223> OTHER INFORMATION: Synthetic Peptide

<400> SEQUENCE: 257

Tyr Lys Glu Gly Tyr Asn Val Glu Gly Ile Glu
1               5                   10

<210> SEQ ID NO 258
<211> LENGTH: 11
<212> TYPE: PRT
<213> ORGANISM: Artificial
<220> FEATURE:
<223> OTHER INFORMATION: Synthetic Peptide

<400> SEQUENCE: 258

Tyr Lys Glu Gly Tyr Asn Val Ser Gly Ile Glu
1               5                   10

<210> SEQ ID NO 259
<211> LENGTH: 11
<212> TYPE: PRT
<213> ORGANISM: Artificial
<220> FEATURE:
<223> OTHER INFORMATION: Synthetic Peptide

<400> SEQUENCE: 259

Tyr Lys Glu Gly Tyr Asn Val Thr Gly Ile Glu
1               5                   10

<210> SEQ ID NO 260
<211> LENGTH: 11
<212> TYPE: PRT
<213> ORGANISM: Artificial
<220> FEATURE:
<223> OTHER INFORMATION: Synthetic Peptide

<400> SEQUENCE: 260

Tyr Lys Glu Gly Asp Asn Val Tyr Gly Ile Glu
1               5                   10

<210> SEQ ID NO 261
<211> LENGTH: 11
<212> TYPE: PRT
<213> ORGANISM: Artificial
<220> FEATURE:
<223> OTHER INFORMATION: Synthetic Peptide

<400> SEQUENCE: 261

Tyr Lys Glu Gly Asp Asn Val Asp Gly Ile Glu
1               5                   10

<210> SEQ ID NO 262
```

```
<211> LENGTH: 11
<212> TYPE: PRT
<213> ORGANISM: Artificial
<220> FEATURE:
<223> OTHER INFORMATION: Synthetic Peptide

<400> SEQUENCE: 262

Tyr Lys Glu Gly Asp Asn Val Glu Gly Ile Glu
1               5                   10

<210> SEQ ID NO 263
<211> LENGTH: 11
<212> TYPE: PRT
<213> ORGANISM: Artificial
<220> FEATURE:
<223> OTHER INFORMATION: Synthetic Peptide

<400> SEQUENCE: 263

Tyr Lys Glu Gly Asp Asn Val Ser Gly Ile Glu
1               5                   10

<210> SEQ ID NO 264
<211> LENGTH: 11
<212> TYPE: PRT
<213> ORGANISM: Artificial
<220> FEATURE:
<223> OTHER INFORMATION: Synthetic Peptide

<400> SEQUENCE: 264

Tyr Lys Glu Gly Asp Asn Val Thr Gly Ile Glu
1               5                   10

<210> SEQ ID NO 265
<211> LENGTH: 11
<212> TYPE: PRT
<213> ORGANISM: Artificial
<220> FEATURE:
<223> OTHER INFORMATION: Synthetic Peptide

<400> SEQUENCE: 265

Tyr Lys Glu Gly Glu Asn Val Tyr Gly Ile Glu
1               5                   10

<210> SEQ ID NO 266
<211> LENGTH: 11
<212> TYPE: PRT
<213> ORGANISM: Artificial
<220> FEATURE:
<223> OTHER INFORMATION: Synthetic Peptide

<400> SEQUENCE: 266

Tyr Lys Glu Gly Glu Asn Val Asp Gly Ile Glu
1               5                   10

<210> SEQ ID NO 267
<211> LENGTH: 11
<212> TYPE: PRT
<213> ORGANISM: Artificial
<220> FEATURE:
<223> OTHER INFORMATION: Synthetic Peptide

<400> SEQUENCE: 267

Tyr Lys Glu Gly Glu Asn Val Glu Gly Ile Glu
1               5                   10

<210> SEQ ID NO 268
<211> LENGTH: 11
```

<212> TYPE: PRT
<213> ORGANISM: Artificial
<220> FEATURE:
<223> OTHER INFORMATION: Synthetic Peptide

<400> SEQUENCE: 268

Tyr Lys Glu Gly Glu Asn Val Ser Gly Ile Glu
1               5                   10

<210> SEQ ID NO 269
<211> LENGTH: 11
<212> TYPE: PRT
<213> ORGANISM: Artificial
<220> FEATURE:
<223> OTHER INFORMATION: Synthetic Peptide

<400> SEQUENCE: 269

Tyr Lys Glu Gly Glu Asn Val Thr Gly Ile Glu
1               5                   10

<210> SEQ ID NO 270
<211> LENGTH: 11
<212> TYPE: PRT
<213> ORGANISM: Artificial
<220> FEATURE:
<223> OTHER INFORMATION: Synthetic Peptide

<400> SEQUENCE: 270

Tyr Lys Glu Gly Ser Asn Val Tyr Gly Ile Glu
1               5                   10

<210> SEQ ID NO 271
<211> LENGTH: 11
<212> TYPE: PRT
<213> ORGANISM: Artificial
<220> FEATURE:
<223> OTHER INFORMATION: Synthetic Peptide

<400> SEQUENCE: 271

Tyr Lys Glu Gly Ser Asn Val Asp Gly Ile Glu
1               5                   10

<210> SEQ ID NO 272
<211> LENGTH: 11
<212> TYPE: PRT
<213> ORGANISM: Artificial
<220> FEATURE:
<223> OTHER INFORMATION: Synthetic Peptide

<400> SEQUENCE: 272

Tyr Lys Glu Gly Ser Asn Val Glu Gly Ile Glu
1               5                   10

<210> SEQ ID NO 273
<211> LENGTH: 11
<212> TYPE: PRT
<213> ORGANISM: Artificial
<220> FEATURE:
<223> OTHER INFORMATION: Synthetic Peptide

<400> SEQUENCE: 273

Tyr Lys Glu Gly Ser Asn Val Ser Gly Ile Glu
1               5                   10

<210> SEQ ID NO 274
<211> LENGTH: 11
<212> TYPE: PRT

<213> ORGANISM: Artificial
<220> FEATURE:
<223> OTHER INFORMATION: Synthetic Peptide

<400> SEQUENCE: 274

Tyr Lys Glu Gly Ser Asn Val Thr Gly Ile Glu
1               5                   10

<210> SEQ ID NO 275
<211> LENGTH: 11
<212> TYPE: PRT
<213> ORGANISM: Artificial
<220> FEATURE:
<223> OTHER INFORMATION: Synthetic Peptide

<400> SEQUENCE: 275

Tyr Lys Glu Gly Thr Asn Val Tyr Gly Ile Glu
1               5                   10

<210> SEQ ID NO 276
<211> LENGTH: 11
<212> TYPE: PRT
<213> ORGANISM: Artificial
<220> FEATURE:
<223> OTHER INFORMATION: Synthetic Peptide

<400> SEQUENCE: 276

Tyr Lys Glu Gly Thr Asn Val Asp Gly Ile Glu
1               5                   10

<210> SEQ ID NO 277
<211> LENGTH: 11
<212> TYPE: PRT
<213> ORGANISM: Artificial
<220> FEATURE:
<223> OTHER INFORMATION: Synthetic Peptide

<400> SEQUENCE: 277

Tyr Lys Glu Gly Thr Asn Val Glu Gly Ile Glu
1               5                   10

<210> SEQ ID NO 278
<211> LENGTH: 11
<212> TYPE: PRT
<213> ORGANISM: Artificial
<220> FEATURE:
<223> OTHER INFORMATION: Synthetic Peptide

<400> SEQUENCE: 278

Tyr Lys Glu Gly Thr Asn Val Ser Gly Ile Glu
1               5                   10

<210> SEQ ID NO 279
<211> LENGTH: 11
<212> TYPE: PRT
<213> ORGANISM: Artificial
<220> FEATURE:
<223> OTHER INFORMATION: Synthetic Peptide

<400> SEQUENCE: 279

Tyr Lys Glu Gly Thr Asn Val Thr Gly Ile Glu
1               5                   10

<210> SEQ ID NO 280
<211> LENGTH: 11
<212> TYPE: PRT
<213> ORGANISM: Artificial

<220> FEATURE:
<223> OTHER INFORMATION: Synthetic Peptide

<400> SEQUENCE: 280

Asp Lys Glu Gly Tyr Asn Val Tyr Gly Ile Glu
1               5                   10

<210> SEQ ID NO 281
<211> LENGTH: 11
<212> TYPE: PRT
<213> ORGANISM: Artificial
<220> FEATURE:
<223> OTHER INFORMATION: Synthetic Peptide

<400> SEQUENCE: 281

Asp Lys Glu Gly Tyr Asn Val Asp Gly Ile Glu
1               5                   10

<210> SEQ ID NO 282
<211> LENGTH: 11
<212> TYPE: PRT
<213> ORGANISM: Artificial
<220> FEATURE:
<223> OTHER INFORMATION: Synthetic Peptide

<400> SEQUENCE: 282

Asp Lys Glu Gly Tyr Asn Val Glu Gly Ile Glu
1               5                   10

<210> SEQ ID NO 283
<211> LENGTH: 11
<212> TYPE: PRT
<213> ORGANISM: Artificial
<220> FEATURE:
<223> OTHER INFORMATION: Synthetic Peptide

<400> SEQUENCE: 283

Asp Lys Glu Gly Tyr Asn Val Ser Gly Ile Glu
1               5                   10

<210> SEQ ID NO 284
<211> LENGTH: 11
<212> TYPE: PRT
<213> ORGANISM: Artificial
<220> FEATURE:
<223> OTHER INFORMATION: Synthetic Peptide

<400> SEQUENCE: 284

Asp Lys Glu Gly Tyr Asn Val Thr Gly Ile Glu
1               5                   10

<210> SEQ ID NO 285
<211> LENGTH: 11
<212> TYPE: PRT
<213> ORGANISM: Artificial
<220> FEATURE:
<223> OTHER INFORMATION: Synthetic Peptide

<400> SEQUENCE: 285

Asp Lys Glu Gly Asp Asn Val Tyr Gly Ile Glu
1               5                   10

<210> SEQ ID NO 286
<211> LENGTH: 11
<212> TYPE: PRT
<213> ORGANISM: Artificial
<220> FEATURE:

```
<223> OTHER INFORMATION: Synthetic Peptide

<400> SEQUENCE: 286

Asp Lys Glu Gly Asp Asn Val Asp Gly Ile Glu
1               5                   10

<210> SEQ ID NO 287
<211> LENGTH: 11
<212> TYPE: PRT
<213> ORGANISM: Artificial
<220> FEATURE:
<223> OTHER INFORMATION: Synthetic Peptide

<400> SEQUENCE: 287

Asp Lys Glu Gly Asp Asn Val Glu Gly Ile Glu
1               5                   10

<210> SEQ ID NO 288
<211> LENGTH: 11
<212> TYPE: PRT
<213> ORGANISM: Artificial
<220> FEATURE:
<223> OTHER INFORMATION: Synthetic Peptide

<400> SEQUENCE: 288

Asp Lys Glu Gly Asp Asn Val Ser Gly Ile Glu
1               5                   10

<210> SEQ ID NO 289
<211> LENGTH: 11
<212> TYPE: PRT
<213> ORGANISM: Artificial
<220> FEATURE:
<223> OTHER INFORMATION: Synthetic Peptide

<400> SEQUENCE: 289

Asp Lys Glu Gly Asp Asn Val Thr Gly Ile Glu
1               5                   10

<210> SEQ ID NO 290
<211> LENGTH: 11
<212> TYPE: PRT
<213> ORGANISM: Artificial
<220> FEATURE:
<223> OTHER INFORMATION: Synthetic Peptide

<400> SEQUENCE: 290

Asp Lys Glu Gly Glu Asn Val Tyr Gly Ile Glu
1               5                   10

<210> SEQ ID NO 291
<211> LENGTH: 11
<212> TYPE: PRT
<213> ORGANISM: Artificial
<220> FEATURE:
<223> OTHER INFORMATION: Synthetic Peptide

<400> SEQUENCE: 291

Asp Lys Glu Gly Glu Asn Val Asp Gly Ile Glu
1               5                   10

<210> SEQ ID NO 292
<211> LENGTH: 11
<212> TYPE: PRT
<213> ORGANISM: Artificial
<220> FEATURE:
<223> OTHER INFORMATION: Synthetic Peptide
```

```
<400> SEQUENCE: 292

Asp Lys Glu Gly Glu Asn Val Glu Gly Ile Glu
1               5                   10

<210> SEQ ID NO 293
<211> LENGTH: 11
<212> TYPE: PRT
<213> ORGANISM: Artificial
<220> FEATURE:
<223> OTHER INFORMATION: Synthetic Peptide

<400> SEQUENCE: 293

Asp Lys Glu Gly Glu Asn Val Ser Gly Ile Glu
1               5                   10

<210> SEQ ID NO 294
<211> LENGTH: 11
<212> TYPE: PRT
<213> ORGANISM: Artificial
<220> FEATURE:
<223> OTHER INFORMATION: Synthetic Peptide

<400> SEQUENCE: 294

Asp Lys Glu Gly Glu Asn Val Thr Gly Ile Glu
1               5                   10

<210> SEQ ID NO 295
<211> LENGTH: 11
<212> TYPE: PRT
<213> ORGANISM: Artificial
<220> FEATURE:
<223> OTHER INFORMATION: Synthetic Peptide

<400> SEQUENCE: 295

Asp Lys Glu Gly Ser Asn Val Tyr Gly Ile Glu
1               5                   10

<210> SEQ ID NO 296
<211> LENGTH: 11
<212> TYPE: PRT
<213> ORGANISM: Artificial
<220> FEATURE:
<223> OTHER INFORMATION: Synthetic Peptide

<400> SEQUENCE: 296

Asp Lys Glu Gly Ser Asn Val Asp Gly Ile Glu
1               5                   10

<210> SEQ ID NO 297
<211> LENGTH: 11
<212> TYPE: PRT
<213> ORGANISM: Artificial
<220> FEATURE:
<223> OTHER INFORMATION: Synthetic Peptide

<400> SEQUENCE: 297

Asp Lys Glu Gly Ser Asn Val Glu Gly Ile Glu
1               5                   10

<210> SEQ ID NO 298
<211> LENGTH: 11
<212> TYPE: PRT
<213> ORGANISM: Artificial
<220> FEATURE:
<223> OTHER INFORMATION: Synthetic Peptide
```

```
<400> SEQUENCE: 298

Asp Lys Glu Gly Ser Asn Val Ser Gly Ile Glu
1               5                   10

<210> SEQ ID NO 299
<211> LENGTH: 11
<212> TYPE: PRT
<213> ORGANISM: Artificial
<220> FEATURE:
<223> OTHER INFORMATION: Synthetic Peptide

<400> SEQUENCE: 299

Asp Lys Glu Gly Ser Asn Val Thr Gly Ile Glu
1               5                   10

<210> SEQ ID NO 300
<211> LENGTH: 11
<212> TYPE: PRT
<213> ORGANISM: Artificial
<220> FEATURE:
<223> OTHER INFORMATION: Synthetic Peptide

<400> SEQUENCE: 300

Asp Lys Glu Gly Thr Asn Val Tyr Gly Ile Glu
1               5                   10

<210> SEQ ID NO 301
<211> LENGTH: 11
<212> TYPE: PRT
<213> ORGANISM: Artificial
<220> FEATURE:
<223> OTHER INFORMATION: Synthetic Peptide

<400> SEQUENCE: 301

Asp Lys Glu Gly Thr Asn Val Asp Gly Ile Glu
1               5                   10

<210> SEQ ID NO 302
<211> LENGTH: 11
<212> TYPE: PRT
<213> ORGANISM: Artificial
<220> FEATURE:
<223> OTHER INFORMATION: Synthetic Peptide

<400> SEQUENCE: 302

Asp Lys Glu Gly Thr Asn Val Glu Gly Ile Glu
1               5                   10

<210> SEQ ID NO 303
<211> LENGTH: 11
<212> TYPE: PRT
<213> ORGANISM: Artificial
<220> FEATURE:
<223> OTHER INFORMATION: Synthetic Peptide

<400> SEQUENCE: 303

Asp Lys Glu Gly Thr Asn Val Ser Gly Ile Glu
1               5                   10

<210> SEQ ID NO 304
<211> LENGTH: 11
<212> TYPE: PRT
<213> ORGANISM: Artificial
<220> FEATURE:
<223> OTHER INFORMATION: Synthetic Peptide

<400> SEQUENCE: 304
```

```
Asp Lys Glu Gly Thr Asn Val Thr Gly Ile Glu
1               5                   10

<210> SEQ ID NO 305
<211> LENGTH: 11
<212> TYPE: PRT
<213> ORGANISM: Artificial
<220> FEATURE:
<223> OTHER INFORMATION: Synthetic Peptide

<400> SEQUENCE: 305

Glu Lys Glu Gly Tyr Asn Val Tyr Gly Ile Glu
1               5                   10

<210> SEQ ID NO 306
<211> LENGTH: 11
<212> TYPE: PRT
<213> ORGANISM: Artificial
<220> FEATURE:
<223> OTHER INFORMATION: Synthetic Peptide

<400> SEQUENCE: 306

Glu Lys Glu Gly Tyr Asn Val Asp Gly Ile Glu
1               5                   10

<210> SEQ ID NO 307
<211> LENGTH: 11
<212> TYPE: PRT
<213> ORGANISM: Artificial
<220> FEATURE:
<223> OTHER INFORMATION: Synthetic Peptide

<400> SEQUENCE: 307

Glu Lys Glu Gly Tyr Asn Val Glu Gly Ile Glu
1               5                   10

<210> SEQ ID NO 308
<211> LENGTH: 11
<212> TYPE: PRT
<213> ORGANISM: Artificial
<220> FEATURE:
<223> OTHER INFORMATION: Synthetic Peptide

<400> SEQUENCE: 308

Glu Lys Glu Gly Tyr Asn Val Ser Gly Ile Glu
1               5                   10

<210> SEQ ID NO 309
<211> LENGTH: 11
<212> TYPE: PRT
<213> ORGANISM: Artificial
<220> FEATURE:
<223> OTHER INFORMATION: Synthetic Peptide

<400> SEQUENCE: 309

Glu Lys Glu Gly Tyr Asn Val Thr Gly Ile Glu
1               5                   10

<210> SEQ ID NO 310
<211> LENGTH: 11
<212> TYPE: PRT
<213> ORGANISM: Artificial
<220> FEATURE:
<223> OTHER INFORMATION: Synthetic Peptide

<400> SEQUENCE: 310
```

Glu Lys Glu Gly Asp Asn Val Tyr Gly Ile Glu
1               5                   10

<210> SEQ ID NO 311
<211> LENGTH: 11
<212> TYPE: PRT
<213> ORGANISM: Artificial
<220> FEATURE:
<223> OTHER INFORMATION: Synthetic Peptide

<400> SEQUENCE: 311

Glu Lys Glu Gly Asp Asn Val Asp Gly Ile Glu
1               5                   10

<210> SEQ ID NO 312
<211> LENGTH: 11
<212> TYPE: PRT
<213> ORGANISM: Artificial
<220> FEATURE:
<223> OTHER INFORMATION: Synthetic Peptide

<400> SEQUENCE: 312

Glu Lys Glu Gly Asp Asn Val Glu Gly Ile Glu
1               5                   10

<210> SEQ ID NO 313
<211> LENGTH: 11
<212> TYPE: PRT
<213> ORGANISM: Artificial
<220> FEATURE:
<223> OTHER INFORMATION: Synthetic Peptide

<400> SEQUENCE: 313

Glu Lys Glu Gly Asp Asn Val Ser Gly Ile Glu
1               5                   10

<210> SEQ ID NO 314
<211> LENGTH: 11
<212> TYPE: PRT
<213> ORGANISM: Artificial
<220> FEATURE:
<223> OTHER INFORMATION: Synthetic Peptide

<400> SEQUENCE: 314

Glu Lys Glu Gly Asp Asn Val Thr Gly Ile Glu
1               5                   10

<210> SEQ ID NO 315
<211> LENGTH: 11
<212> TYPE: PRT
<213> ORGANISM: Artificial
<220> FEATURE:
<223> OTHER INFORMATION: Synthetic Peptide

<400> SEQUENCE: 315

Glu Lys Glu Gly Glu Asn Val Tyr Gly Ile Glu
1               5                   10

<210> SEQ ID NO 316
<211> LENGTH: 11
<212> TYPE: PRT
<213> ORGANISM: Artificial
<220> FEATURE:
<223> OTHER INFORMATION: Synthetic Peptide

<400> SEQUENCE: 316

Glu Lys Glu Gly Glu Asn Val Asp Gly Ile Glu

```
1               5                   10
```

<210> SEQ ID NO 317
<211> LENGTH: 11
<212> TYPE: PRT
<213> ORGANISM: Artificial
<220> FEATURE:
<223> OTHER INFORMATION: Synthetic Peptide

<400> SEQUENCE: 317

```
Glu Lys Glu Gly Glu Asn Val Glu Gly Ile Glu
1               5                   10
```

<210> SEQ ID NO 318
<211> LENGTH: 11
<212> TYPE: PRT
<213> ORGANISM: Artificial
<220> FEATURE:
<223> OTHER INFORMATION: Synthetic Peptide

<400> SEQUENCE: 318

```
Glu Lys Glu Gly Glu Asn Val Ser Gly Ile Glu
1               5                   10
```

<210> SEQ ID NO 319
<211> LENGTH: 11
<212> TYPE: PRT
<213> ORGANISM: Artificial
<220> FEATURE:
<223> OTHER INFORMATION: Synthetic Peptide

<400> SEQUENCE: 319

```
Glu Lys Glu Gly Glu Asn Val Thr Gly Ile Glu
1               5                   10
```

<210> SEQ ID NO 320
<211> LENGTH: 11
<212> TYPE: PRT
<213> ORGANISM: Artificial
<220> FEATURE:
<223> OTHER INFORMATION: Synthetic Peptide

<400> SEQUENCE: 320

```
Glu Lys Glu Gly Ser Asn Val Tyr Gly Ile Glu
1               5                   10
```

<210> SEQ ID NO 321
<211> LENGTH: 11
<212> TYPE: PRT
<213> ORGANISM: Artificial
<220> FEATURE:
<223> OTHER INFORMATION: Synthetic Peptide

<400> SEQUENCE: 321

```
Glu Lys Glu Gly Ser Asn Val Asp Gly Ile Glu
1               5                   10
```

<210> SEQ ID NO 322
<211> LENGTH: 11
<212> TYPE: PRT
<213> ORGANISM: Artificial
<220> FEATURE:
<223> OTHER INFORMATION: Synthetic Peptide

<400> SEQUENCE: 322

```
Glu Lys Glu Gly Ser Asn Val Glu Gly Ile Glu
1               5                   10
```

```
<210> SEQ ID NO 323
<211> LENGTH: 11
<212> TYPE: PRT
<213> ORGANISM: Artificial
<220> FEATURE:
<223> OTHER INFORMATION: Synthetic Peptide

<400> SEQUENCE: 323

Glu Lys Glu Gly Ser Asn Val Ser Gly Ile Glu
1               5                   10

<210> SEQ ID NO 324
<211> LENGTH: 11
<212> TYPE: PRT
<213> ORGANISM: Artificial
<220> FEATURE:
<223> OTHER INFORMATION: Synthetic Peptide

<400> SEQUENCE: 324

Glu Lys Glu Gly Ser Asn Val Thr Gly Ile Glu
1               5                   10

<210> SEQ ID NO 325
<211> LENGTH: 11
<212> TYPE: PRT
<213> ORGANISM: Artificial
<220> FEATURE:
<223> OTHER INFORMATION: Synthetic Peptide

<400> SEQUENCE: 325

Glu Lys Glu Gly Thr Asn Val Tyr Gly Ile Glu
1               5                   10

<210> SEQ ID NO 326
<211> LENGTH: 11
<212> TYPE: PRT
<213> ORGANISM: Artificial
<220> FEATURE:
<223> OTHER INFORMATION: Synthetic Peptide

<400> SEQUENCE: 326

Glu Lys Glu Gly Thr Asn Val Asp Gly Ile Glu
1               5                   10

<210> SEQ ID NO 327
<211> LENGTH: 11
<212> TYPE: PRT
<213> ORGANISM: Artificial
<220> FEATURE:
<223> OTHER INFORMATION: Synthetic Peptide

<400> SEQUENCE: 327

Glu Lys Glu Gly Thr Asn Val Glu Gly Ile Glu
1               5                   10

<210> SEQ ID NO 328
<211> LENGTH: 11
<212> TYPE: PRT
<213> ORGANISM: Artificial
<220> FEATURE:
<223> OTHER INFORMATION: Synthetic Peptide

<400> SEQUENCE: 328

Glu Lys Glu Gly Thr Asn Val Ser Gly Ile Glu
1               5                   10
```

```
<210> SEQ ID NO 329
<211> LENGTH: 11
<212> TYPE: PRT
<213> ORGANISM: Artificial
<220> FEATURE:
<223> OTHER INFORMATION: Synthetic Peptide

<400> SEQUENCE: 329

Glu Lys Glu Gly Thr Asn Val Thr Gly Ile Glu
1               5                   10

<210> SEQ ID NO 330
<211> LENGTH: 11
<212> TYPE: PRT
<213> ORGANISM: Artificial
<220> FEATURE:
<223> OTHER INFORMATION: Synthetic Peptide

<400> SEQUENCE: 330

Ser Lys Glu Gly Tyr Asn Val Tyr Gly Ile Glu
1               5                   10

<210> SEQ ID NO 331
<211> LENGTH: 11
<212> TYPE: PRT
<213> ORGANISM: Artificial
<220> FEATURE:
<223> OTHER INFORMATION: Synthetic Peptide

<400> SEQUENCE: 331

Ser Lys Glu Gly Tyr Asn Val Asp Gly Ile Glu
1               5                   10

<210> SEQ ID NO 332
<211> LENGTH: 11
<212> TYPE: PRT
<213> ORGANISM: Artificial
<220> FEATURE:
<223> OTHER INFORMATION: Synthetic Peptide

<400> SEQUENCE: 332

Ser Lys Glu Gly Tyr Asn Val Glu Gly Ile Glu
1               5                   10

<210> SEQ ID NO 333
<211> LENGTH: 11
<212> TYPE: PRT
<213> ORGANISM: Artificial
<220> FEATURE:
<223> OTHER INFORMATION: Synthetic Peptide

<400> SEQUENCE: 333

Ser Lys Glu Gly Tyr Asn Val Ser Gly Ile Glu
1               5                   10

<210> SEQ ID NO 334
<211> LENGTH: 11
<212> TYPE: PRT
<213> ORGANISM: Artificial
<220> FEATURE:
<223> OTHER INFORMATION: Synthetic Peptide

<400> SEQUENCE: 334

Ser Lys Glu Gly Tyr Asn Val Thr Gly Ile Glu
1               5                   10
```

```
<210> SEQ ID NO 335
<211> LENGTH: 11
<212> TYPE: PRT
<213> ORGANISM: Artificial
<220> FEATURE:
<223> OTHER INFORMATION: Synthetic Peptide

<400> SEQUENCE: 335

Ser Lys Glu Gly Asp Asn Val Tyr Gly Ile Glu
1               5                   10

<210> SEQ ID NO 336
<211> LENGTH: 11
<212> TYPE: PRT
<213> ORGANISM: Artificial
<220> FEATURE:
<223> OTHER INFORMATION: Synthetic Peptide

<400> SEQUENCE: 336

Ser Lys Glu Gly Asp Asn Val Asp Gly Ile Glu
1               5                   10

<210> SEQ ID NO 337
<211> LENGTH: 11
<212> TYPE: PRT
<213> ORGANISM: Artificial
<220> FEATURE:
<223> OTHER INFORMATION: Synthetic Peptide

<400> SEQUENCE: 337

Ser Lys Glu Gly Asp Asn Val Glu Gly Ile Glu
1               5                   10

<210> SEQ ID NO 338
<211> LENGTH: 11
<212> TYPE: PRT
<213> ORGANISM: Artificial
<220> FEATURE:
<223> OTHER INFORMATION: Synthetic Peptide

<400> SEQUENCE: 338

Ser Lys Glu Gly Asp Asn Val Ser Gly Ile Glu
1               5                   10

<210> SEQ ID NO 339
<211> LENGTH: 11
<212> TYPE: PRT
<213> ORGANISM: Artificial
<220> FEATURE:
<223> OTHER INFORMATION: Synthetic Peptide

<400> SEQUENCE: 339

Ser Lys Glu Gly Asp Asn Val Thr Gly Ile Glu
1               5                   10

<210> SEQ ID NO 340
<211> LENGTH: 11
<212> TYPE: PRT
<213> ORGANISM: Artificial
<220> FEATURE:
<223> OTHER INFORMATION: Synthetic Peptide

<400> SEQUENCE: 340

Ser Lys Glu Gly Glu Asn Val Tyr Gly Ile Glu
1               5                   10

<210> SEQ ID NO 341
```

```
<211> LENGTH: 11
<212> TYPE: PRT
<213> ORGANISM: Artificial
<220> FEATURE:
<223> OTHER INFORMATION: Synthetic Peptide

<400> SEQUENCE: 341

Ser Lys Glu Gly Glu Asn Val Asp Gly Ile Glu
1               5                   10

<210> SEQ ID NO 342
<211> LENGTH: 11
<212> TYPE: PRT
<213> ORGANISM: Artificial
<220> FEATURE:
<223> OTHER INFORMATION: Synthetic Peptide

<400> SEQUENCE: 342

Ser Lys Glu Gly Glu Asn Val Glu Gly Ile Glu
1               5                   10

<210> SEQ ID NO 343
<211> LENGTH: 11
<212> TYPE: PRT
<213> ORGANISM: Artificial
<220> FEATURE:
<223> OTHER INFORMATION: Synthetic Peptide

<400> SEQUENCE: 343

Ser Lys Glu Gly Glu Asn Val Ser Gly Ile Glu
1               5                   10

<210> SEQ ID NO 344
<211> LENGTH: 11
<212> TYPE: PRT
<213> ORGANISM: Artificial
<220> FEATURE:
<223> OTHER INFORMATION: Synthetic Peptide

<400> SEQUENCE: 344

Ser Lys Glu Gly Glu Asn Val Thr Gly Ile Glu
1               5                   10

<210> SEQ ID NO 345
<211> LENGTH: 11
<212> TYPE: PRT
<213> ORGANISM: Artificial
<220> FEATURE:
<223> OTHER INFORMATION: Synthetic Peptide

<400> SEQUENCE: 345

Ser Lys Glu Gly Ser Asn Val Tyr Gly Ile Glu
1               5                   10

<210> SEQ ID NO 346
<211> LENGTH: 11
<212> TYPE: PRT
<213> ORGANISM: Artificial
<220> FEATURE:
<223> OTHER INFORMATION: Synthetic Peptide

<400> SEQUENCE: 346

Ser Lys Glu Gly Ser Asn Val Asp Gly Ile Glu
1               5                   10

<210> SEQ ID NO 347
<211> LENGTH: 11
```

```
<212> TYPE: PRT
<213> ORGANISM: Artificial
<220> FEATURE:
<223> OTHER INFORMATION: Synthetic Peptide

<400> SEQUENCE: 347

Ser Lys Glu Gly Ser Asn Val Glu Gly Ile Glu
1               5                   10

<210> SEQ ID NO 348
<211> LENGTH: 11
<212> TYPE: PRT
<213> ORGANISM: Artificial
<220> FEATURE:
<223> OTHER INFORMATION: Synthetic Peptide

<400> SEQUENCE: 348

Ser Lys Glu Gly Ser Asn Val Ser Gly Ile Glu
1               5                   10

<210> SEQ ID NO 349
<211> LENGTH: 11
<212> TYPE: PRT
<213> ORGANISM: Artificial
<220> FEATURE:
<223> OTHER INFORMATION: Synthetic Peptide

<400> SEQUENCE: 349

Ser Lys Glu Gly Ser Asn Val Thr Gly Ile Glu
1               5                   10

<210> SEQ ID NO 350
<211> LENGTH: 11
<212> TYPE: PRT
<213> ORGANISM: Artificial
<220> FEATURE:
<223> OTHER INFORMATION: Synthetic Peptide

<400> SEQUENCE: 350

Ser Lys Glu Gly Thr Asn Val Tyr Gly Ile Glu
1               5                   10

<210> SEQ ID NO 351
<211> LENGTH: 11
<212> TYPE: PRT
<213> ORGANISM: Artificial
<220> FEATURE:
<223> OTHER INFORMATION: Synthetic Peptide

<400> SEQUENCE: 351

Ser Lys Glu Gly Thr Asn Val Asp Gly Ile Glu
1               5                   10

<210> SEQ ID NO 352
<211> LENGTH: 11
<212> TYPE: PRT
<213> ORGANISM: Artificial
<220> FEATURE:
<223> OTHER INFORMATION: Synthetic Peptide

<400> SEQUENCE: 352

Ser Lys Glu Gly Thr Asn Val Glu Gly Ile Glu
1               5                   10

<210> SEQ ID NO 353
<211> LENGTH: 11
<212> TYPE: PRT
```

```
<213> ORGANISM: Artificial
<220> FEATURE:
<223> OTHER INFORMATION: Synthetic Peptide

<400> SEQUENCE: 353

Ser Lys Glu Gly Thr Asn Val Ser Gly Ile Glu
1               5                   10

<210> SEQ ID NO 354
<211> LENGTH: 11
<212> TYPE: PRT
<213> ORGANISM: Artificial
<220> FEATURE:
<223> OTHER INFORMATION: Synthetic Peptide

<400> SEQUENCE: 354

Ser Lys Glu Gly Thr Asn Val Thr Gly Ile Glu
1               5                   10

<210> SEQ ID NO 355
<211> LENGTH: 11
<212> TYPE: PRT
<213> ORGANISM: Artificial
<220> FEATURE:
<223> OTHER INFORMATION: Synthetic Peptide

<400> SEQUENCE: 355

Thr Lys Glu Gly Tyr Asn Val Tyr Gly Ile Glu
1               5                   10

<210> SEQ ID NO 356
<211> LENGTH: 11
<212> TYPE: PRT
<213> ORGANISM: Artificial
<220> FEATURE:
<223> OTHER INFORMATION: Synthetic Peptide

<400> SEQUENCE: 356

Thr Lys Glu Gly Tyr Asn Val Asp Gly Ile Glu
1               5                   10

<210> SEQ ID NO 357
<211> LENGTH: 11
<212> TYPE: PRT
<213> ORGANISM: Artificial
<220> FEATURE:
<223> OTHER INFORMATION: Synthetic Peptide

<400> SEQUENCE: 357

Thr Lys Glu Gly Tyr Asn Val Glu Gly Ile Glu
1               5                   10

<210> SEQ ID NO 358
<211> LENGTH: 11
<212> TYPE: PRT
<213> ORGANISM: Artificial
<220> FEATURE:
<223> OTHER INFORMATION: Synthetic Peptide

<400> SEQUENCE: 358

Thr Lys Glu Gly Tyr Asn Val Ser Gly Ile Glu
1               5                   10

<210> SEQ ID NO 359
<211> LENGTH: 11
<212> TYPE: PRT
<213> ORGANISM: Artificial
```

```
<220> FEATURE:
<223> OTHER INFORMATION: Synthetic Peptide

<400> SEQUENCE: 359

Thr Lys Glu Gly Tyr Asn Val Thr Gly Ile Glu
1               5                   10

<210> SEQ ID NO 360
<211> LENGTH: 11
<212> TYPE: PRT
<213> ORGANISM: Artificial
<220> FEATURE:
<223> OTHER INFORMATION: Synthetic Peptide

<400> SEQUENCE: 360

Thr Lys Glu Gly Asp Asn Val Tyr Gly Ile Glu
1               5                   10

<210> SEQ ID NO 361
<211> LENGTH: 11
<212> TYPE: PRT
<213> ORGANISM: Artificial
<220> FEATURE:
<223> OTHER INFORMATION: Synthetic Peptide

<400> SEQUENCE: 361

Thr Lys Glu Gly Asp Asn Val Asp Gly Ile Glu
1               5                   10

<210> SEQ ID NO 362
<211> LENGTH: 11
<212> TYPE: PRT
<213> ORGANISM: Artificial
<220> FEATURE:
<223> OTHER INFORMATION: Synthetic Peptide

<400> SEQUENCE: 362

Thr Lys Glu Gly Asp Asn Val Glu Gly Ile Glu
1               5                   10

<210> SEQ ID NO 363
<211> LENGTH: 11
<212> TYPE: PRT
<213> ORGANISM: Artificial
<220> FEATURE:
<223> OTHER INFORMATION: Synthetic Peptide

<400> SEQUENCE: 363

Thr Lys Glu Gly Asp Asn Val Ser Gly Ile Glu
1               5                   10

<210> SEQ ID NO 364
<211> LENGTH: 11
<212> TYPE: PRT
<213> ORGANISM: Artificial
<220> FEATURE:
<223> OTHER INFORMATION: Synthetic Peptide

<400> SEQUENCE: 364

Thr Lys Glu Gly Asp Asn Val Thr Gly Ile Glu
1               5                   10

<210> SEQ ID NO 365
<211> LENGTH: 11
<212> TYPE: PRT
<213> ORGANISM: Artificial
<220> FEATURE:
```

<223> OTHER INFORMATION: Synthetic Peptide

<400> SEQUENCE: 365

Thr Lys Glu Gly Glu Asn Val Tyr Gly Ile Glu
1               5                   10

<210> SEQ ID NO 366
<211> LENGTH: 11
<212> TYPE: PRT
<213> ORGANISM: Artificial
<220> FEATURE:
<223> OTHER INFORMATION: Synthetic Peptide

<400> SEQUENCE: 366

Thr Lys Glu Gly Glu Asn Val Asp Gly Ile Glu
1               5                   10

<210> SEQ ID NO 367
<211> LENGTH: 11
<212> TYPE: PRT
<213> ORGANISM: Artificial
<220> FEATURE:
<223> OTHER INFORMATION: Synthetic Peptide

<400> SEQUENCE: 367

Thr Lys Glu Gly Glu Asn Val Glu Gly Ile Glu
1               5                   10

<210> SEQ ID NO 368
<211> LENGTH: 11
<212> TYPE: PRT
<213> ORGANISM: Artificial
<220> FEATURE:
<223> OTHER INFORMATION: Synthetic Peptide

<400> SEQUENCE: 368

Thr Lys Glu Gly Glu Asn Val Ser Gly Ile Glu
1               5                   10

<210> SEQ ID NO 369
<211> LENGTH: 11
<212> TYPE: PRT
<213> ORGANISM: Artificial
<220> FEATURE:
<223> OTHER INFORMATION: Synthetic Peptide

<400> SEQUENCE: 369

Thr Lys Glu Gly Glu Asn Val Thr Gly Ile Glu
1               5                   10

<210> SEQ ID NO 370
<211> LENGTH: 11
<212> TYPE: PRT
<213> ORGANISM: Artificial
<220> FEATURE:
<223> OTHER INFORMATION: Synthetic Peptide

<400> SEQUENCE: 370

Thr Lys Glu Gly Ser Asn Val Tyr Gly Ile Glu
1               5                   10

<210> SEQ ID NO 371
<211> LENGTH: 11
<212> TYPE: PRT
<213> ORGANISM: Artificial
<220> FEATURE:
<223> OTHER INFORMATION: Synthetic Peptide

<400> SEQUENCE: 371

Thr Lys Glu Gly Ser Asn Val Asp Gly Ile Glu
1               5                   10

<210> SEQ ID NO 372
<211> LENGTH: 11
<212> TYPE: PRT
<213> ORGANISM: Artificial
<220> FEATURE:
<223> OTHER INFORMATION: Synthetic Peptide

<400> SEQUENCE: 372

Thr Lys Glu Gly Ser Asn Val Glu Gly Ile Glu
1               5                   10

<210> SEQ ID NO 373
<211> LENGTH: 11
<212> TYPE: PRT
<213> ORGANISM: Artificial
<220> FEATURE:
<223> OTHER INFORMATION: Synthetic Peptide

<400> SEQUENCE: 373

Thr Lys Glu Gly Ser Asn Val Ser Gly Ile Glu
1               5                   10

<210> SEQ ID NO 374
<211> LENGTH: 11
<212> TYPE: PRT
<213> ORGANISM: Artificial
<220> FEATURE:
<223> OTHER INFORMATION: Synthetic Peptide

<400> SEQUENCE: 374

Thr Lys Glu Gly Ser Asn Val Thr Gly Ile Glu
1               5                   10

<210> SEQ ID NO 375
<211> LENGTH: 11
<212> TYPE: PRT
<213> ORGANISM: Artificial
<220> FEATURE:
<223> OTHER INFORMATION: Synthetic Peptide

<400> SEQUENCE: 375

Thr Lys Glu Gly Thr Asn Val Tyr Gly Ile Glu
1               5                   10

<210> SEQ ID NO 376
<211> LENGTH: 11
<212> TYPE: PRT
<213> ORGANISM: Artificial
<220> FEATURE:
<223> OTHER INFORMATION: Synthetic Peptide

<400> SEQUENCE: 376

Thr Lys Glu Gly Thr Asn Val Asp Gly Ile Glu
1               5                   10

<210> SEQ ID NO 377
<211> LENGTH: 11
<212> TYPE: PRT
<213> ORGANISM: Artificial
<220> FEATURE:
<223> OTHER INFORMATION: Synthetic Peptide

```
<400> SEQUENCE: 377

Thr Lys Glu Gly Thr Asn Val Glu Gly Ile Glu
1               5                   10

<210> SEQ ID NO 378
<211> LENGTH: 11
<212> TYPE: PRT
<213> ORGANISM: Artificial
<220> FEATURE:
<223> OTHER INFORMATION: Synthetic Peptide

<400> SEQUENCE: 378

Thr Lys Glu Gly Thr Asn Val Ser Gly Ile Glu
1               5                   10

<210> SEQ ID NO 379
<211> LENGTH: 11
<212> TYPE: PRT
<213> ORGANISM: Artificial
<220> FEATURE:
<223> OTHER INFORMATION: Synthetic Peptide

<400> SEQUENCE: 379

Thr Lys Glu Gly Thr Asn Val Thr Gly Ile Glu
1               5                   10

<210> SEQ ID NO 380
<211> LENGTH: 11
<212> TYPE: PRT
<213> ORGANISM: Artificial
<220> FEATURE:
<223> OTHER INFORMATION: Synthetic Peptide

<400> SEQUENCE: 380

Tyr Arg Glu Gly Tyr Asn Val Asp Gly Ile Glu
1               5                   10

<210> SEQ ID NO 381
<211> LENGTH: 11
<212> TYPE: PRT
<213> ORGANISM: Artificial
<220> FEATURE:
<223> OTHER INFORMATION: Synthetic Peptide

<400> SEQUENCE: 381

Tyr Arg Glu Gly Tyr Asn Val Glu Gly Ile Glu
1               5                   10

<210> SEQ ID NO 382
<211> LENGTH: 11
<212> TYPE: PRT
<213> ORGANISM: Artificial
<220> FEATURE:
<223> OTHER INFORMATION: Synthetic Peptide

<400> SEQUENCE: 382

Tyr Arg Glu Gly Tyr Asn Val Ser Gly Ile Glu
1               5                   10

<210> SEQ ID NO 383
<211> LENGTH: 11
<212> TYPE: PRT
<213> ORGANISM: Artificial
<220> FEATURE:
<223> OTHER INFORMATION: Synthetic Peptide

<400> SEQUENCE: 383
```

Tyr Arg Glu Gly Tyr Asn Val Thr Gly Ile Glu
1               5                   10

<210> SEQ ID NO 384
<211> LENGTH: 11
<212> TYPE: PRT
<213> ORGANISM: Artificial
<220> FEATURE:
<223> OTHER INFORMATION: Synthetic Peptide

<400> SEQUENCE: 384

Tyr Arg Glu Gly Asp Asn Val Tyr Gly Ile Glu
1               5                   10

<210> SEQ ID NO 385
<211> LENGTH: 11
<212> TYPE: PRT
<213> ORGANISM: Artificial
<220> FEATURE:
<223> OTHER INFORMATION: Synthetic Peptide

<400> SEQUENCE: 385

Tyr Arg Glu Gly Asp Asn Val Asp Gly Ile Glu
1               5                   10

<210> SEQ ID NO 386
<211> LENGTH: 11
<212> TYPE: PRT
<213> ORGANISM: Artificial
<220> FEATURE:
<223> OTHER INFORMATION: Synthetic Peptide

<400> SEQUENCE: 386

Tyr Arg Glu Gly Asp Asn Val Glu Gly Ile Glu
1               5                   10

<210> SEQ ID NO 387
<211> LENGTH: 11
<212> TYPE: PRT
<213> ORGANISM: Artificial
<220> FEATURE:
<223> OTHER INFORMATION: Synthetic Peptide

<400> SEQUENCE: 387

Tyr Arg Glu Gly Asp Asn Val Ser Gly Ile Glu
1               5                   10

<210> SEQ ID NO 388
<211> LENGTH: 11
<212> TYPE: PRT
<213> ORGANISM: Artificial
<220> FEATURE:
<223> OTHER INFORMATION: Synthetic Peptide

<400> SEQUENCE: 388

Tyr Arg Glu Gly Asp Asn Val Thr Gly Ile Glu
1               5                   10

<210> SEQ ID NO 389
<211> LENGTH: 11
<212> TYPE: PRT
<213> ORGANISM: Artificial
<220> FEATURE:
<223> OTHER INFORMATION: Synthetic Peptide

<400> SEQUENCE: 389

```
Tyr Arg Glu Gly Glu Asn Val Tyr Gly Ile Glu
1               5                   10
```

<210> SEQ ID NO 390
<211> LENGTH: 11
<212> TYPE: PRT
<213> ORGANISM: Artificial
<220> FEATURE:
<223> OTHER INFORMATION: Synthetic Peptide

<400> SEQUENCE: 390

```
Tyr Arg Glu Gly Glu Asn Val Asp Gly Ile Glu
1               5                   10
```

<210> SEQ ID NO 391
<211> LENGTH: 11
<212> TYPE: PRT
<213> ORGANISM: Artificial
<220> FEATURE:
<223> OTHER INFORMATION: Synthetic Peptide

<400> SEQUENCE: 391

```
Tyr Arg Glu Gly Glu Asn Val Glu Gly Ile Glu
1               5                   10
```

<210> SEQ ID NO 392
<211> LENGTH: 11
<212> TYPE: PRT
<213> ORGANISM: Artificial
<220> FEATURE:
<223> OTHER INFORMATION: Synthetic Peptide

<400> SEQUENCE: 392

```
Tyr Arg Glu Gly Glu Asn Val Ser Gly Ile Glu
1               5                   10
```

<210> SEQ ID NO 393
<211> LENGTH: 11
<212> TYPE: PRT
<213> ORGANISM: Artificial
<220> FEATURE:
<223> OTHER INFORMATION: Synthetic Peptide

<400> SEQUENCE: 393

```
Tyr Arg Glu Gly Glu Asn Val Thr Gly Ile Glu
1               5                   10
```

<210> SEQ ID NO 394
<211> LENGTH: 11
<212> TYPE: PRT
<213> ORGANISM: Artificial
<220> FEATURE:
<223> OTHER INFORMATION: Synthetic Peptide

<400> SEQUENCE: 394

```
Tyr Arg Glu Gly Ser Asn Val Tyr Gly Ile Glu
1               5                   10
```

<210> SEQ ID NO 395
<211> LENGTH: 11
<212> TYPE: PRT
<213> ORGANISM: Artificial
<220> FEATURE:
<223> OTHER INFORMATION: Synthetic Peptide

<400> SEQUENCE: 395

```
Tyr Arg Glu Gly Ser Asn Val Asp Gly Ile Glu
```

```
1               5                   10
```

<210> SEQ ID NO 396
<211> LENGTH: 11
<212> TYPE: PRT
<213> ORGANISM: Artificial
<220> FEATURE:
<223> OTHER INFORMATION: Synthetic Peptide

<400> SEQUENCE: 396

Tyr Arg Glu Gly Ser Asn Val Glu Gly Ile Glu
1               5                   10

<210> SEQ ID NO 397
<211> LENGTH: 11
<212> TYPE: PRT
<213> ORGANISM: Artificial
<220> FEATURE:
<223> OTHER INFORMATION: Synthetic Peptide

<400> SEQUENCE: 397

Tyr Arg Glu Gly Ser Asn Val Ser Gly Ile Glu
1               5                   10

<210> SEQ ID NO 398
<211> LENGTH: 11
<212> TYPE: PRT
<213> ORGANISM: Artificial
<220> FEATURE:
<223> OTHER INFORMATION: Synthetic Peptide

<400> SEQUENCE: 398

Tyr Arg Glu Gly Ser Asn Val Thr Gly Ile Glu
1               5                   10

<210> SEQ ID NO 399
<211> LENGTH: 11
<212> TYPE: PRT
<213> ORGANISM: Artificial
<220> FEATURE:
<223> OTHER INFORMATION: Synthetic Peptide

<400> SEQUENCE: 399

Tyr Arg Glu Gly Thr Asn Val Tyr Gly Ile Glu
1               5                   10

<210> SEQ ID NO 400
<211> LENGTH: 11
<212> TYPE: PRT
<213> ORGANISM: Artificial
<220> FEATURE:
<223> OTHER INFORMATION: Synthetic Peptide

<400> SEQUENCE: 400

Tyr Arg Glu Gly Thr Asn Val Asp Gly Ile Glu
1               5                   10

<210> SEQ ID NO 401
<211> LENGTH: 11
<212> TYPE: PRT
<213> ORGANISM: Artificial
<220> FEATURE:
<223> OTHER INFORMATION: Synthetic Peptide

<400> SEQUENCE: 401

Tyr Arg Glu Gly Thr Asn Val Glu Gly Ile Glu
1               5                   10

<210> SEQ ID NO 402
<211> LENGTH: 11
<212> TYPE: PRT
<213> ORGANISM: Artificial
<220> FEATURE:
<223> OTHER INFORMATION: Synthetic Peptide

<400> SEQUENCE: 402

Tyr Arg Glu Gly Thr Asn Val Ser Gly Ile Glu
1               5                   10

<210> SEQ ID NO 403
<211> LENGTH: 11
<212> TYPE: PRT
<213> ORGANISM: Artificial
<220> FEATURE:
<223> OTHER INFORMATION: Synthetic Peptide

<400> SEQUENCE: 403

Tyr Arg Glu Gly Thr Asn Val Thr Gly Ile Glu
1               5                   10

<210> SEQ ID NO 404
<211> LENGTH: 11
<212> TYPE: PRT
<213> ORGANISM: Artificial
<220> FEATURE:
<223> OTHER INFORMATION: Synthetic Peptide

<400> SEQUENCE: 404

Asp Arg Glu Gly Tyr Asn Val Tyr Gly Ile Glu
1               5                   10

<210> SEQ ID NO 405
<211> LENGTH: 11
<212> TYPE: PRT
<213> ORGANISM: Artificial
<220> FEATURE:
<223> OTHER INFORMATION: Synthetic Peptide

<400> SEQUENCE: 405

Asp Arg Glu Gly Tyr Asn Val Asp Gly Ile Glu
1               5                   10

<210> SEQ ID NO 406
<211> LENGTH: 11
<212> TYPE: PRT
<213> ORGANISM: Artificial
<220> FEATURE:
<223> OTHER INFORMATION: Synthetic Peptide

<400> SEQUENCE: 406

Asp Arg Glu Gly Tyr Asn Val Glu Gly Ile Glu
1               5                   10

<210> SEQ ID NO 407
<211> LENGTH: 11
<212> TYPE: PRT
<213> ORGANISM: Artificial
<220> FEATURE:
<223> OTHER INFORMATION: Synthetic Peptide

<400> SEQUENCE: 407

Asp Arg Glu Gly Tyr Asn Val Ser Gly Ile Glu
1               5                   10

```
<210> SEQ ID NO 408
<211> LENGTH: 11
<212> TYPE: PRT
<213> ORGANISM: Artificial
<220> FEATURE:
<223> OTHER INFORMATION: Synthetic Peptide

<400> SEQUENCE: 408

Asp Arg Glu Gly Tyr Asn Val Thr Gly Ile Glu
1               5                   10

<210> SEQ ID NO 409
<211> LENGTH: 11
<212> TYPE: PRT
<213> ORGANISM: Artificial
<220> FEATURE:
<223> OTHER INFORMATION: Synthetic Peptide

<400> SEQUENCE: 409

Asp Arg Glu Gly Asp Asn Val Tyr Gly Ile Glu
1               5                   10

<210> SEQ ID NO 410
<211> LENGTH: 11
<212> TYPE: PRT
<213> ORGANISM: Artificial
<220> FEATURE:
<223> OTHER INFORMATION: Synthetic Peptide

<400> SEQUENCE: 410

Asp Arg Glu Gly Asp Asn Val Asp Gly Ile Glu
1               5                   10

<210> SEQ ID NO 411
<211> LENGTH: 11
<212> TYPE: PRT
<213> ORGANISM: Artificial
<220> FEATURE:
<223> OTHER INFORMATION: Synthetic Peptide

<400> SEQUENCE: 411

Asp Arg Glu Gly Asp Asn Val Glu Gly Ile Glu
1               5                   10

<210> SEQ ID NO 412
<211> LENGTH: 11
<212> TYPE: PRT
<213> ORGANISM: Artificial
<220> FEATURE:
<223> OTHER INFORMATION: Synthetic Peptide

<400> SEQUENCE: 412

Asp Arg Glu Gly Asp Asn Val Ser Gly Ile Glu
1               5                   10

<210> SEQ ID NO 413
<211> LENGTH: 11
<212> TYPE: PRT
<213> ORGANISM: Artificial
<220> FEATURE:
<223> OTHER INFORMATION: Synthetic Peptide

<400> SEQUENCE: 413

Asp Arg Glu Gly Asp Asn Val Thr Gly Ile Glu
1               5                   10
```

-continued

```
<210> SEQ ID NO 414
<211> LENGTH: 11
<212> TYPE: PRT
<213> ORGANISM: Artificial
<220> FEATURE:
<223> OTHER INFORMATION: Synthetic Peptide

<400> SEQUENCE: 414

Asp Arg Glu Gly Glu Asn Val Tyr Gly Ile Glu
1               5                   10

<210> SEQ ID NO 415
<211> LENGTH: 11
<212> TYPE: PRT
<213> ORGANISM: Artificial
<220> FEATURE:
<223> OTHER INFORMATION: Synthetic Peptide

<400> SEQUENCE: 415

Asp Arg Glu Gly Glu Asn Val Asp Gly Ile Glu
1               5                   10

<210> SEQ ID NO 416
<211> LENGTH: 11
<212> TYPE: PRT
<213> ORGANISM: Artificial
<220> FEATURE:
<223> OTHER INFORMATION: Synthetic Peptide

<400> SEQUENCE: 416

Asp Arg Glu Gly Glu Asn Val Glu Gly Ile Glu
1               5                   10

<210> SEQ ID NO 417
<211> LENGTH: 11
<212> TYPE: PRT
<213> ORGANISM: Artificial
<220> FEATURE:
<223> OTHER INFORMATION: Synthetic Peptide

<400> SEQUENCE: 417

Asp Arg Glu Gly Glu Asn Val Ser Gly Ile Glu
1               5                   10

<210> SEQ ID NO 418
<211> LENGTH: 11
<212> TYPE: PRT
<213> ORGANISM: Artificial
<220> FEATURE:
<223> OTHER INFORMATION: Synthetic Peptide

<400> SEQUENCE: 418

Asp Arg Glu Gly Glu Asn Val Thr Gly Ile Glu
1               5                   10

<210> SEQ ID NO 419
<211> LENGTH: 11
<212> TYPE: PRT
<213> ORGANISM: Artificial
<220> FEATURE:
<223> OTHER INFORMATION: Synthetic Peptide

<400> SEQUENCE: 419

Asp Arg Glu Gly Ser Asn Val Tyr Gly Ile Glu
1               5                   10

<210> SEQ ID NO 420
```

```
<211> LENGTH: 11
<212> TYPE: PRT
<213> ORGANISM: Artificial
<220> FEATURE:
<223> OTHER INFORMATION: Synthetic Peptide

<400> SEQUENCE: 420

Asp Arg Glu Gly Ser Asn Val Asp Gly Ile Glu
1               5                   10

<210> SEQ ID NO 421
<211> LENGTH: 11
<212> TYPE: PRT
<213> ORGANISM: Artificial
<220> FEATURE:
<223> OTHER INFORMATION: Synthetic Peptide

<400> SEQUENCE: 421

Asp Arg Glu Gly Ser Asn Val Glu Gly Ile Glu
1               5                   10

<210> SEQ ID NO 422
<211> LENGTH: 11
<212> TYPE: PRT
<213> ORGANISM: Artificial
<220> FEATURE:
<223> OTHER INFORMATION: Synthetic Peptide

<400> SEQUENCE: 422

Asp Arg Glu Gly Ser Asn Val Ser Gly Ile Glu
1               5                   10

<210> SEQ ID NO 423
<211> LENGTH: 11
<212> TYPE: PRT
<213> ORGANISM: Artificial
<220> FEATURE:
<223> OTHER INFORMATION: Synthetic Peptide

<400> SEQUENCE: 423

Asp Arg Glu Gly Ser Asn Val Thr Gly Ile Glu
1               5                   10

<210> SEQ ID NO 424
<211> LENGTH: 11
<212> TYPE: PRT
<213> ORGANISM: Artificial
<220> FEATURE:
<223> OTHER INFORMATION: Synthetic Peptide

<400> SEQUENCE: 424

Asp Arg Glu Gly Thr Asn Val Tyr Gly Ile Glu
1               5                   10

<210> SEQ ID NO 425
<211> LENGTH: 11
<212> TYPE: PRT
<213> ORGANISM: Artificial
<220> FEATURE:
<223> OTHER INFORMATION: Synthetic Peptide

<400> SEQUENCE: 425

Asp Arg Glu Gly Thr Asn Val Asp Gly Ile Glu
1               5                   10

<210> SEQ ID NO 426
<211> LENGTH: 11
```

```
<212> TYPE: PRT
<213> ORGANISM: Artificial
<220> FEATURE:
<223> OTHER INFORMATION: Synthetic Peptide

<400> SEQUENCE: 426

Asp Arg Glu Gly Thr Asn Val Glu Gly Ile Glu
1               5                   10

<210> SEQ ID NO 427
<211> LENGTH: 11
<212> TYPE: PRT
<213> ORGANISM: Artificial
<220> FEATURE:
<223> OTHER INFORMATION: Synthetic Peptide

<400> SEQUENCE: 427

Asp Arg Glu Gly Thr Asn Val Ser Gly Ile Glu
1               5                   10

<210> SEQ ID NO 428
<211> LENGTH: 11
<212> TYPE: PRT
<213> ORGANISM: Artificial
<220> FEATURE:
<223> OTHER INFORMATION: Synthetic Peptide

<400> SEQUENCE: 428

Asp Arg Glu Gly Thr Asn Val Thr Gly Ile Glu
1               5                   10

<210> SEQ ID NO 429
<211> LENGTH: 11
<212> TYPE: PRT
<213> ORGANISM: Artificial
<220> FEATURE:
<223> OTHER INFORMATION: Synthetic Peptide

<400> SEQUENCE: 429

Glu Arg Glu Gly Tyr Asn Val Tyr Gly Ile Glu
1               5                   10

<210> SEQ ID NO 430
<211> LENGTH: 11
<212> TYPE: PRT
<213> ORGANISM: Artificial
<220> FEATURE:
<223> OTHER INFORMATION: Synthetic Peptide

<400> SEQUENCE: 430

Glu Arg Glu Gly Tyr Asn Val Asp Gly Ile Glu
1               5                   10

<210> SEQ ID NO 431
<211> LENGTH: 11
<212> TYPE: PRT
<213> ORGANISM: Artificial
<220> FEATURE:
<223> OTHER INFORMATION: Synthetic Peptide

<400> SEQUENCE: 431

Glu Arg Glu Gly Tyr Asn Val Glu Gly Ile Glu
1               5                   10

<210> SEQ ID NO 432
<211> LENGTH: 11
<212> TYPE: PRT
```

<213> ORGANISM: Artificial
<220> FEATURE:
<223> OTHER INFORMATION: Synthetic Peptide

<400> SEQUENCE: 432

Glu Arg Glu Gly Tyr Asn Val Ser Gly Ile Glu
1               5                   10

<210> SEQ ID NO 433
<211> LENGTH: 11
<212> TYPE: PRT
<213> ORGANISM: Artificial
<220> FEATURE:
<223> OTHER INFORMATION: Synthetic Peptide

<400> SEQUENCE: 433

Glu Arg Glu Gly Tyr Asn Val Thr Gly Ile Glu
1               5                   10

<210> SEQ ID NO 434
<211> LENGTH: 11
<212> TYPE: PRT
<213> ORGANISM: Artificial
<220> FEATURE:
<223> OTHER INFORMATION: Synthetic Peptide

<400> SEQUENCE: 434

Glu Arg Glu Gly Asp Asn Val Tyr Gly Ile Glu
1               5                   10

<210> SEQ ID NO 435
<211> LENGTH: 11
<212> TYPE: PRT
<213> ORGANISM: Artificial
<220> FEATURE:
<223> OTHER INFORMATION: Synthetic Peptide

<400> SEQUENCE: 435

Glu Arg Glu Gly Asp Asn Val Asp Gly Ile Glu
1               5                   10

<210> SEQ ID NO 436
<211> LENGTH: 11
<212> TYPE: PRT
<213> ORGANISM: Artificial
<220> FEATURE:
<223> OTHER INFORMATION: Synthetic Peptide

<400> SEQUENCE: 436

Glu Arg Glu Gly Asp Asn Val Glu Gly Ile Glu
1               5                   10

<210> SEQ ID NO 437
<211> LENGTH: 11
<212> TYPE: PRT
<213> ORGANISM: Artificial
<220> FEATURE:
<223> OTHER INFORMATION: Synthetic Peptide

<400> SEQUENCE: 437

Glu Arg Glu Gly Asp Asn Val Ser Gly Ile Glu
1               5                   10

<210> SEQ ID NO 438
<211> LENGTH: 11
<212> TYPE: PRT
<213> ORGANISM: Artificial

<220> FEATURE:
<223> OTHER INFORMATION: Synthetic Peptide

<400> SEQUENCE: 438

Glu Arg Glu Gly Asp Asn Val Thr Gly Ile Glu
1               5                   10

<210> SEQ ID NO 439
<211> LENGTH: 11
<212> TYPE: PRT
<213> ORGANISM: Artificial
<220> FEATURE:
<223> OTHER INFORMATION: Synthetic Peptide

<400> SEQUENCE: 439

Glu Arg Glu Gly Glu Asn Val Tyr Gly Ile Glu
1               5                   10

<210> SEQ ID NO 440
<211> LENGTH: 11
<212> TYPE: PRT
<213> ORGANISM: Artificial
<220> FEATURE:
<223> OTHER INFORMATION: Synthetic Peptide

<400> SEQUENCE: 440

Glu Arg Glu Gly Glu Asn Val Asp Gly Ile Glu
1               5                   10

<210> SEQ ID NO 441
<211> LENGTH: 11
<212> TYPE: PRT
<213> ORGANISM: Artificial
<220> FEATURE:
<223> OTHER INFORMATION: Synthetic Peptide

<400> SEQUENCE: 441

Glu Arg Glu Gly Glu Asn Val Glu Gly Ile Glu
1               5                   10

<210> SEQ ID NO 442
<211> LENGTH: 11
<212> TYPE: PRT
<213> ORGANISM: Artificial
<220> FEATURE:
<223> OTHER INFORMATION: Synthetic Peptide

<400> SEQUENCE: 442

Glu Arg Glu Gly Glu Asn Val Ser Gly Ile Glu
1               5                   10

<210> SEQ ID NO 443
<211> LENGTH: 11
<212> TYPE: PRT
<213> ORGANISM: Artificial
<220> FEATURE:
<223> OTHER INFORMATION: Synthetic Peptide

<400> SEQUENCE: 443

Glu Arg Glu Gly Glu Asn Val Thr Gly Ile Glu
1               5                   10

<210> SEQ ID NO 444
<211> LENGTH: 11
<212> TYPE: PRT
<213> ORGANISM: Artificial
<220> FEATURE:

<223> OTHER INFORMATION: Synthetic Peptide

<400> SEQUENCE: 444

Glu Arg Glu Gly Ser Asn Val Tyr Gly Ile Glu
1               5                   10

<210> SEQ ID NO 445
<211> LENGTH: 11
<212> TYPE: PRT
<213> ORGANISM: Artificial
<220> FEATURE:
<223> OTHER INFORMATION: Synthetic Peptide

<400> SEQUENCE: 445

Glu Arg Glu Gly Ser Asn Val Asp Gly Ile Glu
1               5                   10

<210> SEQ ID NO 446
<211> LENGTH: 11
<212> TYPE: PRT
<213> ORGANISM: Artificial
<220> FEATURE:
<223> OTHER INFORMATION: Synthetic Peptide

<400> SEQUENCE: 446

Glu Arg Glu Gly Ser Asn Val Glu Gly Ile Glu
1               5                   10

<210> SEQ ID NO 447
<211> LENGTH: 11
<212> TYPE: PRT
<213> ORGANISM: Artificial
<220> FEATURE:
<223> OTHER INFORMATION: Synthetic Peptide

<400> SEQUENCE: 447

Glu Arg Glu Gly Ser Asn Val Ser Gly Ile Glu
1               5                   10

<210> SEQ ID NO 448
<211> LENGTH: 11
<212> TYPE: PRT
<213> ORGANISM: Artificial
<220> FEATURE:
<223> OTHER INFORMATION: Synthetic Peptide

<400> SEQUENCE: 448

Glu Arg Glu Gly Ser Asn Val Thr Gly Ile Glu
1               5                   10

<210> SEQ ID NO 449
<211> LENGTH: 11
<212> TYPE: PRT
<213> ORGANISM: Artificial
<220> FEATURE:
<223> OTHER INFORMATION: Synthetic Peptide

<400> SEQUENCE: 449

Glu Arg Glu Gly Thr Asn Val Tyr Gly Ile Glu
1               5                   10

<210> SEQ ID NO 450
<211> LENGTH: 11
<212> TYPE: PRT
<213> ORGANISM: Artificial
<220> FEATURE:
<223> OTHER INFORMATION: Synthetic Peptide

<400> SEQUENCE: 450

Glu Arg Glu Gly Thr Asn Val Asp Gly Ile Glu
1               5                   10

<210> SEQ ID NO 451
<211> LENGTH: 11
<212> TYPE: PRT
<213> ORGANISM: Artificial
<220> FEATURE:
<223> OTHER INFORMATION: Synthetic Peptide

<400> SEQUENCE: 451

Glu Arg Glu Gly Thr Asn Val Glu Gly Ile Glu
1               5                   10

<210> SEQ ID NO 452
<211> LENGTH: 11
<212> TYPE: PRT
<213> ORGANISM: Artificial
<220> FEATURE:
<223> OTHER INFORMATION: Synthetic Peptide

<400> SEQUENCE: 452

Glu Arg Glu Gly Thr Asn Val Ser Gly Ile Glu
1               5                   10

<210> SEQ ID NO 453
<211> LENGTH: 11
<212> TYPE: PRT
<213> ORGANISM: Artificial
<220> FEATURE:
<223> OTHER INFORMATION: Synthetic Peptide

<400> SEQUENCE: 453

Glu Arg Glu Gly Thr Asn Val Thr Gly Ile Glu
1               5                   10

<210> SEQ ID NO 454
<211> LENGTH: 11
<212> TYPE: PRT
<213> ORGANISM: Artificial
<220> FEATURE:
<223> OTHER INFORMATION: Synthetic Peptide

<400> SEQUENCE: 454

Ser Arg Glu Gly Tyr Asn Val Tyr Gly Ile Glu
1               5                   10

<210> SEQ ID NO 455
<211> LENGTH: 11
<212> TYPE: PRT
<213> ORGANISM: Artificial
<220> FEATURE:
<223> OTHER INFORMATION: Synthetic Peptide

<400> SEQUENCE: 455

Ser Arg Glu Gly Tyr Asn Val Asp Gly Ile Glu
1               5                   10

<210> SEQ ID NO 456
<211> LENGTH: 11
<212> TYPE: PRT
<213> ORGANISM: Artificial
<220> FEATURE:
<223> OTHER INFORMATION: Synthetic Peptide

```
<400> SEQUENCE: 456

Ser Arg Glu Gly Tyr Asn Val Glu Gly Ile Glu
1               5                   10

<210> SEQ ID NO 457
<211> LENGTH: 11
<212> TYPE: PRT
<213> ORGANISM: Artificial
<220> FEATURE:
<223> OTHER INFORMATION: Synthetic Peptide

<400> SEQUENCE: 457

Ser Arg Glu Gly Tyr Asn Val Ser Gly Ile Glu
1               5                   10

<210> SEQ ID NO 458
<211> LENGTH: 11
<212> TYPE: PRT
<213> ORGANISM: Artificial
<220> FEATURE:
<223> OTHER INFORMATION: Synthetic Peptide

<400> SEQUENCE: 458

Ser Arg Glu Gly Tyr Asn Val Thr Gly Ile Glu
1               5                   10

<210> SEQ ID NO 459
<211> LENGTH: 11
<212> TYPE: PRT
<213> ORGANISM: Artificial
<220> FEATURE:
<223> OTHER INFORMATION: Synthetic Peptide

<400> SEQUENCE: 459

Ser Arg Glu Gly Asp Asn Val Tyr Gly Ile Glu
1               5                   10

<210> SEQ ID NO 460
<211> LENGTH: 11
<212> TYPE: PRT
<213> ORGANISM: Artificial
<220> FEATURE:
<223> OTHER INFORMATION: Synthetic Peptide

<400> SEQUENCE: 460

Ser Arg Glu Gly Asp Asn Val Asp Gly Ile Glu
1               5                   10

<210> SEQ ID NO 461
<211> LENGTH: 11
<212> TYPE: PRT
<213> ORGANISM: Artificial
<220> FEATURE:
<223> OTHER INFORMATION: Synthetic Peptide

<400> SEQUENCE: 461

Ser Arg Glu Gly Asp Asn Val Glu Gly Ile Glu
1               5                   10

<210> SEQ ID NO 462
<211> LENGTH: 11
<212> TYPE: PRT
<213> ORGANISM: Artificial
<220> FEATURE:
<223> OTHER INFORMATION: Synthetic Peptide

<400> SEQUENCE: 462
```

```
Ser Arg Glu Gly Asp Asn Val Ser Gly Ile Glu
1               5                   10

<210> SEQ ID NO 463
<211> LENGTH: 11
<212> TYPE: PRT
<213> ORGANISM: Artificial
<220> FEATURE:
<223> OTHER INFORMATION: Synthetic Peptide

<400> SEQUENCE: 463

Ser Arg Glu Gly Asp Asn Val Thr Gly Ile Glu
1               5                   10

<210> SEQ ID NO 464
<211> LENGTH: 11
<212> TYPE: PRT
<213> ORGANISM: Artificial
<220> FEATURE:
<223> OTHER INFORMATION: Synthetic Peptide

<400> SEQUENCE: 464

Ser Arg Glu Gly Glu Asn Val Tyr Gly Ile Glu
1               5                   10

<210> SEQ ID NO 465
<211> LENGTH: 11
<212> TYPE: PRT
<213> ORGANISM: Artificial
<220> FEATURE:
<223> OTHER INFORMATION: Synthetic Peptide

<400> SEQUENCE: 465

Ser Arg Glu Gly Glu Asn Val Asp Gly Ile Glu
1               5                   10

<210> SEQ ID NO 466
<211> LENGTH: 11
<212> TYPE: PRT
<213> ORGANISM: Artificial
<220> FEATURE:
<223> OTHER INFORMATION: Synthetic Peptide

<400> SEQUENCE: 466

Ser Arg Glu Gly Glu Asn Val Glu Gly Ile Glu
1               5                   10

<210> SEQ ID NO 467
<211> LENGTH: 11
<212> TYPE: PRT
<213> ORGANISM: Artificial
<220> FEATURE:
<223> OTHER INFORMATION: Synthetic Peptide

<400> SEQUENCE: 467

Ser Arg Glu Gly Glu Asn Val Ser Gly Ile Glu
1               5                   10

<210> SEQ ID NO 468
<211> LENGTH: 11
<212> TYPE: PRT
<213> ORGANISM: Artificial
<220> FEATURE:
<223> OTHER INFORMATION: Synthetic Peptide

<400> SEQUENCE: 468
```

Ser Arg Glu Gly Glu Asn Val Thr Gly Ile Glu
1               5                   10

<210> SEQ ID NO 469
<211> LENGTH: 11
<212> TYPE: PRT
<213> ORGANISM: Artificial
<220> FEATURE:
<223> OTHER INFORMATION: Synthetic Peptide

<400> SEQUENCE: 469

Ser Arg Glu Gly Ser Asn Val Tyr Gly Ile Glu
1               5                   10

<210> SEQ ID NO 470
<211> LENGTH: 11
<212> TYPE: PRT
<213> ORGANISM: Artificial
<220> FEATURE:
<223> OTHER INFORMATION: Synthetic Peptide

<400> SEQUENCE: 470

Ser Arg Glu Gly Ser Asn Val Asp Gly Ile Glu
1               5                   10

<210> SEQ ID NO 471
<211> LENGTH: 11
<212> TYPE: PRT
<213> ORGANISM: Artificial
<220> FEATURE:
<223> OTHER INFORMATION: Synthetic Peptide

<400> SEQUENCE: 471

Ser Arg Glu Gly Ser Asn Val Glu Gly Ile Glu
1               5                   10

<210> SEQ ID NO 472
<211> LENGTH: 11
<212> TYPE: PRT
<213> ORGANISM: Artificial
<220> FEATURE:
<223> OTHER INFORMATION: Synthetic Peptide

<400> SEQUENCE: 472

Ser Arg Glu Gly Ser Asn Val Ser Gly Ile Glu
1               5                   10

<210> SEQ ID NO 473
<211> LENGTH: 11
<212> TYPE: PRT
<213> ORGANISM: Artificial
<220> FEATURE:
<223> OTHER INFORMATION: Synthetic Peptide

<400> SEQUENCE: 473

Ser Arg Glu Gly Ser Asn Val Thr Gly Ile Glu
1               5                   10

<210> SEQ ID NO 474
<211> LENGTH: 11
<212> TYPE: PRT
<213> ORGANISM: Artificial
<220> FEATURE:
<223> OTHER INFORMATION: Synthetic Peptide

<400> SEQUENCE: 474

Ser Arg Glu Gly Thr Asn Val Tyr Gly Ile Glu

```
1               5                   10
```

<210> SEQ ID NO 475
<211> LENGTH: 11
<212> TYPE: PRT
<213> ORGANISM: Artificial
<220> FEATURE:
<223> OTHER INFORMATION: Synthetic Peptide

<400> SEQUENCE: 475

```
Ser Arg Glu Gly Thr Asn Val Asp Gly Ile Glu
1               5                   10
```

<210> SEQ ID NO 476
<211> LENGTH: 11
<212> TYPE: PRT
<213> ORGANISM: Artificial
<220> FEATURE:
<223> OTHER INFORMATION: Synthetic Peptide

<400> SEQUENCE: 476

```
Ser Arg Glu Gly Thr Asn Val Glu Gly Ile Glu
1               5                   10
```

<210> SEQ ID NO 477
<211> LENGTH: 11
<212> TYPE: PRT
<213> ORGANISM: Artificial
<220> FEATURE:
<223> OTHER INFORMATION: Synthetic Peptide

<400> SEQUENCE: 477

```
Ser Arg Glu Gly Thr Asn Val Ser Gly Ile Glu
1               5                   10
```

<210> SEQ ID NO 478
<211> LENGTH: 11
<212> TYPE: PRT
<213> ORGANISM: Artificial
<220> FEATURE:
<223> OTHER INFORMATION: Synthetic Peptide

<400> SEQUENCE: 478

```
Ser Arg Glu Gly Thr Asn Val Thr Gly Ile Glu
1               5                   10
```

<210> SEQ ID NO 479
<211> LENGTH: 11
<212> TYPE: PRT
<213> ORGANISM: Artificial
<220> FEATURE:
<223> OTHER INFORMATION: Synthetic Peptide

<400> SEQUENCE: 479

```
Thr Arg Glu Gly Tyr Asn Val Tyr Gly Ile Glu
1               5                   10
```

<210> SEQ ID NO 480
<211> LENGTH: 11
<212> TYPE: PRT
<213> ORGANISM: Artificial
<220> FEATURE:
<223> OTHER INFORMATION: Synthetic Peptide

<400> SEQUENCE: 480

```
Thr Arg Glu Gly Tyr Asn Val Asp Gly Ile Glu
1               5                   10
```

```
<210> SEQ ID NO 481
<211> LENGTH: 11
<212> TYPE: PRT
<213> ORGANISM: Artificial
<220> FEATURE:
<223> OTHER INFORMATION: Synthetic Peptide

<400> SEQUENCE: 481

Thr Arg Glu Gly Tyr Asn Val Glu Gly Ile Glu
1               5                   10

<210> SEQ ID NO 482
<211> LENGTH: 11
<212> TYPE: PRT
<213> ORGANISM: Artificial
<220> FEATURE:
<223> OTHER INFORMATION: Synthetic Peptide

<400> SEQUENCE: 482

Thr Arg Glu Gly Tyr Asn Val Ser Gly Ile Glu
1               5                   10

<210> SEQ ID NO 483
<211> LENGTH: 11
<212> TYPE: PRT
<213> ORGANISM: Artificial
<220> FEATURE:
<223> OTHER INFORMATION: Synthetic Peptide

<400> SEQUENCE: 483

Thr Arg Glu Gly Tyr Asn Val Thr Gly Ile Glu
1               5                   10

<210> SEQ ID NO 484
<211> LENGTH: 11
<212> TYPE: PRT
<213> ORGANISM: Artificial
<220> FEATURE:
<223> OTHER INFORMATION: Synthetic Peptide

<400> SEQUENCE: 484

Thr Arg Glu Gly Asp Asn Val Tyr Gly Ile Glu
1               5                   10

<210> SEQ ID NO 485
<211> LENGTH: 11
<212> TYPE: PRT
<213> ORGANISM: Artificial
<220> FEATURE:
<223> OTHER INFORMATION: Synthetic Peptide

<400> SEQUENCE: 485

Thr Arg Glu Gly Asp Asn Val Asp Gly Ile Glu
1               5                   10

<210> SEQ ID NO 486
<211> LENGTH: 11
<212> TYPE: PRT
<213> ORGANISM: Artificial
<220> FEATURE:
<223> OTHER INFORMATION: Synthetic Peptide

<400> SEQUENCE: 486

Thr Arg Glu Gly Asp Asn Val Glu Gly Ile Glu
1               5                   10
```

```
<210> SEQ ID NO 487
<211> LENGTH: 11
<212> TYPE: PRT
<213> ORGANISM: Artificial
<220> FEATURE:
<223> OTHER INFORMATION: Synthetic Peptide

<400> SEQUENCE: 487

Thr Arg Glu Gly Asp Asn Val Ser Gly Ile Glu
1               5                   10

<210> SEQ ID NO 488
<211> LENGTH: 11
<212> TYPE: PRT
<213> ORGANISM: Artificial
<220> FEATURE:
<223> OTHER INFORMATION: Synthetic Peptide

<400> SEQUENCE: 488

Thr Arg Glu Gly Asp Asn Val Thr Gly Ile Glu
1               5                   10

<210> SEQ ID NO 489
<211> LENGTH: 11
<212> TYPE: PRT
<213> ORGANISM: Artificial
<220> FEATURE:
<223> OTHER INFORMATION: Synthetic Peptide

<400> SEQUENCE: 489

Thr Arg Glu Gly Glu Asn Val Tyr Gly Ile Glu
1               5                   10

<210> SEQ ID NO 490
<211> LENGTH: 11
<212> TYPE: PRT
<213> ORGANISM: Artificial
<220> FEATURE:
<223> OTHER INFORMATION: Synthetic Peptide

<400> SEQUENCE: 490

Thr Arg Glu Gly Glu Asn Val Asp Gly Ile Glu
1               5                   10

<210> SEQ ID NO 491
<211> LENGTH: 11
<212> TYPE: PRT
<213> ORGANISM: Artificial
<220> FEATURE:
<223> OTHER INFORMATION: Synthetic Peptide

<400> SEQUENCE: 491

Thr Arg Glu Gly Glu Asn Val Glu Gly Ile Glu
1               5                   10

<210> SEQ ID NO 492
<211> LENGTH: 11
<212> TYPE: PRT
<213> ORGANISM: Artificial
<220> FEATURE:
<223> OTHER INFORMATION: Synthetic Peptide

<400> SEQUENCE: 492

Thr Arg Glu Gly Glu Asn Val Ser Gly Ile Glu
1               5                   10
```

```
<210> SEQ ID NO 493
<211> LENGTH: 11
<212> TYPE: PRT
<213> ORGANISM: Artificial
<220> FEATURE:
<223> OTHER INFORMATION: Synthetic Peptide

<400> SEQUENCE: 493

Thr Arg Glu Gly Glu Asn Val Thr Gly Ile Glu
1               5                   10

<210> SEQ ID NO 494
<211> LENGTH: 11
<212> TYPE: PRT
<213> ORGANISM: Artificial
<220> FEATURE:
<223> OTHER INFORMATION: Synthetic Peptide

<400> SEQUENCE: 494

Thr Arg Glu Gly Ser Asn Val Tyr Gly Ile Glu
1               5                   10

<210> SEQ ID NO 495
<211> LENGTH: 11
<212> TYPE: PRT
<213> ORGANISM: Artificial
<220> FEATURE:
<223> OTHER INFORMATION: Synthetic Peptide

<400> SEQUENCE: 495

Thr Arg Glu Gly Ser Asn Val Asp Gly Ile Glu
1               5                   10

<210> SEQ ID NO 496
<211> LENGTH: 11
<212> TYPE: PRT
<213> ORGANISM: Artificial
<220> FEATURE:
<223> OTHER INFORMATION: Synthetic Peptide

<400> SEQUENCE: 496

Thr Arg Glu Gly Ser Asn Val Glu Gly Ile Glu
1               5                   10

<210> SEQ ID NO 497
<211> LENGTH: 11
<212> TYPE: PRT
<213> ORGANISM: Artificial
<220> FEATURE:
<223> OTHER INFORMATION: Synthetic Peptide

<400> SEQUENCE: 497

Thr Arg Glu Gly Ser Asn Val Ser Gly Ile Glu
1               5                   10

<210> SEQ ID NO 498
<211> LENGTH: 11
<212> TYPE: PRT
<213> ORGANISM: Artificial
<220> FEATURE:
<223> OTHER INFORMATION: Synthetic Peptide

<400> SEQUENCE: 498

Thr Arg Glu Gly Ser Asn Val Thr Gly Ile Glu
1               5                   10

<210> SEQ ID NO 499
```

```
<211> LENGTH: 11
<212> TYPE: PRT
<213> ORGANISM: Artificial
<220> FEATURE:
<223> OTHER INFORMATION: Synthetic Peptide

<400> SEQUENCE: 499

Thr Arg Glu Gly Thr Asn Val Tyr Gly Ile Glu
1               5                   10

<210> SEQ ID NO 500
<211> LENGTH: 11
<212> TYPE: PRT
<213> ORGANISM: Artificial
<220> FEATURE:
<223> OTHER INFORMATION: Synthetic Peptide

<400> SEQUENCE: 500

Thr Arg Glu Gly Thr Asn Val Asp Gly Ile Glu
1               5                   10

<210> SEQ ID NO 501
<211> LENGTH: 11
<212> TYPE: PRT
<213> ORGANISM: Artificial
<220> FEATURE:
<223> OTHER INFORMATION: Synthetic Peptide

<400> SEQUENCE: 501

Thr Arg Glu Gly Thr Asn Val Glu Gly Ile Glu
1               5                   10

<210> SEQ ID NO 502
<211> LENGTH: 11
<212> TYPE: PRT
<213> ORGANISM: Artificial
<220> FEATURE:
<223> OTHER INFORMATION: Synthetic Peptide

<400> SEQUENCE: 502

Thr Arg Glu Gly Thr Asn Val Ser Gly Ile Glu
1               5                   10

<210> SEQ ID NO 503
<211> LENGTH: 11
<212> TYPE: PRT
<213> ORGANISM: Artificial
<220> FEATURE:
<223> OTHER INFORMATION: Synthetic Peptide

<400> SEQUENCE: 503

Thr Arg Glu Gly Thr Asn Val Thr Gly Ile Glu
1               5                   10

<210> SEQ ID NO 504
<211> LENGTH: 22
<212> TYPE: PRT
<213> ORGANISM: Artificial
<220> FEATURE:
<223> OTHER INFORMATION: Synthetic Peptide

<400> SEQUENCE: 504

Tyr Gly Arg Lys Lys Arg Arg Gln Arg Arg Tyr Lys Glu Gly Tyr
1               5                   10                  15

Asn Val Tyr Gly Ile Glu
            20
```

<210> SEQ ID NO 505
<211> LENGTH: 22
<212> TYPE: PRT
<213> ORGANISM: Artificial
<220> FEATURE:
<223> OTHER INFORMATION: Synthetic Peptide

<400> SEQUENCE: 505

Tyr Gly Arg Lys Lys Arg Arg Gln Arg Arg Arg Ala Lys Glu Gly Ala
1               5                   10                  15

Asn Val Ala Gly Ile Glu
            20

<210> SEQ ID NO 506
<211> LENGTH: 40
<212> TYPE: PRT
<213> ORGANISM: Artificial
<220> FEATURE:
<223> OTHER INFORMATION: Mutant HA-GluR2 delta 834-843

<400> SEQUENCE: 506

Lys Arg Met Lys Val Ala Lys Asn Pro Gln Asn Ile Asn Pro Ser Ser
1               5                   10                  15

Ser Gln Asn Ser Gln Asn Phe Ala Thr Tyr Lys Glu Gly Tyr Asn Val
            20                  25                  30

Tyr Gly Ile Glu Ser Val Lys Ile
        35                  40

<210> SEQ ID NO 507
<211> LENGTH: 41
<212> TYPE: PRT
<213> ORGANISM: Artificial
<220> FEATURE:
<223> OTHER INFORMATION: Mutant HA-GluR2 delta 844-853

<400> SEQUENCE: 507

Ile Glu Phe Cys Tyr Lys Ser Arg Ala Glu Ala Asn Ile Asn Pro Ser
1               5                   10                  15

Ser Ser Gln Asn Ser Gln Asn Phe Ala Thr Tyr Lys Glu Gly Thr Asn
            20                  25                  30

Val Tyr Gly Ile Glu Ser Val Lys Ile
        35                  40

<210> SEQ ID NO 508
<211> LENGTH: 21
<212> TYPE: PRT
<213> ORGANISM: Artificial
<220> FEATURE:
<223> OTHER INFORMATION: Mutant GluR2 delta 854

<400> SEQUENCE: 508

Ile Glu Phe Cys Tyr Lys Ser Arg Ala Glu Ala Lys Arg Met Lys Val
1               5                   10                  15

Ala Lys Asn Pro Gln
            20

<210> SEQ ID NO 509
<211> LENGTH: 36
<212> TYPE: PRT
<213> ORGANISM: Artificial
<220> FEATURE:
<223> OTHER INFORMATION: Mutant HA-GluR2 delta 869

<400> SEQUENCE: 509

```
Ile Glu Phe Cys Tyr Lys Ser Arg Ala Glu Ala Lys Arg Met Lys Val
1               5                   10                  15

Ala Lys Asn Pro Gln Asn Ile Asn Pro Ser Ser Ser Gln Asn Ser Gln
                20              25                  30

Asn Phe Ala Thr
            35

<210> SEQ ID NO 510
<211> LENGTH: 47
<212> TYPE: PRT
<213> ORGANISM: Artificial
<220> FEATURE:
<223> OTHER INFORMATION: Mutant HA-GluR2 delta 880

<400> SEQUENCE: 510

Ile Glu Phe Cys Tyr Lys Ser Arg Ala Glu Ala Lys Arg Met Lys Val
1               5                   10                  15

Ala Lys Asn Pro Gln Asn Ile Asn Pro Ser Ser Ser Gln Asn Ser Gln
                20              25                  30

Asn Phe Ala Thr Tyr Lys Glu Gly Tyr Asn Val Tyr Gly Ile Glu
            35              40                  45
```

METHODS FOR MODULATING NEURONAL RESPONSES

CROSS REFERENCES TO RELATED APPLICATIONS

This application is a continuation of and claims the priority benefit of U.S. Continuation patent application Ser. No. 11/399,840, filed Apr. 6, 2006, PCT patent application Serial No. PCT/CA2004/001813 (WO 2005/03311 A2) filed Oct. 8, 2004, and U.S. Provisional Application No. 60/509,249, filed Oct. 8, 2004, the disclosures of which priority instruments are incorporated herein by reference in their entirety.

FIELD OF THE INVENTION

The invention is, in general, in the field of neurology. More specifically, the invention provides, in part, methods and reagents for modulating neuronal apoptosis or synaptic plasticity.

BACKGROUND OF THE INVENTION

Synaptic transmission is the process by which neurons communicate by excitatory (generation of an action potential) or inhibitory (inhibition of an action potential following excitation) mechanisms. Excitatory synaptic transmission often occurs by means of the neurotransmitter L-glutamate and its cognate glutamate receptors, which include the N-methyl-D-aspartate (NMDA) and α-amino-3-hydroxy-5-methylisoxazole-4-propionic acid (AMPA) subtype glutamate receptors. Synaptic plasticity refers to the use-dependent ability of post-synaptic neurons to modulate their response to the release of neurotransmitters during synaptic transmission, and is thought to be important in learning and memory processes.

The excessive stimulation of post-synaptic neurons (a phenomenon known as "excitotoxicity"), which can lead to neuronal death or apoptosis, has been implicated in a variety of central nervous system (CNS) disorders. Activation of the NMDA receptor may induce programmed cell death (apoptosis) in cultured hippocampal neurons, and may underlie the loss of neurons and neuronal function in central nervous system disorders ranging from acute brain trauma and stroke to neurodegenerative diseases such as Huntington's, Alzheimer's, and Parkinson's Diseases.[1-5]

NMDA receptor activation may also lead to facilitation of clathrin-mediated endocytosis of AMPA receptors, which mediate fast synaptic transmission at excitatory synapses in the mammalian CNS.[6;7] AMPA receptor function can be modified at the level of open channel probability[34], channel conductance[27;33], and the kinetics of desensitization.[52] Rapid redistribution of AMPA receptors to and from the postsynaptic domain is also thought to be a means of regulating the strength of AMPA receptor-mediated synaptic transmission.[43;45;6] AMPA receptors undergo functionally distinct constitutive and regulated clathrin-dependent cycling between intracellular compartments and the plasma membrane via vesicle-mediated plasma membrane insertion (exocytosis) and internalization (endocytosis).[22;30;20;24;41;14] Regulating these processes can lead to rapid changes in the number of AMPA receptors expressed in the postsynaptic membrane, thereby contributing to the expression of certain forms of synaptic plasticity, including hippocampal long term potentiation (LTP)[35;42;50] and long term depression (LTD) in the cerebellum and hippocampus.[14;24;25;44] AMPA receptors may be subjected to stimulated endocytosis by diverse stimuli including growth factors, such as insulin/IGF-1[14;25], agonist binding[22;21;20] and LTD-producing protocols.[24;14;25]

SUMMARY OF THE INVENTION

The invention provides, in part, methods and reagents for modulating neuronal apoptosis. The invention also provides, in part, methods and reagents for modulating synaptic plasticity.

In some aspects, the invention provides a method of modulating NMDA-mediated neuronal apoptosis by contacting a neuronal cell with an inhibitor of AMPA receptor endocytosis. In alternative aspects, the invention provides a method of modulating NMDA-mediated neuronal apoptosis by contacting a neuronal cell with an inhibitor of clathrin-mediated endocytosis. In alternative aspects, the invention provides a method of treating or preventing neurological damage or dysfunction in a subject by administering an effective amount of an inhibitor of AMPA receptor endocytosis to the subject.

In alternative embodiments, the neurological damage may include NMDA-induced neuronal apoptosis, or may occur as a result of excessive activation of NMDA receptors or due to changes in AMPA receptor endocytosis, or may occur as a result of at least one of a disorder selected from the group consisting of stress, anxiety, depression, hypoglycemia, cardiac arrest, epilepsy, cerebral ischemia, brain trauma, Alzheimer's disease, Parkinson's disease, Huntington's disease; neuropathic pain; amyotrophic lateral sclerosis (ALS); Hutchinson Gilford syndrome; diabetes; ataxia; mental retardation; dementias, disorders associated with smoking or obesity, high blood pressure, disorders associated with defects or dysfunction in learning or memory, psychiatric disorders, autism, schizophrenia, fragile X syndrome, or disorders associated with substance abuse or addiction to a drug (e.g., nicotine, alcohol, opiates, heroin, codeine, morphine pethidine, methadone, marijuana, phenyclidene, psychostimulants, amphetamines, cocaine, barbiturates, pentobarbitone, quinalbarbitone, benzodiazepines, temazepam, diazepam or flunitrazepam).

In alternative aspects, the invention provides a method of modulating synaptic plasticity in a subject by administering an effective amount of an inhibitor of AMPA receptor endocytosis to the subject (e.g., a normal subject i.e. one not having or not diagnosed with neurological damage or dysfunction). In alternative embodiments, the method may further include enhancing synaptic plasticity. In alternative aspects, the invention provides a method of treating or preventing substance abuse in a subject by administering an effective amount of an inhibitor of AMPA receptor endocytosis to the subject.

In some aspects, the invention provides a method of modulating AMPA receptor endocytosis by contacting a cell or system (for example, a lipid vehicle) expressing an AMPA receptor with a peptide comprising an amino acid sequence selected from the group consisting of YREGYNVYGIE (SEQ ID NO. 1), YKEGYNVYGIE (SEQ ID NO. 2), YREGYNVYG (SEQ ID NO. 3), or YKEGYNVYG (SEQ ID NO. 4), or with an antibody that specifically binds an amino acid sequence selected from the group consisting of YREGYNVYGIE (SEQ ID NO. 1), YKEGYNVYGIE (SEQ ID NO. 2), YREGYNVYG (SEQ ID NO. 3), and YKEGYNVYG (SEQ ID NO. 4).

In some aspects, the invention provides a method of modulating AMPA receptor endocytosis, by contacting a cell expressing an AMPA receptor with a modulatory compound comprising the amino acid sequence set forth in Table I or conservative substitutions thereof, Formula I, or Formula A, or homologous sequences thereto found in the C-terminus of the GluR2, GluR3, or GluR4 subunits of the AMPA receptor or a fragment or variant thereof, or comprising an antibody that specifically binds the amino acid sequence set forth in Table I or conservative substitutions thereof, Formula I, or Formula A, or homologous sequences thereto found in the C-terminus of the GluR2, GluR3, or GluR4 subunits of the AMPA receptor.

In alternative aspects, the invention provides a method of screening for a modulator of AMPA receptor endocytosis, by providing a system including an AMPA receptor polypeptide or a biologically-active fragment thereof; an inhibitor of AMPA receptor endocytosis; providing a test compound; contacting the system with the test compound; and determining whether the test compound modulates AMPA receptor endocytosis.

In alternative aspects, the invention provides a method of screening for a modulator of AMPA receptor endocytosis, the method including providing an AMPA receptor polypeptide or a biologically-active fragment thereof; providing an inhibitor of AMPA receptor endocytosis; providing a test compound; contacting the AMPA receptor polypeptide or a biologically-active fragment thereof with the test compound or the inhibitor; and determining whether the test compound modulates AMPA receptor endocytosis.

In alternative aspects, the invention provides a method of screening for a modulator of AMPA receptor endocytosis, by providing an AMPA receptor polypeptide or a biologically-active fragment thereof; providing a test compound; contacting the AMPA receptor polypeptide or a biologically-active fragment thereof with the test compound; and determining whether the test compound modulates AMPA receptor endocytosis. In alternative embodiments, the method may further include providing an inhibitor of AMPA receptor endocytosis, contacting the AMPA receptor polypeptide or a biologically-active fragment thereof with the inhibitor, and determining whether the test compound modulates AMPA receptor endocytosis when compared to the inhibitor. In alternative aspects, the invention provides a polypeptide including an amino acid sequence substantially identical to the sequence of YREGYNVYGIE (SEQ ID NO. 1), YKEGYNVYGIE (SEQ ID NO. 2), YREGYNVYG (SEQ ID NO. 3), or YKEGYNVYG (SEQ ID NO. 4), or a nucleic acid molecule encoding any of these amino acid sequences, or an antibody that specifically binds any of these amino acid sequences.

In alternative aspects, the invention provides a substantially pure compound including Formula I: $Z_1$-$X_1$-$X_2$-E-G-$X_3$-N-V-$X_4$-G-$Z_2$; where $X_1$ may be Y, D, E, S, or T; $X_2$ may be K or R; $X_3$ is Y, D, E, S, or T; $X_4$ may be Y, D, E, S, or T; $Z_1$ may be $H_2N-$, RHN— or, RRN—; $Z_2$ may be —C(O)OH, —C(O)R, —C(O)OR, —C(O)NHR, —C(O)NRR; R at each occurrence may be independently selected from $(C_1$-$C_6)$ alkyl, $(C_1$-$C_6)$ alkenyl, $(C_1$-$C_6)$ alkynyl, substituted $(C_1$-$C_6)$ alkyl, substituted $(C_1$-$C_6)$ alkenyl, or substituted $(C_1$-$C_6)$ alkynyl; wherein "-" may be a covalent linkage, and wherein the compound may be an inhibitor of AMP A receptor endocytosis. In alternative embodiments, anyone or more of $X_1$, $X_3$, or $X_4$ may be a Y.

In alternative aspects, the invention provides a substantially pure compound including Formula A: $Z_1$-$X_1$-$X_2$-$X_3$-$X_4$-$X_5$-$X_6$-$X_7$-$X_8$-$X_9$-$Z_2$, where $X_1$ may be an amino acid having a hydropathic index of −0.3 to −4.3 or of −1.3 to −3.3 or may be a neutral or an acidic amino acid, or may Gly, Ser, Thr, Cys, Asn, Gln, Tyr, Asp, Glu; $X_2$ may be an amino acid having a hydropathic index of +1.0 to +5.0 or of +2.0 to +4.0 or may be a basic amino acid or may be Lys, Arg, His; $X_3$ may be an amino acid having a hydropathic index of +1.0 to +5.0 or of +2.0 to +4.0 or may be an acidic amino acid or may be Asp, Glu; $X_4$ may be an amino acid having a hydropathic index of −2.0 to +2.0 or of −1.0 to +1.0 to or may be a neutral amino acid or may be Gly, Ser, Thr, Cys, Asn, Gln, Tyr; $X_5$ may be an amino acid having a hydropathic index of −0.3 to −4.3 or of −1.3 to −3.3 or may be a neutral or an acidic amino acid or may be Gly, Ser, Thr, Cys, Asn, Gln, Tyr, Asp, Glu; $X_6$ may be an amino acid having a hydropathic index of −1.8 to +2.2 or of −0.8 to +1.2 or may be a neutral amino acid or may be Gly, Ser, Thr, Cys, Asn, Gln, Tyr; $X_7$ may be an amino acid having a hydropathic index of −3.5 to 0.5 or of −2.5 to −0.5 or 15 may be a non-polar amino acid or may be Ala, Val, Leu, Ile, Phe, Trp, Pro, Met; $X_8$ may be an amino acid having a hydropathic index of −0.3 to −4.3 or of −1.3 to −3.3 or may be a neutral or an acidic amino acid or may be Gly, Ser, Thr, Cys, Asn, Gln, Tyr, Asp, Glu; $X_9$ may be an amino acid having a hydropathic index of −2.0 to +2.0 or of −1.0 to +1.0 to may be a neutral amino acid or may be Gly, Ser, Thr, Cys, Asn, Gln, Tyr; $Z_1$ is $H_2N-$, RHN— or, RRN—; $Z_2$ may be —C(O)OH, —C(O)R, —C(O)OR, —C(O)NHR, —C(O)NRR; R at each occurrence may be independently selected from $(C_1$-$C_6)$ alkyl, $(C_1$-$C_6)$ alkenyl, $(C_1$-$C_6)$ alkynyl, substituted $(C_1$-$C_6)$ alkyl, substituted $(C_1$-$C_6)$ alkenyl, or substituted $(C_1$-$C_6)$ alkynyl; wherein "-" is a covalent linkage, and wherein the compound may be an inhibitor of AMPA receptor endocytosis. In alternative embodiments, anyone or more of $X_1$, $X_5$, or $X_8$ may be a Y.

In alternative embodiments, the compound of Formula I or A may inhibit AMPA receptor endocytosis with an affinity that is at least as great as the affinity when the compound is a polypeptide including a sequence of YREGYNVYGIE (SEQ ID NO. 1), YKEGYNVYGIE (SEQ ID NO. 2), YREGYNVYG (SEQ ID NO. 3), or YKEGYNVYG (SEQ ID NO. 4). In alternative embodiments, the compound of Formula I or A may include a similarity score of over zero based on either of the PAM or Blosum similarity matrices. In alternative embodiments, the compound of Formula I or A may further include the amino acid sequence YGRKKRRQRRR (SEQ ID NO. 5).

In alternative aspects, the invention provides the use of any of the polypeptides, nucleic acid molecules, antibodies, or compounds according to the invention for treating or preventing' neurological damage or substance abuse in a subject, or for modulating NMDA-mediated, neuronal apoptosis, or for modulating AMPA receptor endocytosis, or for modulating synaptic plasticity in a subject.

In various embodiments of the aspects of the invention, the inhibitor may include an inhibitor of regulated AMPA receptor endocytosis. In various embodiments of the aspects of the invention, the inhibitor may include a GluR2, GluR3, or GluR4 polypeptide. In various embodiments of the aspects of the invention, the inhibitor of AMPA receptor endocytosis may include a peptide including any of the amino acid sequences of YREGYNVYGIE (SEQ ID NO. 1), YKEGYNVYGIE (SEQ ID NO. 2), YREGYNVYG (SEQ ID NO. 3), or YKEGYNVYG (SEQ ID NO. 4) or a fragment or variant thereof, or may be a GluR2, GluR3, or GluR4 polypeptide, or may include an antibody that specifically binds any of the amino acid sequences of YREGYNVYGIE (SEQ ID NO. 1), YKEGYNVYGIE (SEQ ID NO. 2), YREGYNVYG (SEQ ID NO. 3), and YKEGYNVYG (SEQ ID NO. 4). In various embodiments of the aspects of the invention, the inhibitor may include the amino acid sequence set forth in Table I or conservative substitutions thereof, Formula I, or Formula A, or homologous sequences thereto found in the C-terminus of the GluR2, GluR3, or GluR4 subunits of the AMPA receptor or a fragment or variant thereof, or include an antibody that specifically binds the amino acid sequence set forth in Table I or conservative substitutions thereof, Formula I, or Formula A, or homologous sequences thereto found in the C-terminus of the GluR2, GluR3, or GluR4 subunits of the AMPA receptor. In various embodiments of the aspects of the invention, may further include the amino acid sequence YGRKKRRQRRR (SEQ ID NO. 5).

α-amino-3-hydroxy-5-methylisoxazole-4-propionic acid or "AMPA" receptors are glutamate-gated ion channel receptors that are involved in transduction of the postsynaptic signal. Native AMPA receptors may be heteromeric, e.g., heteropentameric, protein complexes assembled from combinations of GluR subunits 1-4. When transiently expressed in non-neuronal mammalian cells, individual GluR subunits can form functional homomeric AMPA receptor channels, and AMPA receptors in these heterologous expression systems can undergo both constitutive and regulated clathrindependent endocytosis. In some embodiments, an AMPA receptor includes a GluR2 subunit. GluR subunits may include without limitation the sequences described in Accession numbers NP_113796; NP_032191; NP_000818 for GluR1; NP_058957; NP_038568; NP_000817; P23819 for GluR2; NP_116785 for GluR3; or NP_058959 or NP_000820 for GluR4, and related nucleotide sequences, for example, NM_000826. Other GluR polypeptide or nucleotide sequences may be found in public databases, such as GenBank.

A "phosphorylated" AMPA receptor includes polypeptide subunits that are post-translationally modified on any amino acid residue, for example, serine, threonine, or tyrosine, that is capable of being phosphorylated in vivo. For example, a phosphorylated AMPA receptor may include a GluR2 subunit that is phosphorylated, for example, on any one or more of tyrosines 869, 873, and 876 of the sequence described in Accession number NP_000817, or phosphorylated on any one or more of tyrosine residues present in corresponding sequences in GluR subunits.

An "unphosphorylated" AMPA receptor may be incapable of being phosphorylated on an amino acid residue capable of being phosphorylated in vivo, for example, by mutation of that residue to an amino acid that is not capable of being phosphorylated. A mutation of a tyrosine to an alanine in a polypeptide sequence, for example, results in a protein that is not capable of being phosphorylated at that particular position in the polypeptide sequence. A GluR2 polypeptide that possesses an alanine or other unphosphorylatable amino acid at positions 869, 873, and/or 876 of the sequence described in Accession number NP_000817, instead of a tyrosine, is an example of such an "unphosphorylated" AMPA receptor. An unphosphorylated AMPA receptor may also be a protein that is capable of being phosphorylated in vivo, but is not phosphorylated due to, for example, the presence of an inhibitor, for example, a kinase inhibitor; due to an antibody that interferes with the phosphorylation site; due to the activity of a phosphatase; or prevented from being phosphorylated by some other means. A "constitutively phosphorylated" AMPA receptor is a protein that possesses a mutation at an amino acid residue that is capable of being phosphorylated in vivo, where the mutation mimics phosphorylation at that residue, and the resultant polypeptide possesses the biological activity of a phosphorylated polypeptide. Generally, mutation of a phosphorylatable residue to a glutamic acid or aspartic acid residue results in constitutive phosphorylation.

A GluR CT polypeptide includes a peptide derived from, or substantially identical to, the C-terminus of a GluR polypeptide and that is capable of inhibiting AMPA receptor endocytosis, or modulating neuronal apoptosis or synaptic plasticity. GluR CT peptides include, without limitation, peptides including the sequences set forth in Table I or conservative substitutions thereof, Formula I, or Formula A, or homologous sequences thereto found in the C-terminus of the GluR2, GluR3, or GluR4 subunits of the AMPA receptor. In some embodiments, a GluR CT peptide may include other sequences (e.g, TAT PTD) in the form of for example a fusion protein.

A "biologically-active fragment" of an AMPA receptor includes an amino acid sequence found in a naturally-occurring AMPA receptor that is capable of modulating apoptosis or cell death or synaptic plasticity, or undergoing endocytosis, as described herein or known to those of ordinary skill in the art. A "variant" of an AMPA receptor includes a modification, for example, by deletion, addition, or substitution, of an amino acid sequence found in a naturally-occurring AMPA receptor that is capable of modulating apoptosis or cell death, or synaptic plasticity, undergoing endocytosis, as described herein or known to those of ordinary skill in the art.

A "protein," "peptide" or "polypeptide" is any chain of two or more amino acids, including naturally occurring or non-naturally occurring amino acids or amino acid analogues, regardless of post-translational modification (e.g., glycosylation or phosphorylation). An "amino acid sequence", "polypeptide", "peptide" or "protein" of the invention may include peptides or proteins that have abnormal linkages, cross links and end caps, non-peptidyl bonds or alternative modifying groups. Such modified peptides are also within the scope of the invention. The term "modifying group" is intended to include structures that are directly attached to the peptidic structure (e.g., by covalent coupling), as well as those that are indirectly attached to the peptidic structure (e.g., by a stable non-covalent association or by covalent coupling to additional amino acid residues, or mimetics, analogues or derivatives thereof, which may flank the core peptidic structure). For example, the modifying group can be coupled to the amino-terminus or carboxy-terminus of a peptidic structure, or to a peptidic or peptido-mimetic region flanking the core domain. Alternatively, the modifying group can be coupled to a side chain of at least one amino acid residue of a peptidic structure, or to a peptidic or peptido-mimetic region flanking the core domain (e.g., through the epsilon amino group of a lysyl residue(s), through the carboxyl group of an aspartic acid residue(s) or a glutamic acid residue(s), though a hydroxy group of a tyrosyl residue(s), a serine residue(s) or a threonine residue(s) or other suitable reactive group on an amino acid side chain). Modifying groups covalently coupled to the peptidic structure can be attached by means and using methods well known in the art for linking chemical structures, including, for example, amide, alkylamino, carbamate or urea bonds. Peptides according to the invention may include the sequences set forth in Table I or conservative substitutions thereof, Formula I, or Formula A, or homologous sequences thereto, found in the C-terminus of the GluR2, GluR3, or GluR4 subunits of the AMPA receptor. In some embodiments, the peptides may include other sequences (e.g, TAT PTD) in the form of for example a fusion protein.

A "nucleic acid molecule" is any chain of two or more nucleotides including naturally occurring or non-naturally occurring nucleotides or nucleotide analogues. A nucleic acid molecule is "complementary" to another nucleic acid molecule if it hybridizes, under conditions of high stringency, with the second nucleic acid molecule. Nucleic acid molecules according to the invention include those molecules that encode the sequences set forth in Table I or conservative substitutions thereof, Formula I, or Formula A, or homologous sequences thereto, found in the C-terminus of the GluR2, GluR3, or GluR4 subunits of the AMPA receptor. In some embodiments, a nucleic acid molecule may include other sequences (e.g, sequence coding for TAT PTD) to generate for example a fusion protein.

A "substantially identical" sequence is an amino acid or nucleotide sequence that differs from a reference sequence only by one or more conservative substitutions, as discussed herein, or by one or more non-conservative substitutions, deletion, or insertions located at positions of the sequence that do not destroy biological function as described herein. Such a sequence can be any integer from 60% to 99%, or more generally at least 75%, 80%, 85%, 90%, or 95%, or as much as 96%, 97%, 98%, or 99% identical at the amino acid or nucleotide level to the sequence used for comparison. Sequence identity can be readily measured using publicly available sequence analysis software (e.g., Sequence Analysis Software Package of the Genetics Computer Group, University of Wisconsin Biotechnology Center, 1710 University Avenue, Madison, Wis. 53705, or BLAST software available from the National Library of Medicine, USA). Examples of useful software include the programs, Pile-up and PrettyBox. Such software matches, similar sequences by assigning degrees of homology to various substitutions, deletions, substitutions, and other modifications. Substantially identical sequences may for example be sequences that are substantially identical to the amino acid sequences set forth in Table I or conservative substitutions thereof, Formula I, or Formula A, or to homologous sequences thereto found in the C-terminus of the GluR2, GluR3, or GluR4 subunits of the AMPA receptor. In some embodiments, a substantially identical sequence may further include sequences substantially identical to other sequences (e.g., TAT PTD).

An antibody "specifically binds" an antigen when it recognises and binds the antigen, for example, a GluR CT peptide, but does not substantially recognise and bind other molecules in a sample, for example, a GluR CT peptide that does not include such sequences. Such an antibody has, for example, an affinity for the antigen which is 10, 100, 1000 or 10000 times greater than the affinity of the antibody for another reference molecule in a sample.

"Cell death" or "apoptosis," defines a specific execution of programmed cell death that can be triggered by several factors.[55] NMDA-mediated neuronal apoptosis is the neuronal cell death observed upon activation of NMDA receptors.

"Endocytosis" is the process by which the plasma membrane of a cell folds inward, to internalize components of the membrane as well as other materials. Receptor endocytosis is typically mediated by clathrin coated pits and vesicles.

An "inhibitor of clathrin mediated endocytosis" includes an compound that is capable of specifically inhibiting clathrin mediated endocytosis, without substantially inhibiting endocytosis in general. An inhibitor of clathrin mediated endocytosis may include, for example, myr-dyn, or inhibitors as described in Jarousse and Kelly.[62] In some embodiments, an inhibitor of AMPA receptor endocytosis may also be an inhibitor of clathrin mediated endocytosis.

An "inhibitor of AMPA receptor endocytosis" includes a compound that may be in general capable of specifically inhibiting endocytosis of the AMPA receptor, without substantially inhibiting clathrin-mediated endocytosis in general, when compared with an inhibitor of clathrin mediated endocytosis. In some embodiments, an inhibitor of AMPA receptor endocytosis may include compounds that do not affect basal levels of AMPA receptor endocytosis e.g., compounds that are inhibitors of "regulated" AMPA receptor endocytosis. In some embodiments, an inhibitor of AMPA receptor endocytosis may include compounds that are substantially identical to the amino acid sequences set forth in Table I or conservative substitutions thereof, Formula I, or Formula A, or to homologous sequences found in the C-terminus of the GluR2, GluR3, or GluR4 subunits of the AMPA receptor. In some embodiments, an inhibitor of AMPA receptor endocytosis may include an antibody that mimics the sequences set forth in Table I or conservative substitutions thereof, Formula I, or Formula A, or to homologous sequences found in the C-terminus of the GluR2, GluR3, or GluR4 subunits of the AMPA receptor, e.g., an anti-idiotypic antibody to an antibody that specifically binds a GluR CT peptide.

"Synaptic plasticity" refers to the use-dependent changes (long-term or short-term) in the efficiency of synaptic transmission between neuronal cells. Synaptic plasticity is thought to underlie the processes behind learning and memory.

A "test compound" is any naturally-occurring or artificially-derived chemical compound. Test compounds may include, without limitation, peptides, polypeptides, synthesised organic molecules, naturally occurring organic molecules, and nucleic acid molecules. A test compound may "compete" with a known compound, for example, an inhibitor of clathrin mediated endocytosis or an inhibitor of AMPA receptor endocytosis, such as a GluR-CT peptide or fragment thereof by, for example, interfering with modulation of neuronal apoptosis or cell death or synaptic plasticity, endocytosis, or protein phosphorylation, or other biological response. Generally, a test compound can exhibit any value between 10% and 200%, or over 500%, modulation when compared to a GluR-CT peptide or peptide analogue, or other reference compound. For example, a test compound may exhibit at least any positive or negative integer from 10% to 200% modulation, or at least any positive or negative integer from 30% to 150% modulation, or at least any positive or negative integer from 60% to 100% modulation, or any positive or negative integer over 100% modulation. A compound that is a negative modulator will in general decrease modulation relative to a known compound, while a compound that is a positive modulator will in general increase modulation relative to a known compound.

A "sample" can be any organ, tissue, cell, or cell extract isolated from a subject, such as a sample isolated from an animal having neurological damage or neuronal dysfunction or a neurological disorder. For example, a sample can include, without limitation, hippocampal tissue or cells, cerebellar tissue or cells, etc., or other neuronal or other tissue (e.g., from a biopsy or autopsy), isolated from an animal with neurological damage, dysfunction, or disorder, or from a normal animal i.e., not having neurological damage, dysfunction, or disorder. A sample can also include, without limitation, tissue such as neuronal cells, peripheral blood, whole blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, urine, stool, saliva, placental extracts, amniotic fluid, a cryoprecipitate, a cryosupernatant, a cell lysate, mammalian cell culture or culture medium, products of fermentation, ascitic fluid, proteins present in blood cells, solid tumours isolated from a mammal with a neuronal carcinoma, or any other specimen, or any extract thereof, obtained from a patient (human or animal), test subject, or experimental animal. A sample may also include, without limitation, products produced in cell culture by normal cells or cells isolated from a subject with neurological damage or neuronal dysfunction (e.g., via recombinant DNA technology). A "sample" may also be a cell or cell line created under experimental conditions, that are not directly isolated from a subject. A sample can also be cell-free, artificially derived or synthesised. In some embodiments, samples refer to neuronal tissue or cells. In some embodiments, the sample may be from a subject having neurological damage or neuronal dysfunction; or from a normal subject i.e., not diagnosed with or at risk for or suspected of having neurological damage or neuronal dysfunction.

As used herein, a subject may be a human, non-human primate, rat, mouse, cow, horse, pig, sheep, goat, dog, cat, Aplysia, etc. The subject may be a clinical patient, a clinical trial volunteer, an experimental animal, etc. The subject may be suspected of having or at risk for having neurological damage or neuronal dysfunction, be diagnosed with neurological damage or neuronal dysfunction, or be a control subject that is confirmed to not have neurological damage or neuronal dysfunction. Diagnostic methods for neurological damage or neuronal dysfunction and the clinical delineation of neurological damage or neuronal dysfunction diagnoses are known to those of ordinary skill in the art.

By "contacting" is meant to submit an animal, cell, lysate, extract, molecule derived from a cell, or synthetic molecule to a test compound.

By "determining" is meant analysing the effect of a test compound on the test system. The means for analysing may include, without limitation, antibody labelling, apoptosis assays, immunoprecipitation, in vivo and in vitro phosphorylation assays, cell death assays, immunofluorescence assays, ELISA, ultrastructural analysis, histological analysis, animal models, or any other methods described herein or known to those skilled in the art.

"Modulating" or "modulates" means changing, by either increase or decrease. The increase or decrease may be a change of any value between 10% and 90%, or of any value between 30% and 60%, or may be over 100%, over 200%, over 300% or over 500% when compared with a control or reference sample or compound.

Other features and advantages of the invention will be apparent from the following description of the drawings and the invention, and from the claims.

BRIEF DESCRIPTION OF THE DRAWINGS

FIGS. 1A-F. NMDA induces apoptosis in primary cultures of rat hippocampal neurons. Mature hippocampal neurons were treated with NMDA (100 μM plus 10 μM glycine; 1 h) and then returned to normal media for 24 h. In this and the following Figs., all data are expressed as mean±SEM and analyzed using a non-paired Student's t-test. A, B, NMDA treatment induces a time-dependent increase in caspase-3 activity. A: western blot of cell lysates using anti-cleaved caspase-3; B: ELISA assay detecting DEVD-pNA cleavage. C, Agarose gel electrophoresis shows significant DNA laddering after NMDA treatment. D, Cell Death ELISA assay for apoptosis measuring histone-biotinylation shows that NMDA-induced apoptosis is blocked by the competitive NMDA receptor antagonist, APV. E, F, Cell Death ELISA assays for apoptosis show that endocytosis inhibitors specifically block NMDA- but not STS-induced apoptosis in cultured hippocampal neurons.

FIGS. 2A-D. Inhibitors of endocytosis disrupt NMDA receptor-mediated activation of the cell death signaling pathway without altering NMDA receptor function. A, B, Inhibition of endocytosis has little effect on Ca2+ influx through activated NMDA receptor channels. The upper trace (A) shows a record of NMDA receptor activation-induced $[Ca^{2+}]_i$ fluctuations as measured by ratiometric changes in Fura-2 fluorescence in a single hippocampal neuron. Repetitive NMDA application (100 μM) in the region of the neuron under observation was accomplished using a pressure ejection pipette at the time points indicated by the lower black squares (500 ms each). Sucrose (400 mM) was applied to the bath as indicated by the upper black bar. The histogram at the bottom (B) summarizes $[Ca^{2+}]_i$ responses at indicated time points from three individual neurons (mean±SEM). C, A myristoylated dynamin-derived peptide inhibits NMDA induced activation of caspase-3. D, Endocytosis inhibition specifically disrupts the NMDA-, but not the STS-induced reduction in Akt phosphorylation. Cell lysates from neurons treated as indicated were first probed with an antibody specific to Akt phosphorylated on serine 473, the active form of the enzyme. Membranes were then stripped and re-probed with an anti-Akt antibody. Blots from four individual experiments were scanned and quantified. The histogram represents Akt phosphorylation relative to total Akt. **, p<0.01 when compared with the respective control group.

FIGS. 4A-B. Blocking AMPA receptor endocytosis with R2-CT prevents NMDA- but not STS-induced apoptosis in cultured hippocampal neurons. A, Cell Death ELISA assay for apoptosis showing that R2-CT blocks NMDA— but not STS-induced apoptosis. B, Cell counting for apoptosis of PI stained cells after fixation, showing that R2-CT blocked NMDA-induced apoptosis.

FIGS. 5A-B. Construction of GluR2 internal deletion or carboxyl terminal truncation mutants and identification of a tyrosine-based signal (GluR2-3Y). A, CT sequences of internal deletion or truncation mutants of the full-length HA-tagged or non-tagged GluR2 subunit. B, Quantification of cell-surface expressed AMPARs containing the GluR2, or its various mutant constructs, which were transiently transfected into HEK293 cells and assayed by colorimetric cell-ELISA (n=6). Expression levels of the constructs following transient transfection into HEK293 cells were determined by cell-ELISA assays using an anti-HA antibody for HA tagged constructs, or an anti-GluR2 subunit antibody for the non-HA tagged construct, under permeabilized conditions. The level of expression was normalized to the expression level of the corresponding wild type construct (i.e. HA-GluR2 or GluR2). All mutants were expressed at a level similar to the wild type counterparts. Removing the tyrosine based signal prevents insulin induced depletion of cell surface AMPARs (filled bars) without affecting the basal receptor level. Removing NSF-binding domains affects basal, but not insulin-reduced receptor expression, and that unlike neurons, both AP2 and PICK1-based endocytosis signals are non-functional in HEK cells. *p<0.05, **p<0.01.

FIGS. 10A-E. Tyrosine phosphorylation of the GluR2 subunit is required for LFS-induced hippocampal CA1 long-term depression (LTD). A. Homogenates of control or LFS-treated hippocampal slices were immunoprecipitated with anti-GluR1 or GluR2 antibodies and sequentially probed with anti-phosphotyrosine (PY), anti-GluR1 (GluR1) and anti-GluR2 antibodies (GluR2) as described herein. The lane marked M contains molecular weight standards. B. The results of three individual experiments are summarized in the bar graph. **p=0.01 C. Representative responses are shown on the left. D. The graphs on the right, and in E, depict normalized EPSCs (EPSCt/EPSC0) from neurons recorded as described with pipettes containing standard intracellular solution (Control, n=7) or intracellular solution supplemented with GluR23Y (B; n=6), GluR23A (B; n=7) or GluR2834-843 (C; n=5). The LFS was delivered during the time period indicated by the black horizontal bar.

FIG. 12A-D. Systemic application of Tat-GlurR2$_{3y}$ peptide blocks the expression of behavioural sensitization to the abusive drug d-amphetemine in an animal model of drug addiction. GluR2-3Y or GluR2-3A peptide was fused to a Tat transduction domain (Tat-GluR2-3Y or GluR2-3A) to facilitate membrane permeability. Intravenous administration (IV; 1.5 nM/g) or direct microinjection into the nucleus accumbens (NAc) with the interference peptide GluR2-3Y, but not by the control peptide GluR2-3A, blocks D-amphetamine (D-Amph)-induced behavioural sensitization of stereotypy. A. Stereotypy scores assessed at various time points shows blockade of of sensitization following N injection of Tat-GluR2-3Y. Points represent mean stereotypy scores (+S.E.M) for each group of rats tested over the 2 hour session. Chronic saline-treated rats served as control subjects. B. Summary of the changes in stereotypy scores across the 2 hr test session converted to the Area Under The Curve (AUC) for individual groups depicted in graph A. C. Intracranial microinjection of GluR2-3Y into the NAc also blocks D-Amph-induced sensitization. D. Intracranial microinjection of the GluR2-3Y peptide into the ventral tegmental area (VTA) does not block D-Amph-induced behavioural sensitization. (*=<0.05, relative to acute amphetamine group.)

FIG. 19. GluR2$_{3y}$ peptide blocked stress induced anxiety in a rat model of stress. Rats (n=2) were injected with either 10 nM/g GluR2-3Y or equal volume of vehicle ACSF (IP). They were given 30 minutes in a dark room post injection. After that they were placed on an elevated platform for 30 minutes as a stressor. After that 30 minutes they were placed on the elevated plus maze for 5 minutes. The GluR2-3Y injected rats spent more time on the open arms than the ACSF rats. The ACSF rats spent most of their time in the corners of the closed arms or rearing to look over the walls. Thus, GluR23Y peptide blocked stress induced anxiety. These results strongly suggest that facilitated AMPAR endocytosis and hence the expression of LTD play an indispensable role in the expression of stress-induced behaviors and that LTD blocker such as the GluR23Y may be used therapeutics to treat stress-related brain disorders.

DETAILED DESCRIPTION OF THE INVENTION

Figure 3A:
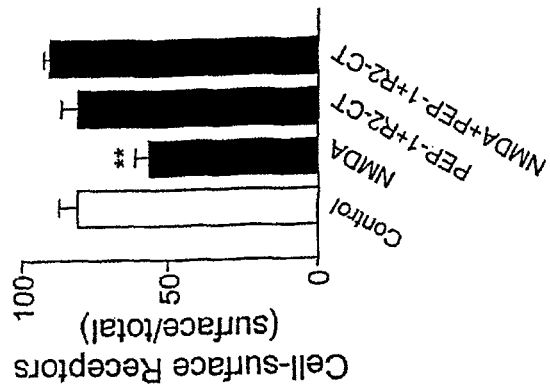
FIGS. 3A-B. NMDA induces AMPA receptor but not NMDA receptor endocytosis, which is blocked by the membrane permeable myristoylated dynamin peptide (Myr-Dyn) as well as a peptide derived from GluR2 c-tail (R2-CT). A, ELISA-based cell-surface receptor assay for NMDA receptor and AMPA receptor. NMDA treatment induced a significant reduction in cell surface AMPA receptor but not NMDA receptor, and AMPA receptor internalization was prevented by pretreatment of neurons with the myristoylated, membrane permeable dynamin inhibitor peptide (Myr-Dyn; 10 μM), but not the membrane impermeable control, Dyn (**denotes p<0.01, compared with control; n=36-72 wells from three separate experiments for each group). B, NMDA-induced AMPA receptor internalization is blocked by R2-CT, a peptide that specifically blocked regulated AMPA receptor endocytosis.

The invention provides, in part, methods and reagents for modulating neuronal apoptosis. The invention also provides, in part, methods and reagents for modulating synaptic plasticity. For example, compounds according to the invention may be used as neuroprotective agents that are capable of modulating AMPA receptor endocytosis. In some embodiments, such compounds can modulate AMPA receptor endocytosis and block neuronal apoptosis without affecting NMDA receptor function, and therefore may bypass the negative effects of blocking NMDA receptor function.

Alternative embodiments and examples of the invention are described herein. These embodiments and examples are illustrative and should not be construed as limiting the scope of the invention.

Assays

Various assays, as described herein or known to one of ordinary skill in the art, may be performed to determine the modulatory activity of a compound according to the invention. For example, modulation of synaptic plasticity, AMPA receptor endocytosis, NMDA-induced neuronal apoptosis, or AMPA receptor phosphorylation, may be tested as described herein or as known to one of ordinary skill in the art. In some embodiments, assays may be performed to test compounds for ability to inhibit AMPA receptor endocytosis. Such assays include without limitation nucleic acid, polypeptide, small molecule etc. based assays, such as immunoassays, hybridization assays, small molecule binding assays, peptide binding assays, antibody binding assays, competition assays, endocytosis assays, phosphorylation assays, apoptosis and cell death assays, histochemistry, animal and in vitro model assays, etc.

AMPA receptor polypeptides may be provided in neuronal or non-neuronal cells, or cell lysates. Cells and cell lines may be obtained from commercial sources, for example, ATCC, Manassas, Va., USA. Suitable animal models for neurological disorders may be obtained from, for example, The Jackson Laboratory, Bar Harbor, Me., USA or from other sources. Suitable animal models include models for stroke[87-94], drug addiction[101-106,112], schizophrenia[107-111], Huntington's Disease[112], Epilepsy[115], neuro-complication of AIDS[116], mental retardation (e.g., Fragile X retardation, Rett syndrome)[117,118], and multiple sclerosis[119,120].

The assays may be conducted using detectably labelled molecules, i.e., any means for marking and identifying the presence of a molecule, e.g., an oligonucleotide probe or primer, a gene or fragment thereof, a peptide, or a cDNA molecule. Methods for detectably-labelling a molecule are well known in the art and include, without limitation, radioactive labelling (e.g., with an isotope such as $^{32}$P or $^{35}$S) and nonradioactive labelling such as, enzymatic labelling (for example, using horseradish peroxidase or alkaline phosphatase), chemiluminescent labeling, fluorescent labeling (for example, using fluorescein), bioluminescent labeling, or antibody detection of a ligand attached to the probe. Also included in this definition is a molecule that is detectably labelled by an indirect means, for example, a molecule that is bound with a first moiety (such as biotin) that is, in turn, bound to a second moiety that may be observed or assayed (such as fluorescein-labeled streptavidin). Labels also include digoxigenin, luciferases, and aequorin.

Disorders and Conditions

Any disorder or condition which includes neural dysfunction, for example due to neurological damage or behavioural sensitization due to the excessive activation of NMDA receptors or due to changes in AMPA receptor endocytosis may be treated, prevented, or studied according to the methods and compounds of the invention. Therefore, disorders associated with other conditions ranging from hypoglycemia, hypoxia, and cardiac arrest to epilepsy are considered neurological damage disorders according to the invention. Disorders according to the invention include without limitation cerebral ischemia, occurring for example after stroke (ischemic stroke due to for example atherothrombotic disease of e.g., extracranial arteries, or to emboli from the heart or lacunar infarcts) or brain trauma (e.g., intracerebral hemorrhage or subarachnoid hemorrhage); head injury; neurodegenerative disorders in which compromised neurons become sensitive to excitotoxic damage; Alzheimer's, Parkinson's, or Huntington's disease; epilepsy; neuropathic pain; amyotrophic lateral sclerosis (ALS); Hutchinson Gilford syndrome; diabetes; ataxia; mental retardation; or dementias. Major risk factors for stroke include smoking, diabetes, obesity, and high blood pressure. Accordingly, subjects having any of these conditions or behaviours may be considered as having a disorder according to the invention.

Disorders according to the invention also include those disorders associated with defects or dysfunction in learning or memory; psychiatric disorders, such as autism, schizophrenia or fragile X syndrome; or disorders associated with substance abuse or addition to drugs, including nicotine, alcohol, opiates such as heroin, codeine and morphine, including derivatives such as pethidine and methadone, nicotine, marijuana, phenyclidene, psychostimulants such as amphetamines and cocaine, barbiturates such as pentobarbitone and quinalbarbitone, and benzodiazepines such as temazepam, diazepam and flunitrazepam.

Antibodies

The compounds of the invention can be used to prepare antibodies to GluR2-CT peptides or analogues thereof, for example, the sequences set forth in Table I or conservative substitutions thereof, Formula I, or Formula A, or to homologous sequences found in the C-terminus of the GluR2, GluR3, or GluR4 subunits of the AMPA receptor, using standard techniques of preparation as, for example, described in Harlow and Lane[56], or known to those skilled in the art. Antibodies can be tailored to minimise adverse host immune response by, for example, using chimeric antibodies contain an antigen binding domain from one species and the Fc portion from another species, or by using antibodies made from hybridomas of the appropriate species. In alternative embodiments of the invention, antibodies may be raised, for example, against a phosphorylated GluR-CT peptide that is phosphorylated one or more tyrosines or serines or threonines. In alternative embodiments of the invention, antibodies may be raised, for example, against a constitutively phosphorylated GluR-CT peptide that replaces existing tyrosines or serines or threonines with glutamates and aspartates. In some embodiments, anti-idiotypic antibodies may be raised, for example, against to an antibody that specifically binds a GluR CT peptide or analogue thereof.

Polypeptides and Test Compounds

In one aspect, compounds according to the invention include GluR2, GluR3, or GluR4 peptides and analogues and variants thereof, including, for example, the peptides described herein that are phosphorylated or unphosphorylated at any one of the three tyrosines, including polypeptides that are constitutively phosphorylated, or that are unphosphorylatable, as well as homologs and fragments thereof. For example, compounds according to the invention include peptides including the sequences set forth in Table I or analogues or variants thereof.

TABLE I

| SEQ ID NO. | SEQUENCE | SEQ ID NO. | SEQUENCE | SEQ ID NO. | SEQUENCE | SEQ ID NO. | SEQUENCE | SEQ ID NO. | SEQUENCE |
|---|---|---|---|---|---|---|---|---|---|
| 4 | YKEGYNVYG | 8 | YKEGYNVDG | 9 | YKEGYNVEG | 10 | YKEGYNVSG | 11 | YKEGYNVTG |
| 12 | YKEGDNVYG | 13 | YKEGDNVDG | 14 | YKEGDNVEG | 15 | YKEGNVSG | 16 | YKEGDNVTG |
| 17 | YKEGENVYG | 18 | YKEGENVDG | 19 | YKEGENVEG | 20 | YKEGENVSG | 21 | YKEGENVTG |
| 22 | YKEGSNVYG | 23 | YKEGSNVDG | 24 | YKEGSNVEG | 25 | YKEGSNVSG | 26 | YKEGSNVTG |
| 27 | YKEGTNVYG | 28 | YKEGTNVDG | 29 | YKEGTNVEG | 30 | YKEGTNVSG | 31 | YKEGTNVTG |
| 32 | DKEGYNVYG | 33 | DKEGYNVDG | 34 | DKEGYNVEG | 35 | DKEGYNVSG | 36 | DKEGYNVTG |
| 37 | DKEGDNVYG | 38 | DKEGDNVDG | 39 | DKEGDNVEG | 40 | DKEGDNVSG | 41 | DKEGDNVTG |
| 42 | DKEGENVYG | 43 | DKEGENVDG | 44 | DKEGENVEG | 45 | DKEGENVSG | 46 | DKEGENVTG |
| 47 | DKEGSNVYG | 48 | DKEGSNVDG | 49 | DKEGSNVEG | 50 | DKEGSNVSG | 51 | DKEGSNVTG |
| 52 | DKEGTNVYG | 53 | DKEGTNVDG | 54 | DKEGTNVEG | 55 | DKEGTNVSG | 56 | DKEGTNVTG |
| 57 | EKEGYNVYG | 58 | EKEGYNVDG | 59 | EKEGYNVEG | 60 | EKEGYNVSG | 61 | EKEGYNVTG |
| 62 | EKEGDNVYG | 63 | EKEGDNVDG | 64 | EKEGDNVEG | 65 | EKEGDNVSG | 66 | EKEGDNVTG |
| 67 | EKEGENVYG | 68 | EKEGENVDG | 69 | EKEGENVEG | 70 | EKEGENVSG | 71 | EKEGENVTG |
| 72 | EKEGSNVYG | 73 | EKEGSNVDG | 74 | EKEGSNVEG | 75 | EKEGSNVSG | 76 | EKEGSNVTG |
| 77 | EKEGTNVYG | 78 | EKEGTNVDG | 79 | EKEGTNVEG | 80 | EKEGTNVSG | 81 | EKEGTNVTG |
| 82 | SKEGYNVYG | 83 | SKEGYNVDG | 84 | SKEGYNVEG | 85 | SKEGYNVSG | 86 | SKEGYNVTG |
| 87 | SKEGDNVYG | 88 | SKEGDNVDG | 89 | SKEGDNVEG | 90 | SKEGDNVSG | 91 | SKEGDNVTG |
| 92 | SKEGENVYG | 93 | SKEGENVDG | 94 | SKEGENVEG | 95 | SKEGENVSG | 96 | SKEGENVTG |
| 97 | SKEGSNVYG | 98 | SKEGSNVDG | 99 | SKEGSNVEG | 100 | SKEGSNVSG | 101 | SKEGSNVTG |
| 102 | SKEGTNVYG | 103 | SKEGTNVDG | 104 | SKEGTNVEG | 105 | SKEGTNVSG | 106 | SKEGTNVTG |
| 107 | TKEGYNVYG | 108 | TKEGYNVDG | 109 | TKEGYNVEG | 110 | TKEGYNVSG | 111 | TKEGYNVTG |
| 112 | TKEGDNVYG | 113 | TKEGDNVDG | 114 | TKEGDNVEG | 115 | TKEGDNVSG | 116 | TKEGDNVTG |
| 117 | TKEGENVYG | 118 | TKEGENVDG | 119 | TKEGENVEG | 120 | TKEGENVSG | 121 | TKEGENVTG |
| 122 | TKEGSNVYG | 123 | TKEGSNVDG | 124 | TKEGSNVEG | 125 | TKEGSNVSG | 126 | TKEGSNVTG |
| 127 | TKEGTNVYG | 128 | TKEGTNVDG | 129 | TKEGTNVEG | 130 | TKEGTNVSG | 131 | TKEGTNVTG |
| 3 | YREGYNVYG | 132 | YREGYNVDG | 133 | YKEGYNVEG | 134 | YKEGYNVSG | 135 | YREGYNVTG |
| 136 | YREGDNVYG | 137 | YREGDNVDG | 138 | YREGDNVEG | 139 | YREGDNVSG | 140 | YREGDNVTG |
| 141 | YREGENVYG | 142 | YREGENVDG | 143 | YREGENVEG | 144 | YREGENVSG | 145 | YREGENVTG |
| 146 | YREGSNVYG | 147 | YREGSNVDG | 148 | YREGSNVEG | 149 | YREGSNVSG | 150 | YREGSNVTG |
| 151 | YREGTNVYG | 152 | YREGTNVDG | 153 | YREGTNVEG | 154 | YREGTNVSG | 155 | YREGTNVTG |
| 156 | DREGYNVYG | 157 | DREGYNVDG | 158 | DREGYNVEG | 159 | DREGYNVSG | 160 | DREGYNVTG |
| 161 | DREGDNVYG | 162 | DREGDNVDG | 163 | DREGDNVEG | 164 | DREGDNVSG | 165 | DREGDNVTG |
| 166 | DREGENVYG | 167 | DREGENVDG | 168 | DREGENVEG | 169 | DREGENVSG | 170 | DREGENVTG |
| 171 | DREGSNVYG | 172 | DREGSNVDG | 173 | DREGSNVEG | 174 | DREGSNVSG | 175 | DREGSNVTG |
| 176 | DREGTNVYG | 177 | DREGTNVDG | 178 | DREGTNVEG | 179 | DREGTNVSG | 180 | DREGTNVTG |
| 181 | EREGYNVYG | 182 | EREGYNVDG | 183 | EREGYNVEG | 184 | EREGYNVSG | 185 | EREGYNVTG |
| 186 | EREGDNVYG | 187 | EREGDNVDG | 188 | EREGDNVEG | 189 | EREGDNVSG | 190 | EREGDNVTG |
| 191 | EREGENVYG | 192 | EREGENVDG | 193 | EREGENVEG | 194 | EREGENVSG | 195 | EREGENVTG |

TABLE I-continued

| SEQ ID NO. | SEQUENCE | SEQ ID NO. | SEQUENCE | SEQ ID NO. | SEQUENCE | SEQ ID NO. | SEQUENCE | SEQ ID NO. | SEQUENCE |
|---|---|---|---|---|---|---|---|---|---|
| 196 | EREGSNVYG | 197 | EREGSNVDG | 198 | EREGSNVEG | 199 | EREGSNVSG | 200 | EREGSNVTG |
| 201 | EREGTNVYG | 202 | EREGTNVDG | 203 | EREGTNVEG | 204 | EREGTNVSG | 205 | EREGTNVTG |
| 206 | SREGYNVYG | 207 | SREGYNVDG | 208 | SREGYNVEG | 209 | SREGYNVSG | 210 | SREGYNVTG |
| 211 | SREGDNVYG | 212 | SREGDNVDG | 213 | SREGDNVEG | 214 | SREGDNVSG | 215 | SREGDNVTG |
| 216 | SREGENVYG | 217 | SREGENVDG | 218 | SREGENVEG | 219 | SREGENVSG | 220 | SREGENVTG |
| 221 | SREGSNVYG | 222 | SREGSNVDG | 223 | SREGSNVEG | 224 | SREGSNVSG | 225 | SREGSNVTG |
| 226 | SREGTNVYG | 227 | SREGTNVDG | 228 | SREGTNVEG | 229 | SREGTNVSG | 230 | SREGTNVTG |
| 231 | TREGYNVYG | 232 | TREGYNVDG | 233 | TREGYNVEG | 234 | TREGYNVSG | 235 | TREGYNVTG |
| 236 | TREGDNVYG | 237 | TREGDNVDG | 238 | TREGDNVEG | 239 | TREGDNVSG | 240 | TREGDNVTG |
| 241 | TREGENVYG | 242 | TREGENVDG | 243 | TREGENVEG | 244 | TREGENVSG | 245 | TREGENVTG |
| 246 | TREGSNVYG | 247 | TREGSNVDG | 248 | TREGSNVEG | 249 | TREGSNVSG | 250 | TREGSNVTG |
| 251 | TREGTNVYG | 252 | TREGTNVDG | 253 | TREGTNVEG | 254 | TREGTNVSG | 255 | TREGTNVTG |
| 2 | YKEGYNVYGIE | 256 | YKEGYNVDGIE | 257 | YKEGYNVEGIE | 258 | YKEGYNVSGIE | 259 | YKEGYNVTGIE |
| 260 | YKEGDNVYGIE | 261 | YKEGDNVDGIE | 262 | YKEGDNVEGIE | 263 | YKEGDNVSGIE | 264 | YKEGDNVTGIE |
| 265 | YKEGENVYGIE | 266 | YKEGENVDGIE | 267 | YKEGENVEGIE | 268 | YKEGENVSGIE | 269 | YKEGENVTGIE |
| 270 | YKEGSNVYGIE | 271 | YKEGSNVDGIE | 272 | YKEGSNVEGIE | 273 | YKEGSNVSGIE | 274 | YKEGSNVTGIE |
| 275 | YKEGTNVYGIE | 276 | YKEGTNVDGIE | 277 | YKEGTNVEGIE | 278 | YKEGTNVSGIE | 279 | YKEGTNVTGIE |
| 280 | DKEGYNVYGIE | 281 | DKEGYNVDGIE | 282 | DKEGYNVEGIE | 283 | DKEGYNVSGIE | 284 | DKEGYNVTGIE |
| 285 | DKEGDNVYGIE | 286 | DKEGDNVDGIE | 287 | DKEGDNVEGIE | 288 | DKEGDNVSGIE | 289 | DKEGDNVTGIE |
| 290 | DKEGENVYGIE | 291 | DKEGENVDGIE | 292 | DKEGENVEGIE | 293 | DKEGENVSGIE | 294 | DKEGENVTGIE |
| 295 | DKEGSWVYGIE | 296 | DKEGSNVDGIE | 297 | DKEGSMVEGIE | 298 | DKEGSNVSGIE | 299 | DKEGSNVTGIE |
| 300 | DKEGTNVYGIE | 301 | DKEGTNVDGIE | 302 | DKEGTNVEGIE | 303 | DKEGTNVSGIE | 304 | DKEGTNVTGIE |
| 305 | EKEGYNVYGIE | 306 | EKEGYNVDGIE | 307 | EKEGYNVEGIE | 308 | EKEGYNVSGIE | 309 | EKEGYNVTGIE |
| 310 | EKEGDNVYGIE | 311 | EKEGDNVDGIE | 312 | EKEGDNVEGIE | 313 | EKEGDNVSGIE | 314 | EKEGDNVTGIE |
| 315 | EKEGENVYGIE | 316 | EKEGENVDGIE | 317 | EKEGENVEGIE | 318 | EKEGENVSGIE | 319 | EKEGENVTGIE |
| 320 | EKEGSNVYGIE | 321 | EKEGSNVDGIE | 322 | EKEGSNVEGIE | 323 | EKEGSNVSGIE | 324 | EKEGSNVTGIE |
| 325 | EKEGTNVYGIE | 326 | EKEGTNVDGIE | 327 | EKEGTNVEGIE | 328 | EKEGTNVSGIE | 329 | EKEGTNVTGIE |
| 330 | SKEGYNVYGIE | 331 | SKEGYNVDGIE | 332 | SKEGYNVEGIE | 333 | SKEGYNVSGIE | 334 | SKEGYNVTGIE |
| 335 | SKEGDNVYGIE | 336 | SKEGDNVDGIE | 337 | SKEGDNVEGIE | 338 | SKEGDNVSGIE | 339 | SKEGDNVTGIE |
| 340 | SKEGENVYGIE | 341 | SKEGENVDGIE | 342 | SKEGEKVEGIE | 343 | SKEGENVSGIE | 344 | SKEGENVTGIE |
| 345 | SKEGSNVYGIE | 346 | SKEGSNVDGIE | 347 | SKEGSNVEGIE | 348 | SKEGSNVSGIE | 349 | SKEGSNVTGIE |
| 350 | SKEGTNVYGIE | 351 | SKEGTNVDGIE | 352 | SKEGTNVEGIE | 353 | SKEGTNVSGIE | 354 | SKEGTNVTGIE |
| 355 | TKEGYNVYGIE | 356 | TKEGYNVDGIE | 357 | TKEGYNVEGIE | 358 | TKEGYNVSGIE | 359 | TKEGYNVTGIE |
| 360 | TKEGDNVYGIE | 361 | TKEGDNVDGIE | 362 | TKEGDNVEGIE | 363 | TKEGDNVSGIE | 364 | TKEGDNVTGIE |
| 365 | TKEGENVYGIE | 366 | TKEGENVDGIE | 367 | TKEGENVEGIE | 368 | TKEGENVSGIE | 369 | TKEGENVTGIE |
| 370 | TKEGSNVYGIE | 371 | TKEGSNVDGIE | 372 | TKEGSNVEGIE | 373 | TKEGSNVSGIE | 374 | TKEGSNVTGIE |
| 375 | TKEGTNVYGIE | 376 | TKEGTNVDGIE | 377 | TKEGTNVEGIE | 378 | TKEGTNVSGIE | 379 | TKEGTNVTGIE |
| 1 | YREGYNVYGIE | 380 | YREGYNVDGIE | 381 | YREGYNVEGIE | 382 | YREGYNVSGIE | 383 | YREGYNVTGIE |

TABLE I-continued

| SEQ ID NO. | SEQUENCE | SEQ ID NO. | SEQUENCE | SEQ ID NO. | SEQUENCE | SEQ ID NO. | SEQUENCE | SEQ ID NO. | SEQUENCE |
|---|---|---|---|---|---|---|---|---|---|
| 384 | YREGDNVYGIE | 385 | YREGDNVDGIE | 386 | YREGDNVEGIE | 387 | YREGDSVSGIE | 388 | YREGDNVTGIE |
| 389 | YREGENVYGIE | 390 | YREGENVDGIE | 391 | YREGENVEGIE | 392 | YREGENVSGIE | 393 | YREGENVTGIE |
| 394 | YREGSNVYGIE | 395 | YREGSNVDGIE | 396 | YREGSNVEGIE | 397 | YREGSNVSGIE | 398 | YREGSNVTGIE |
| 399 | YREGTNVYGIE | 400 | YREGTNVDGIE | 401 | YREGTNVEGIE | 402 | YREGTNVSGIE | 403 | YREGTNVTGIE |
| 404 | DREGYNVYGIE | 405 | DREGYNVDGIE | 406 | DREGYNVEGIE | 407 | DREGYNVSGIE | 408 | DREGYNVTGIE |
| 409 | DREGDNVYGIE | 410 | DREGDNVDGIE | 411 | DREGDNVEGIE | 412 | DREGDNVSGIE | 413 | DREGDNVTGIE |
| 414 | DREGENVYGIE | 415 | DREGENVDGIE | 416 | DREGENVEGIE | 417 | DREGENVSGIE | 418 | DREGENVTGIE |
| 419 | DREGSNVYGIE | 420 | DREGSNVDGIE | 421 | DREGSNVEGIE | 422 | DREGSNVSGIE | 423 | DREGSNVTGIE |
| 424 | DREGTNVYGIE | 425 | DREGTNVDGIE | 426 | DREGTNVEGIE | 427 | DREGTNVSGIE | 428 | DREGTNVTGIE |
| 429 | EREGYNVYGIE | 430 | EREGYNVDGIE | 431 | EREGYNVEGIE | 432 | EREGYNVSGIE | 433 | EREGYNVTGIE |
| 434 | EREGDNVYGIE | 435 | EREGDNVDGIE | 436 | EREGDNVEGIE | 437 | EREGDNVSGIE | 438 | EREGDNVTGIE |
| 439 | EREGENVYGIE | 440 | EREGENVDGIE | 441 | EREGENVEGIE | 442 | EREGENVSGIE | 443 | EREGENVTGIE |
| 444 | EREGSNVYGIE | 445 | EREGSNVDGIE | 446 | EREGSNVEGIE | 447 | EREGSNVSGIE | 448 | EREGSNVTGIE |
| 449 | EREGTNVYGIE | 450 | EREGTNVDGIE | 451 | EREGTNVEGIE | 452 | EREGTNVSGIE | 453 | EREGTNVTGIE |
| 454 | SREGYNVYGIE | 455 | SREGYNVDGIE | 456 | SREGYNVEGIE | 457 | SREGYNVSGIE | 458 | SREGYNVTGIE |
| 459 | SREGDNVYGIE | 460 | SREGDNVDGIE | 461 | SREGDNVEGIE | 462 | SREGDNVSGIE | 463 | SREGDNVTGIE |
| 464 | SREGENVYGIE | 465 | SREGENVDGIE | 466 | SREGENVEGIE | 467 | SREGENVSGIE | 468 | SREGENVTGIE |
| 469 | SREGSNVYGIE | 470 | SREGSNVDGIE | 471 | SREGSNVEGIE | 472 | SREGSNVSGIE | 473 | SREGSNVTGIE |
| 474 | SREGTNVYGIE | 475 | SREGTNVDGIE | 476 | SREGTNVEGIE | 477 | SREGTNVSGIE | 478 | SREGTNVTGIE |
| 479 | TREGYNVYGIE | 480 | TREGYNVDGIE | 481 | TREGYNVEGIE | 482 | TREGYNVSGIE | 483 | TREGYNVTGIE |
| 484 | TREGDNVYGIE | 485 | TREGDNVDGIE | 486 | TREGDNVEGIE | 487 | TREGDNVSGIE | 488 | TREGDNVTGIE |
| 489 | TREGENVYGIE | 490 | TREGENVDGIE | 491 | TREGENVEGIE | 492 | TREGENVSGIE | 493 | TREGENVTGIE |
| 494 | TREGSNVYGIE | 495 | TREGSNVDGIE | 496 | TREGSNVEGIE | 497 | TREGSNVSGIE | 498 | TREGSNVTGIE |
| 499 | TREGTNVYGIE | 500 | TREGTNVDGIE | 501 | TREGTNVEGIE | 502 | TREGTNVSGIE | 503 | TREGTNVTGIE |
| 5 | YGRKKRRQRRR | 6 | GSTYKEGYNVYG | 7 | GSTAKEGANVAG | | | | |

In some embodiments, compounds according to the invention do not have, or have to a lesser extent, the negative side effects associated with the use of other neuroprotective agents. For example, compounds according to the invention may exhibit any value from between 10% to 100% reduction in psychotomimesis, respiratory depression, cardiovascular disregulation, or any other adverse side effect when compared to a NMDA receptor antagonist or glutamate release blocker (such as Selfotel, Gavestinel, Aptinagel, memantine, etc.[75-78,95-99]).

In some embodiments, compounds according to the invention are similarly efficacious or more efficacious than existing neuroprotective agents such as NMDA receptor antagonists (e.g., Gavestinel, or Aptinagel) or other neuroprotective agents (e.g., Kappa opiod peptide R antagonist such as Cervene; NOS inhibitors such as Lubeluzole; Na$^+$ channel blockers such as Lubeluzole; cell membrane stabilizers such as Citicoline; Ca$^{2+}$ channel antagonists; anti-ICAM antibodies such as Enlimornab; GABA$_A$ receptor modulators such as Clomethiazole; glutamate release inhibitors such as Riluzole).[79-84,100] For example, compounds according to the invention may exhibit any value from between 0% to 100% or greater than 100% efficacy when compared with other neuroprotective agents.

In alternative embodiments, one or more of the compounds described herein may be specifically excluded from one or more aspects of the invention.

Compounds can be prepared by, for example, replacing, deleting, or inserting an amino acid residue at any position of a GluR peptide or peptide analogue, for example, a GluR2-CT peptide sequence as set forth in Table I, Formula I, or Formula A, or to homologous sequences found in the C-terminus of the GluR2, GluR3, or GluR4 subunits of the AMPA receptor, as described herein, with other conservative amino acid residues, i.e., residues having similar physical, biological, or chemical properties, and screening for the ability of the compound to inhibit endocytosis of the AMPA receptor. In some embodiments of the invention, compounds of the invention include antibodies that specifically bind to a GluR polypeptide, for example, a GluR2-CT peptide, which may be phosphorylated, unphosphorylated, unphosphorylatable, or constitutively phosphorylated. In some embodiments of the invention, compounds of the invention include antibodies that bind to antibodies that specifically bind GluR CT peptides.

It is well known in the art that some modifications and changes can be made in the structure of a polypeptide without substantially altering the biological function of that peptide, to obtain a biologically equivalent polypeptide. For example, in some embodiments, compounds according to the invention may be adapted or modified for oral administration such that they are resistant to digestion by stomach acids. In one aspect of the invention, polypeptides of the present invention also extend to biologically equivalent peptides that differ from a portion of the sequence of the polypeptides of the present invention by conservative amino acid substitutions. As used herein, the term "conserved amino acid substitutions" or "conservative substitution" refers to the substitution of one amino acid for another at a given location in a GluR CT peptide (e.g., as set forth in Table I, Formula I, or Formula A, or to homologous sequences found in the C-terminus of the GluR2, GluR3, or GluR4 subunits of the AMPA receptor), where the substitution can be made without substantial loss of the relevant function. In making such cbRnges, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

As used herein, the term "amino acids" means those L-amino acids commonly found in naturally occurring proteins, D-amino acids and such amino acids when they have been modified. Accordingly, amino acids of the invention may include, for example: 2-Aminoadipic acid; 3-Aminoadipic acid; beta-Alanine; beta-Aminopropionic acid; 2-Aminobutyric acid; 4-Aminobutyric acid; piperidinic acid; 6-Aminocaproic acid; 2-Aminoheptanoic acid; 2-Aminoisobutyric acid; 3-Aminoisobutyric acid; 2-Aminopimelic acid; 2,4 Diaminobutyric acid; Desmosine; 2,2'-Diaminopimelic acid; 2,3-Diaminopropionic acid; N-Ethylglycine; N-Ethylasparagine; Hydroxylysine; allo-Hydroxylysine; 3-Hydroxyproline; 4-Hydroxyproline; Isodesmosine; allo-Isoleucine; N-Methylglycine; sarcosine; N-Methylisoleucine; 6-N-methyllysine; N-Methylvaline; Norvaline; Norleucine; and Ornithine.

In some embodiments, conserved amino acid substitutions may be made where an amino acid residue is substituted for another having a similar hydrophilicity value (e.g., within a value of plus or minus 2.0, or plus or minus 1.5, or plus or minus 1.0, or plus or minus 0.5), where the following may be an amino acid having a hydropathic index of about −1.6 such as Tyr (−1.3) or Pro (−1.6) are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conservative amino acid substitutions may be made where an amino acid residue is substituted for another having a similar hydropathic index (e.g., within a value of plus or minus 2.0, or plus or minus 1.5, or plus or minus 1.0, or plus or minus 0.5). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conservative amino acid substitutions may be made using publicly available families of similarity matrices.[63-69] The PAM matrix is based upon counts derived from an evolutionary model, while the Blosum matrix uses counts derived from highly conserved blocks within an alignment. A similarity score of above zero in either of the PAM or Blosum matrices may be used to make conservative amino acid substitutions.

In alternative embodiments, conservative amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Gln; basic: Lys, Arg, His; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In alternative embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al.[57] Genetically encoded hydrophobic amino acids include Gly, Ala, Phe, Val, Leu, Ile, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, C(O)NH$_2$, —C(O)NHR, —C(O)NRR, etc., where R is independently ($C_1$-$C_6$) alkyl, substituted ($C_1$-$C_6$) alkyl, ($C_1$-$C_6$) alkenyl, substituted ($C_1$-$C_6$) alkenyl, ($C_1$-$C_6$) alkynyl, substituted ($C_1$-$C_6$) alkynyl, ($C_5$-$C_{20}$) aryl, substituted ($C_5$-$C_{20}$) aryl, ($C_6$-$C_{26}$) alkaryl, substituted ($C_6$-$C_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Trp, while non-genetically encoded aromatic amino acids include phenylglycine, 2-napthylalanine, beta-2-thienylalanine, 1,2,3,4-tetrahydro-isoquinoline-3-carboxylic acid, 4-chlorophenylalanine, 2-fluorophenylalanine3-fluorophenylalanine, and 4-fluorophenylalanine.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met, while non-genetically encoded apolar amino acids include cyclohexylalanine. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile, while non-genetically encoded aliphatic amino acids include norleucine.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln, while non-genetically encoded polar amino acids include citrulline, N-acetyl lysine, and methionine sulfoxide. An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His, while non-genetically encoded basic amino acids include the non-cyclic amino acids ornithine, 2,3-diaminopropionic acid, 2,4-diaminobutyric acid, and homoarginine.

It will be appreciated by one skilled in the art that the above classifications are not absolute and that an amino acid may be classified in more than one category. In addition, amino acids can be classified based on known behaviour and or characteristic chemical, physical, or biological properties based on specified assays or as compared with previously identified amino acids. Amino acids can also include bifunctional moieties having amino acid-like side chains.

Conservative changes can also include the substitution of a chemically derivatised moiety for a non-derivatised residue, by for example, reaction of a functional side group of an amino acid. Thus, these substitutions can include compounds whose free amino groups have been derivatised to amine hydrochlorides, p-toluene sulfonyl groups, carbobenzoxy groups, t-butyloxycarbonyl groups, chloroacetyl groups or formyl groups. Similarly, free carboxyl groups can be derivatized to form salts, methyl and ethyl esters or other types of esters or hydrazides, and side chains can be derivatized to form O-acyl or O-alkyl derivatives for free hydroxyl groups or N-im-benzylhistidine for the imidazole nitrogen of histidine. Peptide analogues also include amino acids that have been chemically altered, for example, by methylation, by amidation of the C-terminal amino acid by an alkylamine such as ethylamine, ethanolamine, or ethylene diamine, or acylation or methylation of an amino acid side chain (such as acylation of the epsilon amino group of lysine). Peptide analogues can also include replacement of the amide linkage in the peptide with a substituted amide (for example, groups of the formula —C(O)—NR, where R is $(C_1-C_6)$ alkyl, $(C_1-C_6)$ alkenyl, $(C_1-C_6)$ alkynyl, substituted $(C_1-C_6)$ alkyl, substituted $(C_1-C_6)$ alkenyl, or substituted $(C_1-C_6)$ alkynyl) or isostere of an amide linkage (for example, —CH$_2$NH—, —CH$_2$S, —CH$_2$CH$_2$—, —CH=CH— (cis and trans), —C(O)CH$_2$—CH(OH)CH$_2$—, or —CH$_2$SO—).

The compound can be covalently linked, for example, by polymerisation or conjugation, to form homopolymers or heteropolymers. Spacers and linkers, typically composed of small neutral molecules, such as amino acids that are uncharged under physiological conditions, can be used. Linkages can be achieved in a number of ways. For example, cysteine residues can be added at the peptide termini, and multiple peptides can be covalently bonded by controlled oxidation. Alternatively, heterobifunctional agents, such as disulfide/amide forming agents or thioether/amide forming agents can be used. The compound can also be linked to a another compound that can modulate neuronal apoptosis, AMPA receptor endocytosis, synaptic plasticity, learning or memory, or substance abuse or addiction etc. The compound can also be constrained, for example, by having cyclic portions.

Peptides or peptide analogues can be synthesised by standard chemical techniques, for example, by automated synthesis using solution or solid phase synthesis methodology. Automated peptide synthesisers are commercially available and use techniques well known in the art. Peptides and peptide analogues can also be prepared using recombinant DNA technology using standard methods such as those described in, for example, Sambrook, et al.[58] or Ausubel et al.[59] In general, candidate compounds are identified from large libraries of both natural products or synthetic (or semi-synthetic) extracts or chemical libraries according to methods known in the art. Those skilled in the field of drug discovery and development will understand that the precise source of test extracts or compounds is not critical to the method(s) of the invention. Accordingly, virtually any number of chemical extracts or compounds can be screened using the exemplary methods described herein. Examples of such extracts or compounds include, but are not limited plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available. Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla., USA), and PharmaMar, MA, USA. In addition, natural and synthetically produced libraries of, for example, neuronal polypeptides, are produced, if desired, according to methods known in the art, e.g., by standard extraction and fractionation methods. Furthermore, if desired, any library or compound is readily modified using standard chemical, physical, or biochemical methods.

When a crude extract is found to modulate neuronal apoptosis, AMPA receptor endocytosis, synaptic plasticity, learning or memory, or substance abuse or addiction etc., further fractionation of the positive lead extract is necessary to isolate chemical constituents responsible for the observed effect. Thus, the goal of the extraction, fractionation, and purification process is the careful characterization and identification of a chemical entity within the crude extract having neuronal apoptosis, AMPA receptor endocytosis, synaptic plasticity, etc., modulatory activities. The same assays described herein for the detection of activities in mixtures of compounds can be used to purify the active component and to test derivatives thereof. Methods of fractionation and purification of such heterogeneous extracts are known in the art. If desired, compounds shown to be useful agents for treatment are chemically modified according to methods known in the art. Compounds identified as being of therapeutic value may be subsequently analyzed using a mammalian model, or any other animal model for neuronal damage, neural dysfunction, synaptic plasticity, learning or memory, or substance abuse or addiction.

Pharmaceutical Compositions: Dosages, and Administration

Compounds of the invention can be provided alone or in combination with other compounds (for example, nucleic acid molecules, small molecules, peptides, or peptide analogues), in the presence of a liposome, an adjuvant, or any pharmaceutically acceptable carrier, in a form suitable for administration to humans. If desired, treatment with a compound according to the invention may be combined with more traditional and existing therapies for neurological damage, synaptic plasticity, learning or memory, or substance abuse. For example, compounds according to the invention may be administered as combination therapy with other treatments such as free-radical inhibitors to maximise neuronal survival; as complementary therapy to anti-coagulant prophylaxis in subjects undergoing atrial fibrillation or are considered to be at risk for stroke.[86] In some embodiments, the compounds may be administered at specific therapeutic windows. For example, in some embodiments, the compounds may be administered approximately 3 hours after onset of ischemia.

In some embodiments, compounds according to the invention may be provided in fusion with a heterologous peptide to facilitate translocation of the compounds across cell membranes, as for example, described in U.S. Pat. No. 6,348,185; issued to Piwnica-Worms; U.S. Patent Publication US 2003/0229202 (Guo et al.), or PCT publication WO 00/62067 (Dowdy), Becker-Hapak et al.[85], or Kabouridis[114]. In some embodiments, compounds according to the invention may be provided in combination with a carrier peptide, e.g., PEP 1.

In some embodiments, compounds according to the invention may be provided in stem cells, e.g., neuronal stem cells, modified to express the peptide. Suitable cells and vectors for such delivery include viral vectors such as adenovirus, adeno-associated virus, or Herpes Simplex Virus[121,122].

Conventional pharmaceutical practice may be employed to provide suitable formulations or compositions to administer the compounds to patients suffering from or presymptomatic for neurological damage or neural dysfunction. Compounds may be administered systemically or may be administered directly to the CNS or other region of neurological damage. In some embodiments, compounds according to the invention may be provided in a form suitable for delivery across the blood brain barrier. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences" (19$^{th}$ edition), ed. A. Gennaro, 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

For therapeutic or prophylactic compositions, the compounds are administered to an individual in an amount sufficient to stop or slow cell degeneration or apoptosis, or to enhance or maintain synaptic plasticity, depending on the disorder. An "effective amount" of a compound according to the invention includes a therapeutically effective amount or a prophylactically effective amount. A "therapeutically effective amount" refers to an amount effective, at dosages and for periods of time necessary, to achieve the desired therapeutic result, such as reduction of cell degeneration or apoptosis, or to enhance synaptic plasticity. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as inhibition of cell degeneration or apoptosis, or to enhance synaptic plasticity. Typically, a prophylactic dose is used in subjects prior to or at an earlier stage of disease, so that a prophylactically effective amount may be less than a therapeutically effective amount. A preferred range for therapeutically or prophylactically effective amounts of a compound may be 0.1 nM-0.1M, 0.1 nM-0.05M, 0.05 nM-15 µM or 0.01 nM-10 µM.

It is to be noted that dosage values may vary, with the severity of the condition to be alleviated or with the route of administration selected. For example, for oral administration, dosage values may be higher than for intravenous or intraperitoneal administration. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In the case of vaccine formulations, an immunogenically effect amount of a compound of the invention can be provided, alone or in combination with other compounds, with an adjuvant, for example, Freund's incomplete adjuvant or aluminum hydroxide. The compound may also be linked with a carrier molecule, such as bovine serum albumin or keyhole limpet hemocyanin to enhance immunogenicity.

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

Example 1

Materials and Methods

Primary Cultures of Hippocampal Neurons

Hippocampi were rapidly removed from embryonic E 1 8 Sprague Dawley rats and pooled prior to trituration. Hippocampal cell suspensions were plated onto poly-Dlysine coated culture dishes or glass coverslips and grown in Neurobasal™ media 10 (Invitrogen) for 14 days in vitro (DIV). The media from mature 14 DIV neurons was removed and replaced with 100 µM NMDA plus 10 µM glycine for 1 h at 37° C. prior to restoring neurons to the defined growth media. Twenty four hours after NMDA/glycine application, neurons were processed using cell death assays. NMDA-induced $[Ca^{2+}]_i$ responses were evoked and measured using methods described previously[26].

Cell Death Assays

Apoptosis quantification: NMDA-induced apoptosis was quantified either using a Cell Death Detection Elisa Plus Kit (Roche Applied Sciences), which is based on the in vitro determination of cytoplasmic histone-associated DNA fragments, or using TdT mediated addition of biotinylated 11-dUTP to the free 3'-OH ends of DNA. Absorbance readings for both assays were carried out using a microplate reader.

Propidium Iodide (PI) staining of nuclei: After the induction of apoptosis, cells were fixed with 4% parafonnaldehyde/4% sucrose for 10 min followed by ice cold acetone for 1 min, and then stained with 20 mg/ml PI in Dulbecco's PBS for 30 min. Stained coverslips were mounted onto glass slides and viewed with a Leica fluorescence microscope to identify condensed nuclei. Cells with condensed nuclei were counted as apoptotic and the percentage of apoptotic cells to the total number of cells was calculated to give a semi-quantitative analysis, expressed as percentage of apoptosis.

Treatment of Cells with Peptides

A short peptide (YKEGYNVYGIE (SEQ ID NO. 2)) corresponding to amino acid residues from 869 to 879 of the C-terminus of GluR2 (R2-CT) was synthesized and incubated with a carrier protein (Pep-1)23 at a ratio of 1:20 in Dulbecco's modified Eagle's medium (DMEM, Gibco) at 37° C. in a humidified atmosphere containing 5% CO2 for 30 min to allow the formation of R2-CT/Pep-1 complex. Hippocampal neurons (DW 12-14) were then overlaid with the preformed complex to reach a final R2-CT concentration of 1 µM and further incubated for 1 h before experiments commenced.

Receptor Trafficking Assays

Cell ELISA assay: Quantification of cell-surface AMPA or NMDA receptors was performed by a colorimetric cell-ELISA assay essentially as described previously[14]. Briefly, hippocampal neurons were treated with 100 µM NMDA plus 10 µM glycine for 1 h and then fixed with 4% paraformaldehyde/4% sucrose in PBS for 10 min. Half of the cells in each treatment condition were then permeabilized with 0.1% Triton-X 100 for 5 min. Receptors on the plasma membrane surface and the total cellular pool were then determined by incubating the cells with monoclonal antibodies against the extracellular domains of GluR2 or NR1 (Chemicon, 1 µg/ml) overnight at 4° C., followed by incubation with HRP-conjugated anti-mouse IgG secondary antibody (1:1000, Amersham Life Sciences) for 1 h at room temperature. Following extensive washing with PBS, cells were incubated with OPD substrate (Sigma) for approximately 10 min. Reactions were stopped with 0.2 volumes of 3N HCl, and absorbance at 492 nm was read using a spectrophotometric microplate reader.

Transferrin receptor endocytosis assay: To assess the effect of endocytosis inhibitors on transferrin receptor endocytosis, hippocampal neurons were incubated with 2 mg/ml Alexa-A488 conjugated transferrin (Molecular Probes) for 30 min at 37° C. in the presence or absence of endocytosis inhibitors. Internalized receptors were then viewed with a Leica fluorescence microscope.

cDNA Plasmids and Cell Transfection

Rat HA-tagged GluR1 and GluR2 receptor subunit cDNAs have been described previously[14]. Constructs of HA-GluR2 carboxyl internal deletion or truncation mutants were made by standard PCR methods. The HA-GluR23Y-3A mutant was made using a Quick-Change Site Directed Mutagenesis Kit (Stratagene). HEK293 cells (ATCC) were transfected using the calcium phosphate precipitation method. Thirty six to forty eight hours after transfection, cells were washed with extracellular recording solution (ECS in mM: 140 NaCl, 33 glucose, 25 HEPES, 5.4 KCl, 1.3 CaCl2; pH 7.4, 320 mOsm) and incubated in ECS for at least one hour (serum starvation). For insulin treatment, cells were incubated with ECS supplemented with 0.5 µM human recombinant insulin (Sigma) for 10 min, after which the cells were processed for immunocytochemistry and colorimetric assays or lysed in RIPA buffer (50 mM Tris-HCl, 150 mM NaCl and 0.1% triton X-100) for immunoprecipitation as described below.

Cloning, Expression, and Purification of GST Fusion Proteins

GST-GluR23Y and GST-GluR23A were constructed by subcloning corresponding PCR fragments into pGEX 4T-1 vectors. GST fusion proteins were expressed in DH5α *E. coli* and purified from bacterial lysates according to the manufacturer's protocol (Pharmacia). Products were dialyzed in PBS and concentrated using Microcon-10 columns (Amicon) for intracellular application during whole-cell recordings.

Immunofluorescent Confocal Microscopy

HEK293 cells were plated onto poly-D-lysine coated glass cover slips set in 35 mm culture dishes and transfected with 2 µg of the plasmid of interest. For cell-surface receptor expression assays, cells at 48 h post-transfection were fixed with 4% paraformaldehyde in PBS for 10 min. Surface AMPA receptors were first labeled with monoclonal anti-HA antibody (1:2000, Babco, Berkeley, Calif.) and visualized with an FITC-conjugated anti-mouse IgG antibody (1:500, Sigma). For the surface AMPA receptor internalization assay, HEK293 cells transfected with HA-tagged GluR2 constructs were incubated live at 4° C. with monoclonal anti-HA antibody (10:g/ml) for 1 h to label surface AMPA, receptors. Cells were then incubated at 37° C. in ECS supplemented with or without 0.5 µM insulin for 10 min before an additional 20 min incubation in ECS to allow for constitutive or regulated internalization of labeled receptors. Following a 10 min fixation with 4% paraformaldehyde without permeabilization, receptors remaining on the plasma membrane surface were stained with FITC-conjugated anti-mouse IgG antibodies. The internalized cell-surface receptors were subsequently labeled with Cy3-conjugated anti-mouse IgG antibodies following cell permeabilization as described by Man et al.[14]

Calorimetric Assays

Colorimetric assays were performed essentially as previously reported.[14]

Immunoprecipitation and Western Blotting

Immunoprecipitation and Western blotting were carried out essentially as previously reported.[14] Proteins from cerebral cortex, hippocampal slices, cultured hippocampal neurons or transfected HEK293 cells were solubilized in RIPA buffer containing either 1% SDS (plus 5 min boiling; denaturing conditions) or 1% DOC (non-denaturing conditions). For immunoprecipitation, 500 µg of protein from these tissue lysates was incubated with their respective antibodies in 500 µl of RIPA buffer for 4 h at 4° C. Protein A-sepharose was added to the mixture and incubated for an additional 2 h. The complex was isolated by centrifugation and washed three times. Proteins eluted from the sepharose beads were subjected to SDS-PAGE and immunoblotting using their respective antibodies. For sequential re-probing of the same blots, the membranes were stripped of the initial primary and secondary antibodies and subjected to immunoblotting with another antibody. Blots were developed using enhanced chemiluminescence detection (Amersham). Band intensities were quantified using Scion Image PC software.

Hippocampal Neuron Cultures, Transfection, and Fluorescence-Based Internalization Assays As in Lee et al., 2002[40]; Passafaro et al., 2001.[49]

Electrophysiological Recording

Hippocampal slices (400 µm thickness) were prepared from Sprague-Dawley rats aged 16-26 postnatal days and perfused at room temperature with artificial cerebrospinal fluid containing (mM): 126 NaCl, 26 NaHCO3, 10 glucose, 3 KCl, 1.2 KH2PO4, 1 MgCl2, and 1 CaCl2, saturated with 95% O2/5% CO2[14]. The recording pipettes (4-5 MO) were filled with solution containing (mM): 135 CsCl, 10 HEPES, 5 QX-314, 4 Mg-ATP, 2 MgCl2, 0.5 EGTA, 0.2 GTP and 0.1 CaCl2, pH 7.4, 310 mOsm. Whole-cell recording of CA1 neurons and the induction of LFS-LTD were performed as previously described.[14]

Statistical Analysis

Student's t-tests were used whenever intra-experiment samples were compared. For cross comparisons or analysis of data between experiments all values were first subjected to a one-way ANOVA and all groups were compared against control basal values. Values were not statistically significant at $F > 0.5$. Groups that were found to be statistically significant were individually compared using Dunnett's t-test. All analysis was done using normalized values in the Statistica statistics package (Statsoft).

Primary Neuronal Culture

The cortex was dissected from 18 days in utero Wistar embryos and was treated with trypsin-EDTA for 15 min at 37° C. The cells were then washed 3 times and triturated to a single cell suspension. The neurons with glia were then seeded at a density of ~2.5×10$^5$ neurons/well in 12 well tissue culture plates coated with poly-D lysine. The cells were then cultured for 24-48 h in plating media (Gibco Neurobasal™, 1% FBS, 2% B-27 supplement, 0.5 mM L-glutamate, and 25 µM glutamic acid), after which the cells were treated with Neurobasal™ maintenance media (NMM: Gibco Neurobasal™ Media+0.5 mM L-glutamate, 2% B-27 supplement) with 10 µM 5-Fluoro-2'-deoxyuridine (FDU) to enrich the culture for neurons (~85%). After 24 h-48 h culture in FDU, the cells were maintained on NMM changed every 4 days.

Peptide Generation

Tat-GluR2-3Y, Tat-GluR2-3A, and dansyl-conjugated Tat-GluR2-3Y were all synthesized on an ABI 433A peptide synthesizer (NAPS).

Neuronal Uptake of Dansyl-Labeled Tat-GluR2-3Y Peptide

Day in vitro (DIV) 13 primary cortical neurons at a density of 2.5×10$^5$/well in 12 well plates were washed once with extracellular solution (ECS: 140 mM NaCl, 5.4 mM KCl, 1.3 mM CaCl$_2$, 10 mM HEPES, 33 mM D-glucose, pH 7.4) and then 1 mL containing either no peptide (control) or 1 µM dansyl labeled-Tat-GluR2-3Y was added to the wells. After 5 min, 10 min, 30 min, or 60 min incubation at 37° C. the wells were washed twice with ECS and imaged using fluorescence microscopy using an excitation wavelength of 550 nm.

Quantification of AMPAR Endocytosis in Response to NMDA Treatment

Using cellular ELISA, the amount of intracellular versus extracellular AMPAR expression was measured allowing quantification of AMPAR endocytosis in response to NMDA insult. DIV 12-13 neurons were washed once with room temperature ECS. 1 mL of NMM with or without 1 µM Tat-GluR2-3Y or Tat-GluR2-3A peptide was added to the wells and the cells were incubated for 1 h at 37° C. The media was then aspirated and 1 mL of ECS with, different combinations of peptide (1 µM Tat-GluR2-3Y or Tat-GluR2-3A) and NMDA-glycine treatment (50 µM NMDA+10 µM glycine) was added to the wells and the cells were incubated at room temperature for 30 min. The wells were then washed once with ECS and then immediately fixed with 0.5 mLs of cold fixative (4% paraformaldehyde, and 4% sucrose in PBS) for 10 min with shaking. The cells were then washed 3 times with 1 mL of PBS. Half of the wells for each treatment group were left unpermeabilized (representing the extracellular AMPAR expression) and half were permeabilized (representing total intracellular and extracellular AMPAR expression) with 0.5mLs of 0.2% Triton X 100 in PBS for 10 min with shaking followed by 3 PBS washes. The wells were then blocked with 2% goat serum in PBS for 1 h. After blocking the blocking buffer was aspirated and either 400 µL of 1 ug/mL of mouse anti-rat GluR2 N-terminus antibody in 2% goat serum (clone: 6C4, Chemicon) or 400 µL of blocking buffer (no primary antibody controls) was added to the wells and the plates were incubated overnight with shaking at 4° C. The plates were then washed 3 times with PBS and 400 µL of 1/1000 horseradish peroxidase-conjugated sheep anti-mouse IgG2a antibody in 2% goat serum was added and the plates were incubated for 1 h at room temperature with shaking. The plates were then washed 3 times with PBS, then 1 mL of OPD solution (0.4 mg/mL o-phenylenediamine, 0.4 mg/mL urea hydrogen per-oxide, and 50 mM phosphate-citrate buffer, Sigma) was added and the plates were incubated for 5-10 min at room temperature with shaking. The peroxidase reaction was terminated by the addition of 200 µL of 3N HCl. The absorbance at 492 nm was read using a µQuant plate reader (Bio-Tek Instruments Inc.). The data were analyzed by first subtracting the absorbance values for the no-primary controls from the other samples. The percentage AMPAR surface expression was then expressed as a ratio of the non-permeabilized samples to the permeabilized samples. The individual repeat experiments were then normalized and treatment groups were compared using ANOVA followed by the Tukey-Kramer test, (p=0.05).

Quantification of Neuronal Apoptosis in Oxygen and Glucose Deprivation (OGD)

Neurons were subjected to 60 min of oxygen and glucose deprivation and the apoptosis was quantified using a mono- and oligonucleosome ELISA. DIV 13 neurons seeded at a density of $2.5 \times 10^5$/well in 12 well plates were washed once with ECS, and the cells were pretreated for 60 min with or without 1 µM Tat-GluR2-3Y in NMM. The cells were then washed twice with either OGD buffer (121 mM NaCl, 5 mM KCl, 1 mM, Na-pyruvate, 1.8 mM $CaCl_2$, 25 mM $NaHCO_3$, 0.01 mM glycine; pH 7.4) for the OGD samples, or with ECS for the non-OGD samples. The non-OGD samples were then incubated for 25 h at 37° C. in NMM and the OGD samples were incubated in OGD buffer with or without Tat-GluR2-3Y in an anaerobic chamber at 37° C. for 60 min. The OGD samples were then incubated for 24 h at 37° C. in NMM. The neuronal apoptosis was then quantified using a Cell Death Detection ELISA$^{PLUS}$ kit (Roche Applied Science) as per the manufacturer's instructions. The absorbance at 405 nm (reference wavelength, 490 nm) was read using a µQuant plate reader (Bio-Tek Instruments Inc.). The individual repeat experiments were then normalized and treatment groups were compared using ANOVA followed by the Tukey-Kramer test, (p=0.05).

Tat-GluR2-3Y Infiltration of Brain Tissue

Two adult male C57-Black/6 mice weighing ~22 g were given an intraperitoneal injection of either saline or 30 nmol/g of dansyl-labeled Tat-GluR2-3Y. The mice were sacrificed at 2 h and the brains were immediately removed and frozen at −80° C. 40 micron coronal sections were cut with a cryostat and visualized with fluorescence microscopy.

Transient Focal Ischemia Model

The procedure was performed essentially as described previously (70). Briefly, adult male Sprague-Dawley rats between 280 and 320 g (20 h fasted weight) were anesthetized with an inhaled mixture of 4% isoflurane, in 30% oxygen balanced nitrous oxide, and maintained on 1.5% isoflurane. Bronchial secretions were minimized by administering 0.5 mg/kg of atropine intraperitoneally. Either, 3 nmoles/g of Tat-GluR2-3Y in saline, 3 nmoles/g Tat-GluR2-3A in saline, or saline only was administered 1 h before middle cerebral artery (MCA) occlusion, via a femoral vein PE-50 catheter. The experimenter was blinded to the identity of the treatment groups for all surgeries and down-stream experiments. Under a dissection microscope, the common carotid artery (CCA), external carotid artery (ECA), and internal carotid artery (ICA) were exposed and dissected. The terminal lingual and maxillary arteries were then cauterized and the pterygopalitine artery was then ligated with 5-0 silk suture. After this point the ICA was the only remaining extracranial branch of the CCA. The ECA was then partially cut close to the rostral ligature and a 30 mm 3-0 nylon monofilament with a heat rounded tip was inserted into the ECA and advanced past the CCA bifurcation. The ECA was then completely cut, mobilizing the ECA stump containing the nylon suture. The nylon suture was then flipped so that its tip was facing the ICA and the nylon suture was then gently advanced approximately 20 mm until resistance was felt. At this point the suture reached the origin of the MCA and the anterior cerebral artery completely blocking the blood flow to the MCA territory. The wound was then stitched closed with silk suture and the animal was awoken by turning off the isoflurane. Rectal temperature, and blood pressure measured with a tail cuff were measured before treatment, 15 min post injection, 50 min post injection, and 15 min post MCA occlusion. The plasma pH, $O_2$, and $CO_2$ were measured with a Rapidlab™ 348 blood gas analyzer (Bayer Diagnostics) in some animals to ensure that the gas flow rates used were appropriate and yielded reproducible blood gases. The animal was then given a neurological examination after 45 min of MCA occlusion. This exam was used to exclude any animal that did not experience significant occlusion of the MCA. The examination consisted of 10 tests with a maximum deficit score of 23 (71). The individual tests are summarized in Table II.

TABLE II

Summary of neurological scoring.

| Test | Description | Score |
|---|---|---|
| Postural reflex: | | |
| Degree of twisting | Degree of body rotation towards parietic side when held by tall. | 0-2 |
| Degree of forelimb flexion | Degree of forelimb flexion when held by tall. | 0-2 |
| Gate disturbances | Circling or walking towards parietic side, or other gate disturbances. | 0-5 |
| Tall pull | Biased movement towards one side when tall is pulled. | 0-2 |
| Lateral resistance to push | Degree of lateral resistance to push. | 0-2 |
| Visual placing: | | |
| Forward | Presence of a forelimb placing reflex in response to a forward visual cue. | 0-2 |
| Lateral | Presence of a forelimb placing reflex in response to a lateral visual cue. | 0-2 |
| Tactile placing: | | |
| Forward | Presence of a forelimb placing reflex in response to a tactile stimulus on dorsal surface of paw. | 0-2 |
| Lateral | Presence of a forelimb placing reflex in response to a tactile stimulus on lateral surface of paw. | 0-2 |
| Proprioceptive placing | Presence of a forelimb placing reflex in response to being held by hind quarters above surface. | 0-2 |
| Total score | | 0-23 |

The animal was induced again after the neurological examination and the nylon monofilament was withdrawn at 60 min after the onset of occlusion returning blood flow to the MCA territory. The neurological examination was performed again at the time of sacrifice (~24 h). The sham surgery was performed as the MCA occlusion, however, the nylon monofilament was not inserted.

TTC Staining

Rats were sacrificed 3 days post MCA occlusion by deep anesthesia followed by decapitation. The brain was removed immediately after sacrifice and placed in an acrylic rat brain matrix (Harvard Apparatus) and incubated at −80 C for 5 min. 1 mm coronal slices were then cut with razor blades and placed in 37 C solution of 2% 2,3,5-triphenyltetrazolium chloride (TTC, Sigma) in PBS. The slices were then incubated for approximately 15 min until sufficient colour developed.

TUNEL Staining

At day 1 post MCAo rats were anesthetized with 1.5 mL of 25% urethane and were perfused with 100 mL of 0.9% saline followed by 120 mLs of 4% paraformaldehyde in PBS. The brains were then removed and stored overnight at 4° C. in 4% paraformaldehyde. The brains were then transferred to a 30% sucrose and 0.1% sodium azide, in PBS solution and stored at 4° C. until the brains completely sunk. The brains were then frozen in dry ice and 12 micron coronal slices were cut with a cryostat at −0.8 mm with respect to the bregma using a free floating method (72). The slices were then mounted on glass slides and stained with TMR-TUNEL (terminal deoxyribonucleotide transferase [TdT]-mediated dUTP nick end labeling) (Roche Applied Science) as per the manufacturer's instructions. The slices were scored for number of cells that stained positive for TMR-TUNEL per field of view at 10× magnification. For each section the same 3 fields along the lateral portion of the cortex on the affected hemisphere were scored (the affected hemisphere was defined as the side with the greatest amount of apoptosis).

Example 2

NMDA-Induced Apoptosis Requires AMPA Receptor Endocytosis

In order to induce apoptosis in mature cultures of rat hippocampal neurons (14 DIV+) we treated cells with a mild NMDA insult of 100 μM NMDA with 10 μM glycine for 1 h followed by recovery of the cells in normal media for periods of up to 24 h. As shown in FIG. 1A, B, NMDA treatment induced a time-dependent increase in caspase-3 activity, a biochemical indicator of neuronal apoptosis, as detected by ELISA assay of DEVD-pNA cleavage. This increase in caspase-3 activity peaked between 12-24 h after the treatment, at which time the majority of neurons were either dying or dead, exhibiting the hallmarks of apoptotic cell death, including DNA laddering demonstrated by gel electrophoresis of extracted DNA (FIG. 1C), and nuclear condensation with disintegrating processes shown by nucleons staining with propidium iodide or intercalating DNA dye, Hoechst 33258 (bisbenzimide). The degree of neuronal apoptosis was also quantified by measuring internucleosomal cleavage of DNA with both 11-dUTP (FIG. 1E) and histone biotinylation assays (FIG. 1F). In contrast, in non-treated cultures there was little apoptosis detectable either biochemically or morphologically (FIG. 1A-F). Furthermore, the NMDA-induced apoptosis was a result of specific activation of NMDA receptors, as it was fully blocked by the NMDA receptor antagonist, APV (50 μM; FIG. 1D). Therefore, NMDA treatment produced neuronal apoptosis.

In order to determine the role of NMDA-induced endocytosis in mediating neuronal apoptosis, we first examined the effect of hypertonic sucrose, a well-characterized clathrin-dependent endocytosis inhibitor that inhibits the assembly of clathrin-coated pits[13;14]. As shown in FIG. 1E, when cells were treated with hypertonic sucrose (0.4 M), prior to the application of NMDA and in its presence for 1 h, we found that apoptosis was dramatically reduced. While hypertonic sucrose has been widely used as an effective inhibitor of clathrin-mediated endocytosis, it may have many actions other than inhibiting endocytosis. To further establish an essential role of stimulated endocytosis in NMDA-induced apoptosis, we also examined the effect of another specific inhibitor for clathrin-dependent endocytosis. The inhibitor is a short, dynamin-derived, myristoylated peptide that is membrane permeable (myr-Dyn). It blocks the recruitment of dynamin to clathrin-coated pits by amphiphysin, thereby inhibiting clathrin-mediated endocytosis[15]. Indeed, incubation of neurons with myr-Dyn (100 μM) was found to be as effective as hypertonic sucrose in reducing NMDA-induced apoptosis (FIGS. 1E and F), In contrast, control Dyn peptides, both non-myristoylated (non-membrane permeant) Dyn (Dyn; FIG. 1E) and scrambled myr-Dyn (s-myr-Dyn; FIG. 1F), had little effect. Thus, facilitated clathrin-dependent endocytosis is necessary for NMDA receptor-mediated apoptosis. In order to test whether the effects of endocytosis inhibition were specific to NMDA-induced apoptosis, we next tested the effect of these inhibitors on a well-characterized neuronal apoptosis model that is induced by treating neurons with the kinase inhibitor staurosporine (STS; 100 nM, 1 h)[12]. As shown in FIG. 1E, we found that both endocytosis inhibitors failed to significantly alter the STS-induced neuronal apoptosis. Therefore, clathrin-mediated endocytosis is specifically required for neuronal apoptosis induced by NMDA receptor activation.

To rule out the possibility that these endocytosis inhibitors may have prevented neuronal apoptosis by interfering with NMDA receptor channel function, and hence $Ca^{2+}$ influx through the activated channel, we loaded hippocampal neurons with the intracellular Ca2+ dye, Fura-2, and then monitored the calcium influx evoked by repetitive local 'puff' application of NMDA (100 μM; 500 ms) to neurons before and during hypertonic sucrose treatment. As summarized in FIG. 2A, B, sucrose at concentrations that inhibited endocytosis and apoptosis did not significantly alter NMDA-evoked $[Ca^{2+}]_i$ responses. The fact that inhibition of endocytosis blocked NMDA-induced apoptosis without affecting its $[Ca^{2+}]_i$ responses indicates that intracellular increases in $[Ca^{2+}]_i$ concentrations, although necessary[3;4], may not be sufficient to produce NMDA-induced apoptosis.

Activation of certain forms of caspases, such as caspase-3 and -7[16] (also FIG. 1A, B) has been implicated in NMDA-induced neuronal apoptosis. We therefore investigated the effects of inhibiting endocytosis on NMDA dependent activation of caspase-3. NMDA treatment dramatically increased the level of the activated form of caspase-3 as demonstrated by Western blots using an antibody that specifically recognizes only activated/cleaved caspase-3 (FIG. 2C). The membrane permeable myr-Dyn, at the concentration that inhibits NMDA receptor-mediated apoptosis, efficiently inhibited NMDA-mediated caspase-3 activation (FIG. 2C).

The serine/threonine kinase Akt/PKB has been implicated in protecting neurons from apoptotic cell death[17] and inhibition of this kinase activity has been suspected to be involved in NMDA receptor-mediated apoptosis[18]. We investigated whether the endocytosis process plays a critical role in the inhibition of Akt activity by determining the level of Akt phosphorylation at serine 473, a residue whose phosphorylation is required for full activation of Akt[19]. As shown in FIG. 2D, treatment of neurons with NMDA resulted in a significant reduction in S473 phosphorylated Akt and hence Akt activity, without altering levels of total Akt. This reduction in Akt activity was largely prevented by the inhibition of endocytosis with hypertonic sucrose. In contrast, sucrose treatment had no effect on the reduction of Akt phosphorylation following STS treatment, further supporting the specific involvement of endocytosis in NMDA-induced apoptosis (FIG. 2D). Thus, stimulated endocytosis appears an obligatory step that is down stream of rising in $[Ca^{2+}]_i$ and upstream of caspase activation and Akt inhibition in NMDA-induced neuronal apoptosis.

Figure 3B:
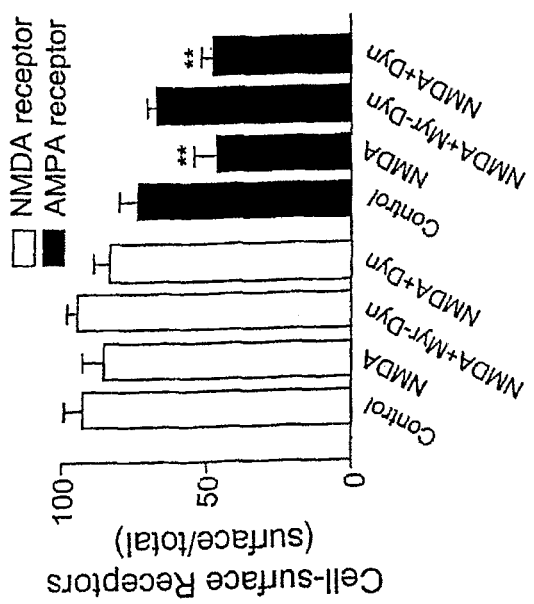

A significant reduction of cell-surface AMPA, but not NMDA, receptors was observed following NMDA treatment and this reduction was a result of facilitated receptor endocytosis as it was blocked by endocytosis inhibitor myr-Dyn, but not the control peptide, Dyn (FIG. 3A). To investigate whether there was a direct link between the NMDA-induced AMPA receptor endocytosis and apoptosis, a peptide derived from the short amino acid sequence between residues tyrosine 869 and glutamic acid 879 within the carboxyl terminal (CT) region of the GluR2 subunit of the AMPA receptor (YKEGYNVYGIE; termed R2-CT) was delivered into cultured neurons by mixing it with a carrier peptide (Pep-1)[23] one hour prior to and during the NMDA treatment. The results indicated that the NMDA-induced reduction of cell-surface AMPA receptors was prevented (FIG. 3B).

In order to be sure that the blockade by this peptide was not due to non-specific effects on the endocytotic process, we examined its effect on transferrin receptor endocytosis, a well-characterized clathrin-mediated receptor endocytosis[13]. Incubation of hippocampal neurons with fluorescently-labeled transferrin for 30 min resulted in an accumulation of the fluorescently-labeled transferrin in the intracellular compartment. This was a result of clathrin-mediated transferrin receptor endocytosis as it was eliminated when 0.4 M sucrose was also present during the period of transferrin incubation. In contrast, R2-CT+Pep-1, applied to these neurons one hour prior to and during the transferrin incubation, failed to prevent transferrin receptor endocytosis. Thus, the R2-CT peptide is a dominant inhibitor that can specifically block NMDA-induced AMPA receptor endocytosis, but not non-specifically affect clathrin-mediated endocytotic processes.

Furthermore, pre-treatment of the neurons with R2-CT+Pep-1 significantly reduced NMDA-induced apoptosis as quantified by the histone biotinylation assay (FIG. 4A), and by PI nuclear staining (FIG. 4B). PI staining after fixation showed that R2-CT blocked NMDA-induced apoptosis. In this particular example, neither R2-CT nor Pep-1 alone had any detectable effect on NMDA-induced apoptosis. Similar to the general blockade of the clathrin-mediated endocytotic process with either sucrose or myr-Dyn, interfering with AMPA receptor endocytosis by R2-CT did not alter STS-induced neuronal apoptosis (FIG. 4A). Taken together, our results have provided strong evidence for an obligatory requirement for AMPA receptor endocytosis in mediating NMDA-induced neuronal apoptosis.

Therefore, a clathrin-dependent AMPA receptor endocytosis is specifically required for NMDA-, but not STS-, induced apoptosis of hippocampal neurons maintained in primary culture. Blocking endocytosis has no effect on NMDA-induced $Ca^{2+}$ responses, but prevents both NMDA-induced activation of caspase-3 and inhibition of Akt phosphorylation. Thus, AMPA receptor endocytosis may be a critical link between NMDA-induced $[Ca^{2+}]_i$ overload and intracellular cascades leading to apoptosis.

Thus, stimulation of NMDA receptor activates intracellular signaling cascades leading to apoptosis, and facilitates dynamin-dependent internalization of the AMPA subtype glutamate receptors. Blocking the dynamin-dependent internalization specifically ameliorated NMDA (but not staurosporine)-activated apoptotic cascades, without affecting NMDA-induced rises in $[Ca2+]_i$. Specific inhibition of NMDA-induced AMPA receptor endocytosis by a GluR2-derived peptide prevents NMDA induced apoptosis, without affecting that produced by staurosporine. These results demonstrate that AMPA receptor endocytosis may be required in linking NMDA receptor activation to neuronal apoptosis, and thereby suggests that AMPA receptor endocytosis plays an essential role in reducing synaptic strength, and also actively mediates other important intracellular pathways, including apoptotic cell death.

Example 3

Distinct Sequences within the GluR2 Carboxyl Terminus are Required for Constitutive and Regulated AMPA Receptor Endocytosis To identify sequence determinants for constitutive and insulin-stimulated AMPA receptor endocytosis, we made six GluR2 mutants containing various deletions of the GluR2 CT (FIG. 5B). All constructs, except GluR2Δ854, were HA-tagged in the extracellular amino-terminal region. Following transient transfection into HEK293 cells, these constructs were expressed at a level comparable to their wild-type counterparts, HA-GluR2 or GluR2, as determined by a colorimetric cell-ELISA assay under permeabilized cell conditions (FIG. 5C).

Figure 6A:
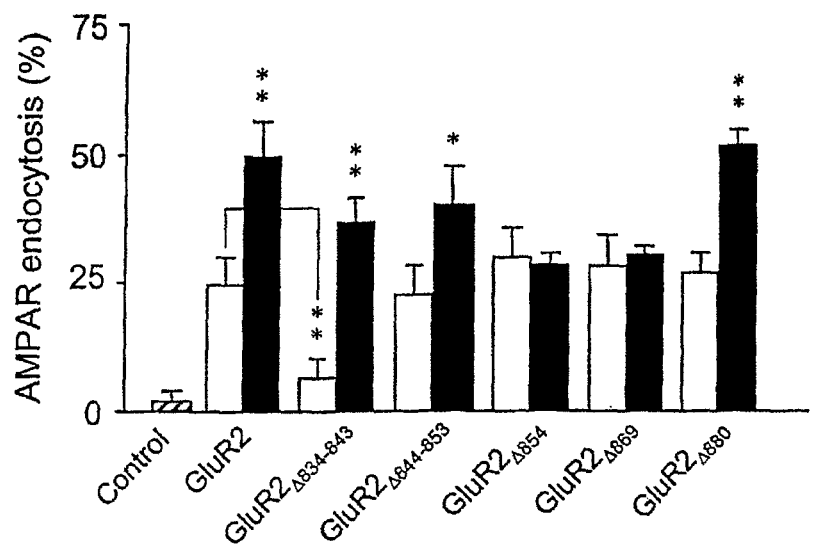
FIGS. 6A-B. Effects of GluR2 CT mutations on endocytosis and cell-surface expression of AMPA receptors. A. Quantitation of the changes in constitutive (Basal) and regulated (Insulin) endocytosis of GluR2 and its various mutants using a colorimetric ELISA assay with pre-labeled cells following the internalization of the receptors over 30 min (% AMPAR endocytosis=100%—remaining cell-surface receptors/total number of receptors; n=6). Control: internalization measured in cells at 4 E C without any 37 E C exposure (under these conditions, both constitutive and regulated endocytosis is blocked). B. Cell-surface AMPA receptors in HEK293 cells transiently expressing GluR2 and its various mutants were quantitated using colorimetric cell-ELISA based cell-surface receptor assays (n=6). Statistical comparisons were made between basal and insulin-treated conditions, except where indicated by lines. *p<0.05, **p<0.01

The ability of these mutants to undergo both constitutive and regulated endocytosis was assayed as described previously.[14] Surface receptors in live cells were pre-labelled with an anti-HA antibody (or an antibody against the extracellular N-terminal domain of GluR2 in the case of GluR2Δ854) at 4° C. (which blocks endocytosis). Surface labelled cells were then incubated at 37° C. for 30 min to allow endocytosis to resume both in the absence and presence of insulin (0.5 μM) to determine changes in constitutive (basal) and regulated (insulin-stimulated) AMPA receptor endocytosis, respectively (FIG. 6A, B). Internalised receptors were then visualised by confocal microscopy and quantitated by colorimetric cell-ELISA-based receptor internalization assays (FIG. 6A). Representative confocal images of HEK293 cells transiently transfected with HA-tagged GluR2 or GluR2 mutants were obtained. Transfected cells were pre-labeled with anti-HA antibody and then receptor endocytosis was evaluated under basal conditions (constitutive endocytosis) or following insulin stimulation (0.5 μM, 10 min; regulated endocytosis). Cell surface receptors were stained with FITC under non-permeant conditions and internalized receptors were subsequently stained with Cy3 after cell permeabilization. In order to determine whether changes in internalization produced by these mutations were able to alter surface receptor numbers, we also measured the steady-state level of cell-surface AMPA receptors using colorimetric cell-ELISA-based cell-surface receptor assays (FIG. 6C).

Figure 6B:
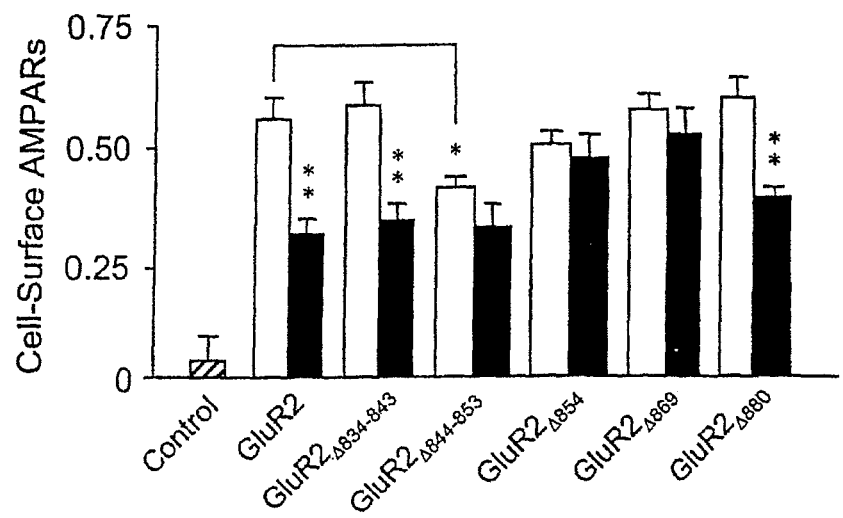

As shown in FIG. 6A, wild type GluR2 receptors underwent both constitutive and insulin stimulated endocytosis. Thus, in the absence of insulin, approximately 25% of the cell-surface receptors were endocytosed within 30 min and this proportion was increased to 48% following brief insulin stimulation (0.5:M, 10 min). This facilitated endocytosis was associated with a significant reduction in the level of AMPA receptors expressed on the cell surface (FIG. 6B). Truncation of the last four amino acids (GluRΔ880), which form the PDZ binding motif, did not have any observable effects on either constitutive or regulated endocytosis. However, truncation of the last 30 (GluR2Δ854) or 15 residues (GluR2Δ869) completely abolished the insulin-induced AMPA receptor endocytosis, and the reduction in its cell-surface expression (FIGS. 6A-B). Neither truncation altered the degree of constitutive AMPA receptor endocytosis (FIG. 6A) or the basal level of receptor expression on the cell surface (FIG. 6B). A significant decrease in the rate of constitutive internalisation of GluR2Δ834-843, in which the first 10 amino acids of the GluR2 CT were deleted, was observed (FIG. 6A). However, this internal deletion did not alter the steady-state number of AMPA receptors expressed on the cell surface (FIG. 6B). Nor did it alter the responsiveness to insulin, as GluR2Δ834-843 showed enhanced internalization similar in magnitude to wild-type GluR2 (FIGS. 6A and 6B). On the other hand, the internal deletion mutant GluR2Δ844-853 showed no significant change in the degree of constitutive endocytosis (FIG. 6A), but exhibited a small decrease in insulin-stimulated endocytosis (FIG. 6A) and a reduction in the steady-state receptor level on the cell surface (FIG. 6B).

Example 4

GluR2 CT Tyrosine Phosphorylation is Required for Insulin Stimulated AMPA Receptor Endocytosis The R2-CT sequence contains three tyrosine residues. To determine whether these tyrosine residues are substrates of certain tyrosine kinases, we performed in vitro kinase assays using active recombinant Src and glutathione S-transferase (GST)-fusion proteins of the carboxyl tails of GluR1 (GST-GluR1CT) and GluR2 (GST-GluR2CT) (FIG. 7A). GST-GluR2CT, but not GST-GluR1CT or GST alone, is specifically phosphorylated by Src kinase. Consistent with the hypothesis that one or more of the tyrosine residues is the substrate(s) for the Src phosphorylation, we found that the recombinant Src kinase phosphorylated a GST fusion protein containing the nine amino-acid stretch including all three GluR2-unique tyrosine residues (GST-Y869KEGY873NVY876G). Src-mediated phosphorylation was abolished when these tyrosine residues were mutated into alanines (GST-A869KEGA873NVA876G).

To determine whether these GluR2 CT tyrosine residues are phosphorylated in situ by endogenous tyrosine kinase activity in response to insulin stimulation, we generated a GluR2 subunit mutant in which tyrosine residues Y869, Y873 and Y876 were mutated into alanines (HA-GluR23Y-3A). When transiently expressed in HEK293 cells, the mutant was expressed at the same level as its wild type GluR2 counterpart (FIG. 7B). We first examined the potential phosphorylation of these tyrosine residues in situ in cells transiently expressing HA-GluR2, HA-GluR23Y-3A, or HA-GluR1. Cells were treated with or without insulin (0.5 μM, 10 min) and then homogenized as detailed in the methods section. The expressed AMPA receptor complexes were immunoprecipitated using an anti-HA antibody under denaturing conditions and then immunoblotted for their level of tyrosine phosphorylation using an anti-phosphotyrosine antibody. The results demonstrate that there was a detectable level of basal tyrosine phosphorylation of wild type GluR2 and that the level of phosphorylation increased following brief treatment with insulin (FIG. 7C). The triple Y-to-A mutation strongly decreased both basal and insulin-induced tyrosine phosphorylation of HA-GluR2. In contrast, there was almost no detectable tyrosine phosphorylation of GluR1 under either basal or insulin-stimulated conditions (FIG. 7C). These results suggest that tyrosine phosphorylation of GluR2 CT occurs in a cellular context under basal conditions, and is enhanced by insulin.

Figure 7D:
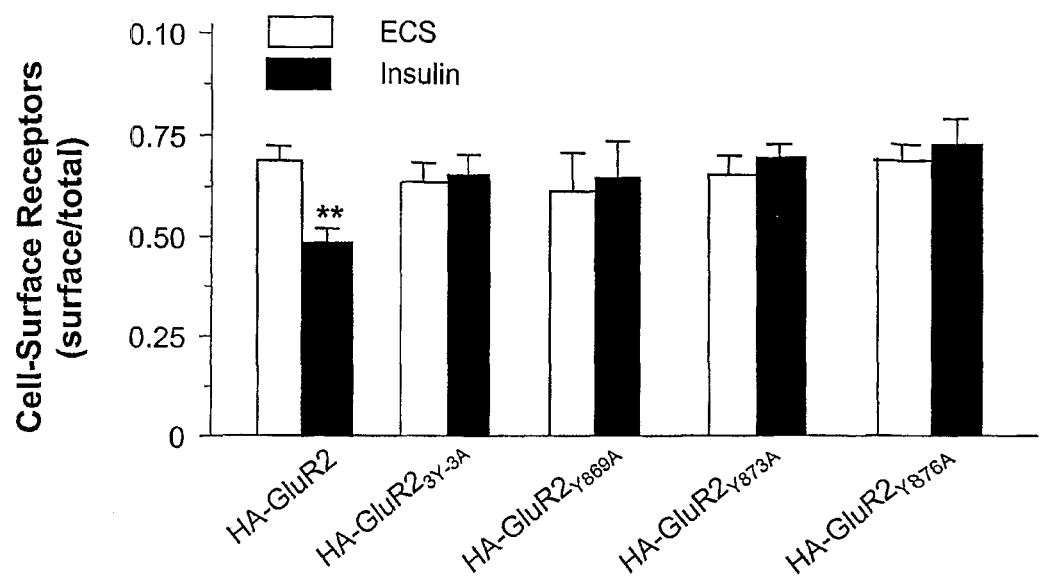
FIGS. 7 A-D. Insulin increases phosphorylation of tyrosine residues within the GluR2 carboxyl terminal (CT) region. A. In vitro tyrosine phosphorylation of the GluR2 CT. GST fusion proteins of the GluR1 CT (GST-GluR1CT), the GluR2 CT (GST-GluR2CT), residues 869-876 (YKEGYNVYG (SEQ ID NO. 4)) of the GluR2 CT (GST-GluR23Y), which contains a cluster of three tyrosine residues (Y869, Y873, and Y876) and the same amino acid stretch of the GluR2 CT with its tyrosine residues replaced by alanines (GST-GluR23A), along with the GST back bone (GST) as control, were incubated in the absence (−) or presence (+) of active recombinant pp60 c-Src. Phosphorylation products were immunoblotted using an anti-phosphotyrosine antibody (top panel). Ponceau S staining of the same blot showed that a similar amount of GST fusion protein was used in each of the reactions (lower panel). B. Expression levels of HA-GluR2 and HA-GluR23Y-3A (where tyrosines 869, 873 and 876 were mutated to alanines) 48 h after transient transfection into HEK293 cells were determined by a cell ELISA assay using permeabilized cells. C. HEK293 cells transiently transfected with HA-GluR1, HA-GluR2 or HA-GluR23Y-3A, along with empty vector (mock transfection) as control. Forty-eight hours later, the cells were treated with or without 0.5 μM insulin for 10 min. The lysates were then subjected to immunoprecipitation with an anti-HA antibody under denaturing conditions and immunoblotting with an anti-phosphotyrosine antibody (Top blot; IB: PY). The same blot was stripped and re-immunoblotted with the anti-HA antibody to ensure similar immunoprecipitation efficiency in all individual experiments (lower blot; IB: HA). D. Mutation of individual tyrosines of the Glu23Y-CT peptide to alanines.

Mutation of tyrosine residues of GluR2-CT prevents insulin-induced reduction of cell-surface AMPA receptors. HEK cells expressing wild type GluR2 or GluR2 Y-A mutants were treated with insulin (0.5 μM) for 10 min and with an additional 20 min incubation period in ECS. Level of cell-surface receptors were assayed using colorimetric assay. Mutation of any one of the tyrosine residues was sufficient to prevent the insulin-induced reduction in cell-surface AMPA receptor expression (FIG. 7D). Without wishing to be bound by any hypothesis, these results may suggest that all three tyrosine residues are substrates of tyrosine phosphorylation, or that they are all involved in substrate recognition by the kinase, or some other aspect of the catalyzed phosphorylation such that mutation of a particular tyrosine could prevent phosphorylation even if it is not the direct target of phosphorylation. Thus, in the latter case, mutating any of the non-substrate tyrosine residues would affect substrate-kinase interaction and hence be able to prevent phosphorylation of the substrate tyrosine residue, thereby reducing stimulated receptor endocytosis.

Figures 8A, 8B:
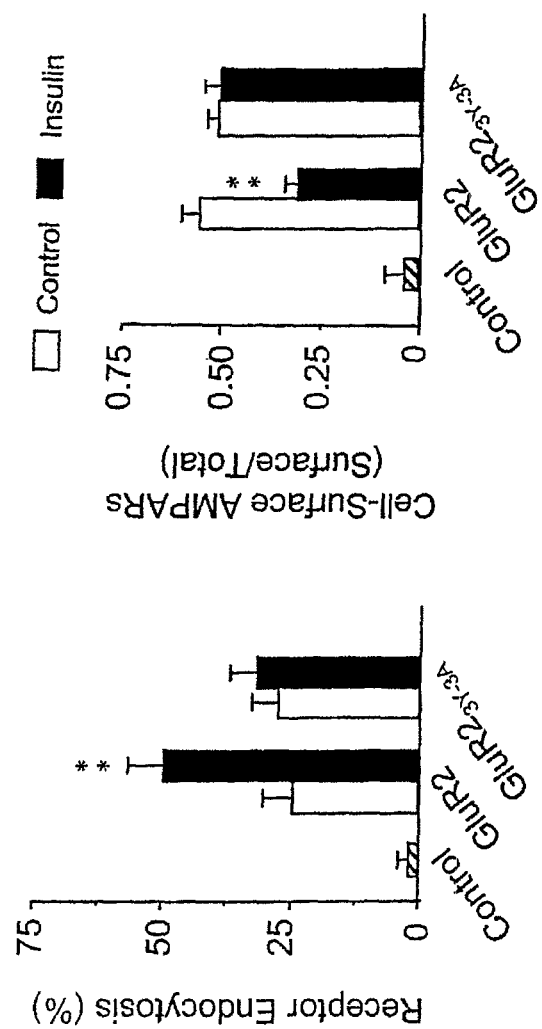
FIGS. 8A-B. The tyrosine cluster in the GluR2 CT is required for regulated, but not constitutive, AMPA receptor endocytosis in HEK293 cells. A. Colorimetric cell-ELISA receptor endocytosis assays were performed with (Insulin) or without (Control) stimulation (see FIG. 2) on HEK293 cells transiently transfected with wild type HA-GluR2 subunit or HA-GluR23Y-3A, in which tyrosine residues Y869, Y873 and Y876 were mutated into alanines. B. Colorimetric cell-ELISA cell-surface receptor assay results of HEK293 cells transfected and treated as in (A). Results were obtained from 6 experiments for each individual group. **p<0.01

The functional significance of GluR2 CT tyrosine phosphorylation with respect to insulin-stimulated endocytosis was tested by assaying internalization of HA-GluR2 and HA-GluR23Y-3A in HEK293 cells (FIG. 8A, B). While mutation of these tyrosine residues did not alter the steady-state level of GluR2 expressed on the cell surface (FIG. 8B), it did block the insulin-induced endocytosis (FIG. 8A) and insulin-induced reduction in the level of cell-surface AMPA receptors (FIG. 8B).

Example 5

Figure 9B:
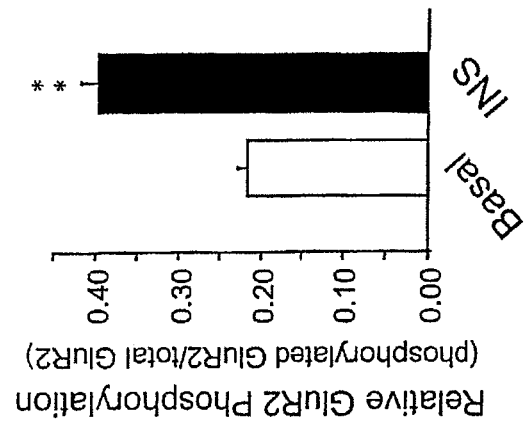
FIGS. 9A-D. Insulin stimulates tyrosine phosphorylation of GluR2 and long-lasting depression of AMPA receptor-mediated synaptic transmission. A. Tissue homogenates from hippocampal slices treated with (Basal) or without insulin (INS; 0.5 μM, 10 min) were immunoprecipitated with anti-GluR1 or GluR2 antibodies under denaturing conditions (IP: GluR1 or GluR2). Immunoprecipitates were then immunoblotted using an anti-phosphotyrosine antibody (IB: PY). The blot was sequentially stripped and re-probed with anti-GluR2 (IB: GluR2) and anti-GluR1 (IB: GluR1) antibodies. B. Densitometric quantitation expressed as the ratio of phosphorylated GluR2 to total GluR2 from three separate experiments is summarized in the histogram on the right. **p<0.01 C. EPSCs were recorded in CA1 neurons from hippocampal slices using whole-cell recordings under the voltage-clamp mode at a holding potential of −60 mV. Normalized EPSCs (EPSCt/EPSC0) are plotted from neurons recorded with pipettes containing standard intracellular solution (Control, n=7) or intracellular solution supplemented with GST-Y869KEGY873NVY876G (GluR23Y; n=5) or GST-A869KEGA873NVA876G (GluR3A; n=6). Time zero is defined as the time point at which the amplitudes of EPSCs were stabilized (typically 5-10 min after the start of whole-cell recording), and at t=10 min, insulin (0.5 μM) was applied in the bath as indicated by the horizontal black bar. D. Representative EPSCs averaged from four individual recordings before (Basal) or 10 min following application of insulin (ENS) are shown on the left.
Figure 9A:
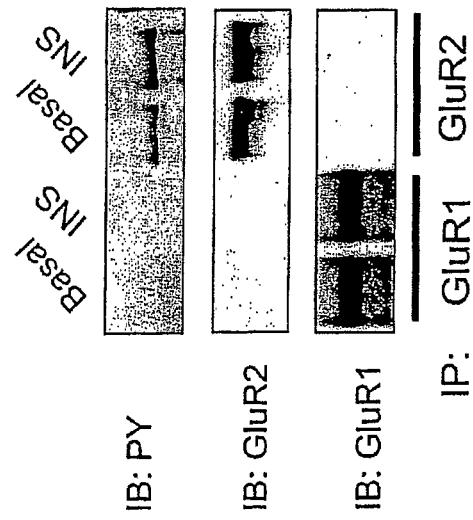

Insulin Increases Tyrosine Phosphorylation of GluR2, and Depresses AMPA Receptor-Mediated Synaptic Transmission in Hippocampal Slices We next examined whether insulin stimulation could change the level of tyrosinephosphorylation of AMPA receptors in intact hippocampus, as it does in HEK293 cells expressing GluR2 subunits (FIG. 7A-D), and whether this might be important for insulinmediated depression of AMPA receptor-mediated synaptic transmission. Hippocampal slices were treated with insulin (0.5 μM; 10 min), and GluR1 and GluR2 subunits were then immunoprecipitated under denaturing conditions (as detailed herein) and immunoblotted with an anti-phosphotyrosine antibody (FIG. 9A, B). Consistent with results from cell culture, the GluR2 subunit exhibited a clearly appreciable level of tyrosine phosphorylation under basal conditions; moreover, the level of phosphorylation was increased following insulin stimulation (FIG. 9A, B). In contrast, the tyrosine phosphorylation levels of GluR1 were barely detectable under both basal and insulin-treated conditions. These results further substantiate the tyrosine phosphorylation of GluR2 in the hippocampus and demonstrate that GluR2 tyrosine phosphorylation can be stimulated by insulin.

Figures 9C, 9D:
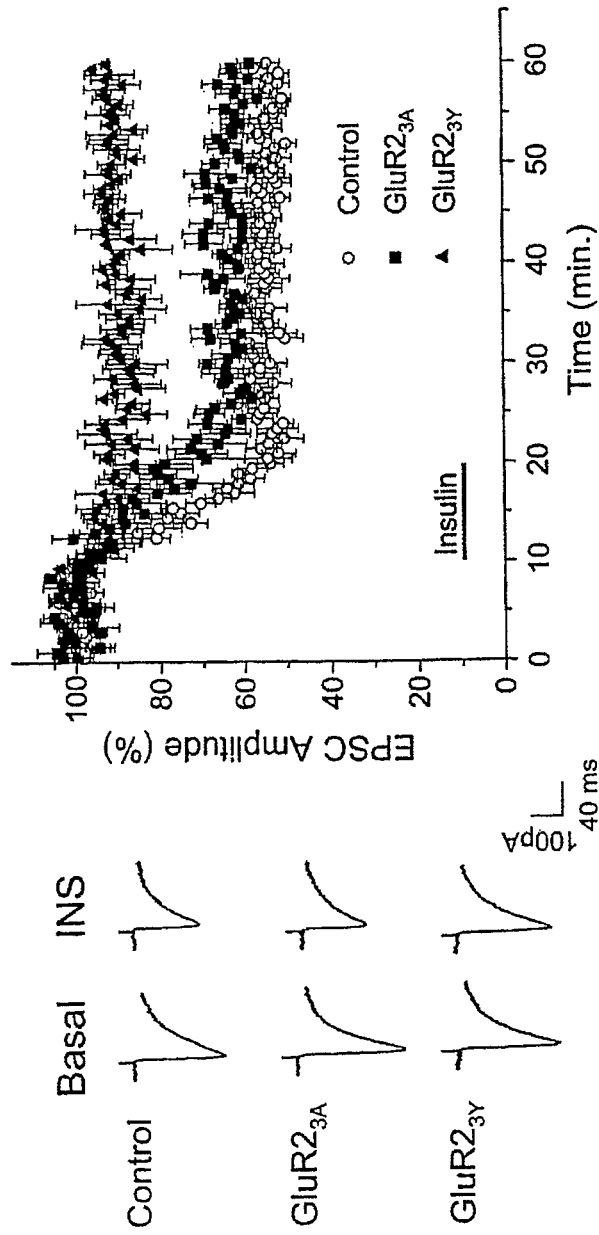

The effect of postsynaptic application of GST-GluR23Y (GST-YKEGYNVYG (SEQ ID NO. 6)), and its mutant counterpart, GST-GluR23A (GST-AKEGANVAG (SEQ ID NO. 7)), as a control, during whole-cell recordings of CA1 neurons in hippocampal slices was investigated, to determine the correlation, if any, of the insulin-stimulated tyrosine phosphorylation of AMPA receptors to persistent depression of receptor-mediated excitatory postsynaptic currents (EPSCs). As shown in FIG. 7A, the GST-GluR23Y, but not the GST-GluR23A, is a good tyrosine phosphorylation substrate. Bath application of insulin resulted in a persistent decrease in the AMPA component of EPSCs (FIG. 9C, D). The insulin-induced EPSC depression was prevented when wild-type GST-GluR23Y peptide (100 µg/ml) was included in the recording pipette, whereas the same amount of mutant peptide, GST-GluR23A, had no effect (FIG. 9C, D). Thus, the wild type tyrosine-containing peptide, but not its mutant counterpart, is sufficient to block insulin-induced persistent depression of AMPA receptor-mediated EPSCs.

Example 6

Tyrosine Residues in the GluR2 CT Mediate LTD

Figure 10A:
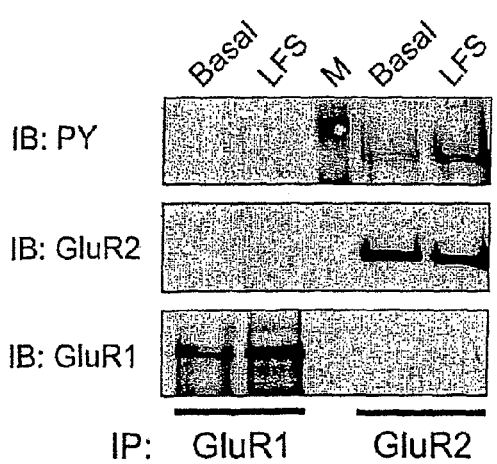
Figure 10B:
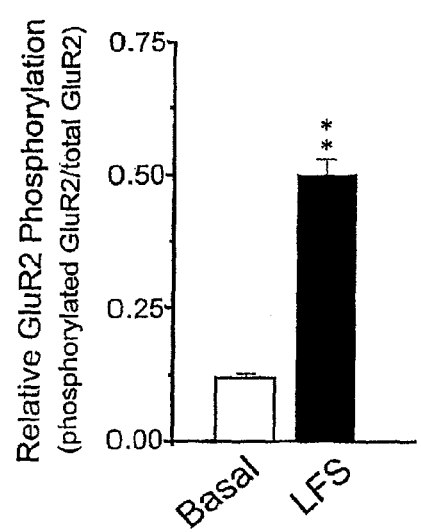

The level of GluR2 tyrosine phosphorylation was assayed following low-frequency stimulation (LFS) of hippocampal slices (1 Hz for 15 min, which reliably induces LTD under our experimental conditions), to determine whether tyrosine phosphorylation of GluR2 CT may be required for LFS-induced long term depression (LTD). Slices were homogenized in denaturing buffer 10 min after the stimulation and GluR subunits were immunoprecipitated and probed for phosphotyrosine. As shown in FIG. 10A, there was basal tyrosine phosphorylation of GluR2, but not GluR1, and LTD-inducing stimulation increased the level of tyrosine phosphorylation of GluR2 without affecting that of GluR1 (FIG. 10A). Induction of LTD by LFS was blocked by postsynaptic application of GST-GluR23Y (100 µg/ml), but not by the mutant peptide GST-GluR23A (100 µg/ml; FIG. 10B) or by GST-GluR2834-843 (FIG. 10C).

Example 7

Figure 11B:
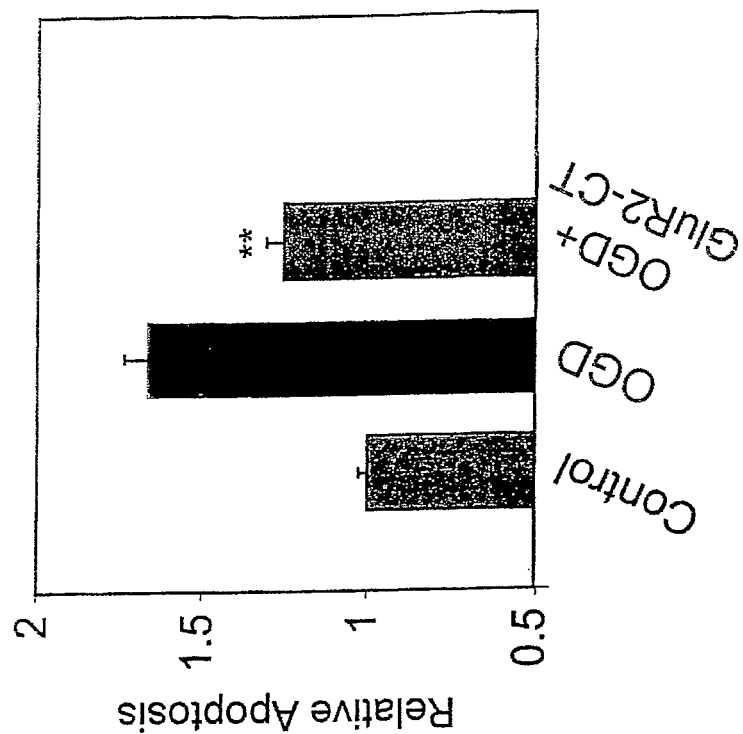
FIGS. 11A-B. GluR2 CT peptide prevents ishemia-induced AMPA receptor endocytosis and neuronal apoptosis in a neuronal culture model of stroke. A. Colorimetric (Cell-ELISA) assay shows that OGD facilitates AMPA receptor endocytosis, thereby decreasing their expression on the plasma membrane surface and pre-incubation of the GluR2-CT peptide reduced the OGD-induced decrease in cell-surface AMPA receptor expression. (n=6; *: P<0.05, Student's test, compared with Control). B. Quantitative apoptosis assay 24 hr after OGD using the Cell Death Detection ELISAplus kit (Roche, Cat#1 774 425) demonstrates that OGD produces neuronal death that is largely prevented by pre-treatment of neurons with GluR2-CT. (n=6; **: P<0.01, Student's t test, compared with OGD.
Figure 11A:
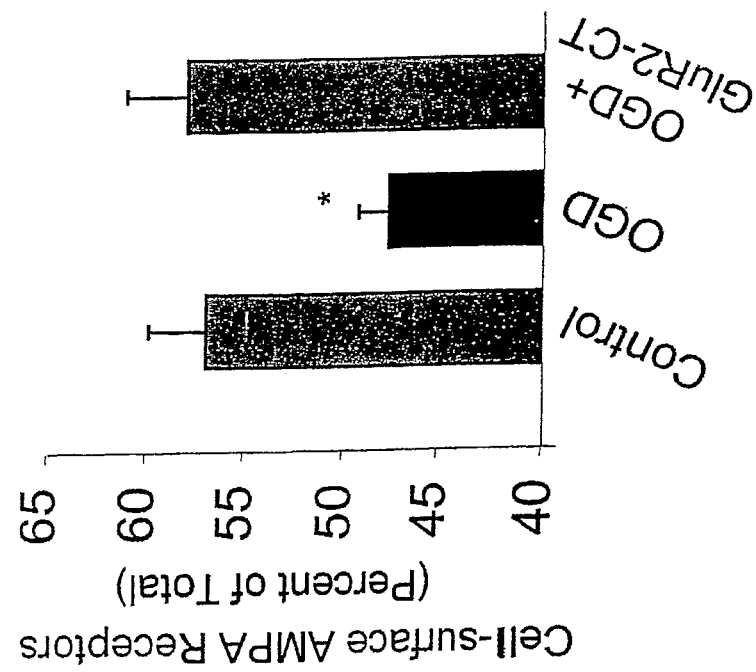

GluR2 CT Peptide Prevents Ischemia-Induced AMPA Receptor Endocytosis and Neuronal Apoptosis in a Neuronal Culture Model of Stroke Ischemia-like insult was mimicked by oxygen and glucose deprivation (OGD) for one hour in cultured cortical neurons (DIV 12-14). OGD is a well-characterized cell culture model of ischemia. GluR2CT peptide (1 mM) was delivered into neurons by mixing it with the carrier peptide PEP-1 and incubating neurons with the mixture for one hour before OGD challenge. FIG. 11A shows a colorimetric (Cell-ELISA) assay indicating that OGD facilitates AMPA receptor endocytosis, thereby decreasing their expression on the plasma membrane surface and pre-incubation of the GluR2-CT peptide reduced the OGD-induced decrease in cell-surface AMPA receptor expression. (n=6; *: P<0.05, Student's test, compared with Control). FIG. 11B is a quantitative apoptosis assay 24 hr after OGD using the Cell Death Detection ELISAplus kit (Roche, Cat#1 774 425), demonstrating that OGD produces neuronal death that is largely prevented by pre-treatment of neurons with GluR2-CT. (n=6; **: P<0.01, Student's t test, compared with OGD. Together, these results indicate that like NMDA receptor overactivation, ischemia-like insults also produces neuronal death by facilitating AMPA receptor endocytosis and as such, AMPA receptor endocytosis-blocking peptides, such as GluR2-CT peptide, can be used in stroke treatment to reduce neuronal damage.)

Example 8

Systemic Application of Tat-GlurR2$_{3Y}$ Peptide Blocks the Expression of Behavioural Sensitization to the Abusive Drug d-Amphetemine in an Animal Model of Drug Addiction Behavioral sensitization is defined as an increase in the psychomotor response to treatment with many classes of addictive drugs (i.e. amphetamine, cocaine, nicotine, heroin) and can be parsed into induction and expression phases. Behavioral sensitization is a well accepted model of neural and behavioural adaptations that are hypothesized to form the bases of addiction, specifically drug-induced changes in the mesocorticolimbic dopamine system that underlie the motivation to engage in drug-seeking behavior[60,61].

To induces behaviour sensitization to addictive drugs that lead to substance abuse, four separate groups of adult rats were given repetitive injections of damphetamine (2 mg/kg, intraperitoneally (IP)) or saline, every other day for a total of 10 injections. On days 1, 5 and 10 of the injection regimen, the rats were placed in 2-level locomotor boxes for 30 min before the amphetamine injection to habituate to the boxes, and for an additional 2 hours following the injection, and stereotypy scores (drug-induced behaviours) were assessed at 1 minute intervals every 10 minutes for the duration of the 2 hour session. After the 10$^{th}$ injection of d-amphetamine, the rats were given 21 days off, and chronically indwelling catheters were implanted into the jugular vein under anaesthesia.

In order to deliver GluR2-CT peptide into neurons in the brain following intravenous (IV) injection, the wild GluR2-CT peptide containing 3Y residues or the corresponding peptide sequence in which the 3 tyrosines were replaced with alanines was fused to the cell-membrane transduction domain of the human immunodeficiency virus-type 1 (HIV-1) Tat protein (YGRKKRRQRRR (SEQ ID NO. 5)), which is capable of crossing the blood brain barrier (BBB)[85], to obtain Tat-GluR2-3Y (YGRKKRRQRRR-YKEGYNVY-GIE (SEQ ID NO. 504)) or Tat-GluR2-3A (YGRK-KRRQRRR-AKEGANVAGIE (SEQ ID NO. 505)) peptides.

Figure 18A:
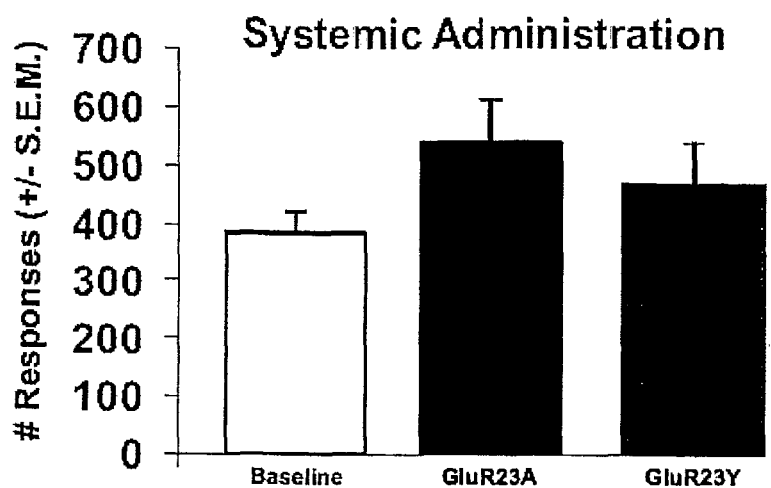
FIGS. 18 A-B. Control experiments to confirm that GluR2-3Y does not have non-specific effects on learned behaviours reinforced by food or drug-reward stimuli. These experiments also demonstrate that this interference peptide does not disrupt sensory motor or memory functions related to performance of operant behaviour on two different schedules of reinforcement. A. Rats maintained on a restricted feeding schedule were trained to lever-press for food pellets (45 mg) on a fixed-ratio 2 (FR2) schedule during 2-hour test sessions. Rats received IV injections of saline, GluR2-3A, or GluR2-3Y, in a counterbalanced order, 60 min prior to the test session. There were no significant differences in total number of responses for food reward, between the three conditions. B. Rats were first trained to self-administer d-amphetamine (0.2 mg/infusion) via a jugular catheter on an FR2 schedule of reinforcement. Once responding in the 3 hour test sessions had stabilized, the rats were then trained on a Progressive Ratio Schedule in which successively more responses were required to obtain each successive reinforcement. The ratio at which rats failed to perform the appropriate number of responses in a 1 hour period is called the beak point and this test is a sensitive measure of the unconditional reward value of a specific reward stimulus. Once stable Break point values were established, rats received IV injections of saline, GluR2-3A, or GluR2-3Y, in a counterbalanced order, 60 min prior to the test session. There were no significant differences in the Break Point measures for drug-reward, between the three conditions.
Figure 18B:
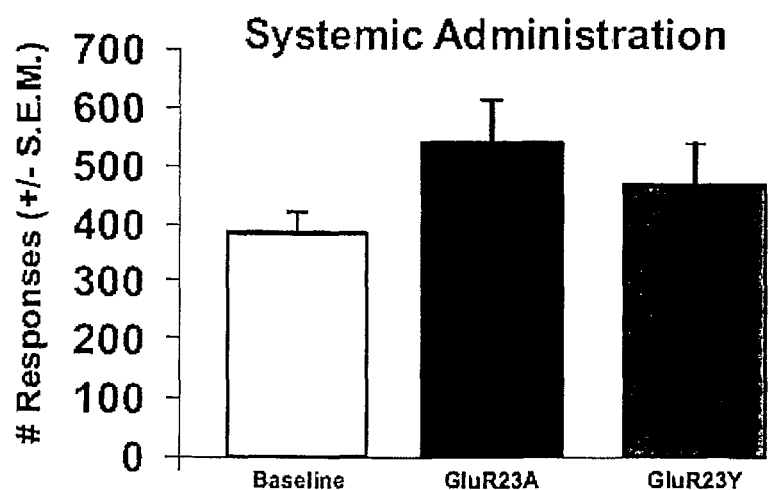

On day 21, the rats were pretreated with 1.5 nM/grTat-GluR2-3Y, or Tat-GluR2-3A or saline by either IV injection, or intracranial microinjection into the nucleus accumbens (Nac), and returned to their home cages for 60 min. The rats were then placed in the locomotor boxes (observation chambers) for 30 min and then treated with a challenge dose of d-amphetamine (2 mg/kg, IP). Stereotypy scores were then assessed as described (FIG. 12A), Points represent mean stereotypy scores (±S.E.M) for groups of rats over the 2 hour test session. Pretreatment with Tat-GluR2-3Y completely blocked the acute expression of d-amphetamine induced stereotypy, while Tat-GluR2-3A was ineffective in this regard (F(2,31)=4.22, p<0.01). FIG. 12B shows the peak effect of stereotypy, which occurred at approximately 50 minutes after d-amphetamine pretreatment, which is represented for each group. *indicates p<0.05 compared with the saline treated group. One hour intravenous pre-treatment with GluR23Y peptide, but not the control GluR23A, abolished the expression of behavioural sensitization to a challenging dose of amphetamine, without any notable side effects in rats (FIG. 12A, B). The blockade of sensitization is due to specific action in the NAc as, in a subsequent experiment, direct microinfusion of GluR23Y into the NAc, but not the VTA, mimicked IV administration, preventing the expression of the behaviour sensitization (FIG. 12C, I)). Systemic treatment with the effective wild-type peptide failed to disrupt a learned operant response for food reward delivered on an FR-2 schedule (FIG. 18A). Further evidence for the high degree of specificity of the peptide is its lack of effect on the unconditional reward effect of D-amp (FIG. 18B). These data provide the first evidence that LTD in the NAc is required for the expression of behavioural sensitization, a behavioural correlate of craving, and most significantly, that a membrane permeant short "interference peptide" that blocks LTD can prevent the expression of this behavioural sensitization without notable side effects. Thus, the ability of treatment with Tat-GluR2-3Y peptide to block the expression of behavioural sensitization is consistent with the use of such peptides in the treatment of substance abuse and addiction to classes of drug that induce behavioural sensitization.

Example 9

Treatment of Ischemic Brain Damage by Blocking AMPA Receptor Endocytosis

We investigated whether a peptide that can block AMPAR endocytosis can function as a neuroprotective agent by preventing glutamate induced neuronal apoptosis. First, in order to ensure that the peptide was able to permeate neurons, primary Wistar cortical neuron cultures were exposed to a dansyl-labeled Tat-GluR2-3Y peptide and the cells were then visualized by fluorescence microscopy. DIV 13 neurons were treated with either saline (control) or 1 μM dansyl-labeled GluR23Y peptide for 10, 20, 30, or 60 min. The peptide was able to permeate the cells in a time dependent manner. The neurons took up the dansylated Tat-GluR2-3Y in a time dependent manner with significant fluorescence visible by 10 min with a maximum at approximately 30 min.

Figure 13:
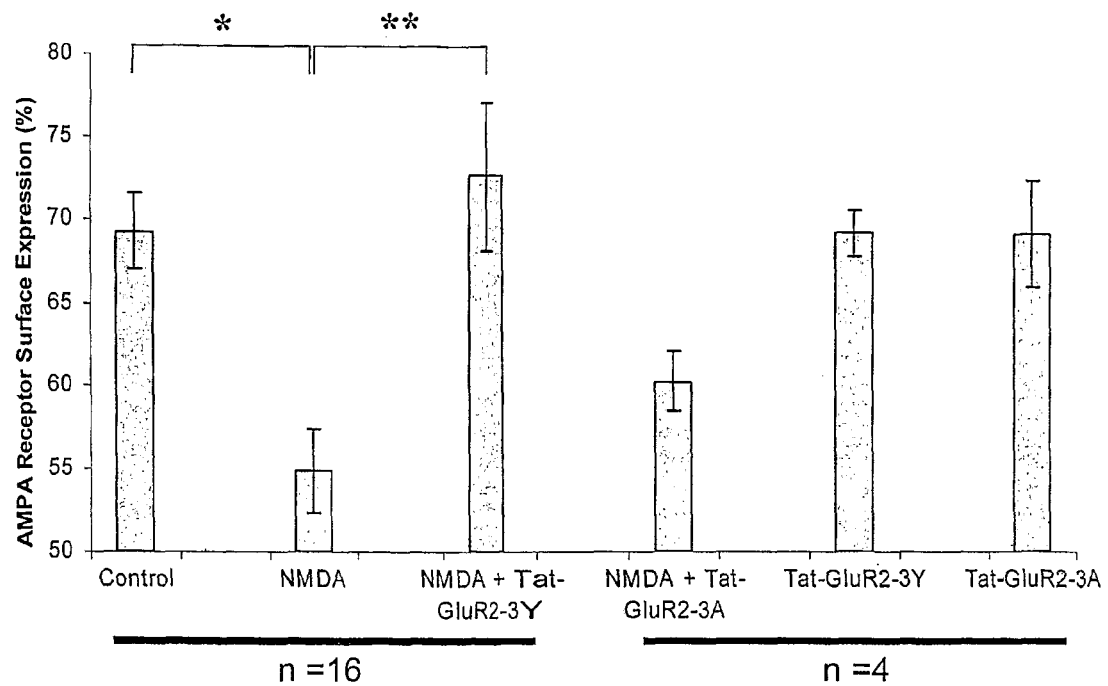
FIG. 13. Tat-GluR2-3Y blocks NMDA-induced AMPAR endocytosis. Day 12-13 in vitro Wistar cortical neurons were pretreated for 60 min with either saline or 1 µM Tat-GluR2-3Y or Tat-GluR2-3A followed by a 30 min 50 µM NMDA treatment. The percentage AMPAR expression as measured by cellular ELISA was defined as the amount of surface expression (non-permeabilized) divided by the total expression (permeabilized). Data are representative of either 1 or 4 separate experiments, each with 4 replicate measurements and are expressed as mean±SEM. *p<0.05, **p<0.05, Tukey-Kramer Test.

Once it was known that the peptide could enter cortical neurons, the ability of Tat-GluR2-3Y to block NMDA-induced AMPAR endocytosis was examined. Primary Wistar cortical neurons pretreated with or without Tat-GluR2-3Y were subjected to NMDA insult and the surface expression of AMPARs was quantified using a cellular ELISA assay. Baseline levels of AMPAR surface expression were approximately 70%, with a corresponding intracellular pool of 30%. NMDA-glycine treatment resulted in a significant decrease in AMPAR surface expression with reference to the control from 69% to 55% ($p<0.05$, Tukey-Kramer Test), that was completely blocked by pretreatment with Tat-GluR2-3Y (73% surface expression, $p<0.05$ compared to NMDA group, Tukey-Kramer Test) (FIG. 13). Furthermore, Tat-GluR2-3A, a mutated version of Tat-GluR2-3Y was unable to block NMDA-induced AMPAR endocytosis. It should also be noted that in this example, each peptide alone had no effect on AMPAR surface expression.

Figure 14:
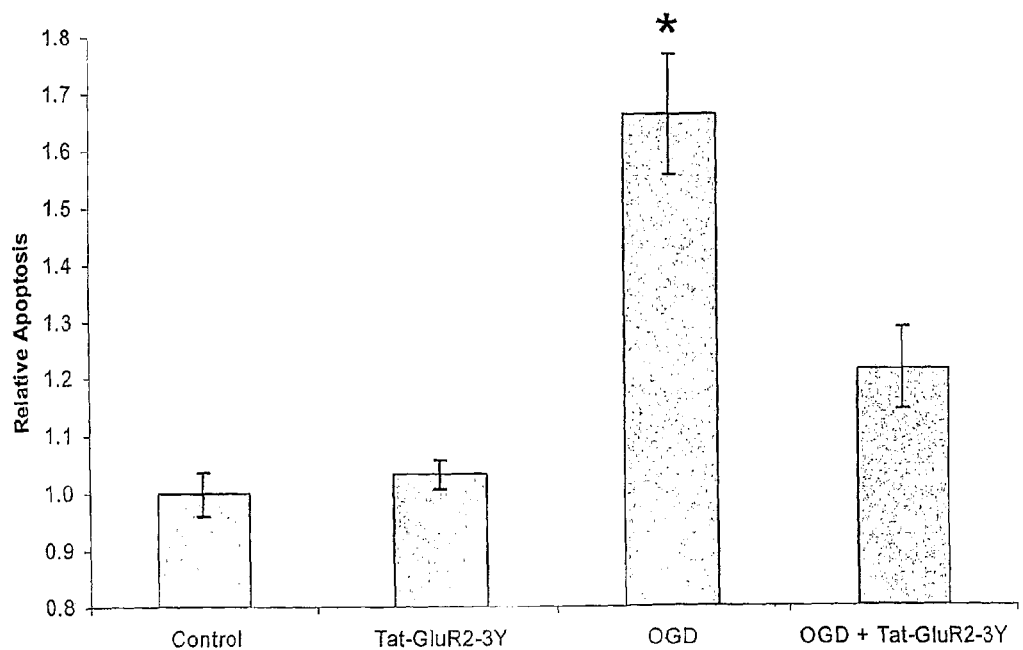
FIG. 14. Tat-GluR2-3Y attenuates neuronal apoptosis in response to oxygen and glucose deprivation. Day 12-13 in vitro Wistar cortical neurons were pretreated with either Tat-GluR2-3Y or saline for 60 min, followed by 60 min of OGD or incubation at 37° C. (control). At 24 h, apoptosis was quantified using an ELISA targeted to free nucleosomes. The data were normalized to the control and are expressed as mean±SEM of 3 repeat experiments. *OGD group was significantly different from all other groups p<0.05, Tukey-Kramer Test.

Since Tat-GluR2-3Y was able to block NMDA induced AMPAR endocytosis, the ability of the peptide to protect cultured neurons against oxygen and glucose deprivation (OGD)-induced apoptosis was investigated. DIV 12-13 neurons were pretreated with either saline or Tat-GluR2-3Y for 60 min, followed by 60 min of OGD at 37° C. or incubation at 37° C. in media (control). The amount of apoptosis was quantified using an ELISA assay targeted to free nucleosomes which are characteristic of apoptosis. OGD induced significant apoptosis compared with the control that was substantially blocked by pretreatment with Tat-GluR2-3Y ($p<0.05$) (FIG. 14).

For study of the peptide in vivo we first investigated whether the peptide could pass the blood brain barrier (BBB) and infiltrate neuronal tissue. Either dansyl-labeled Tat-GluR2-3Y or saline was administered to male C57-Black/6 mice and 40 μm coronal brain slices were cut with a cryostat and visualized with fluorescence microscopy. More specifically, two adult male C57-Black/6 mice were given an intraperitoneal injection of either 30 nmoles/g of dansyl-labeled Tat-GluR2-3Y or saline. The mice were sacrificed 2 h following injection and 40 micron coronal sections were cut with a cryostat and visualized with fluorescence microscopy. The results indicated that the dansyl-labeled peptide brain sections exhibited a greater fluorescence intensity than the control, confirming entry of the peptide into the brain, and that dansyl-labeled Tat-GluR2-3Y crosses the blood brain barrier and enters neural tissue.

In order to qualitatively describe the location and size of the infarct produced by the intraluminal suture method of MCA occlusion, 4 male Sprague Dawley rats were subjected to the procedure, sacrificed at day 3 post MCA occlusion, and 1 mm brain slices were stained with 2,3,5-triphenyltetrazolium chloride (TTC). More specifically, adult male Sprague-Dawley rats of ~300 g body weight were subjected to 60 min of MCA occlusion using an intraluminal 3-0 nylon monofilament. The rats were then sacrificed at 3 days post MCA occlusion and the brains were sliced into 1 mm sections and stained with TTC. The transient ischemia method resulted in significant infarct volume with the maximum coronal cross-sectional involvement at ~−1.5 mm with respect to the bregma. The infarct volume was reproducible with significant cortical involvement in each rat. From the TTC staining, −0.8 mm with respect to the bregma was chosen for apoptosis staining using terminal deoxyribonucleotide transferase [TdT]-mediated dUTP nick end labeling (TUNEL).

Figure 15:
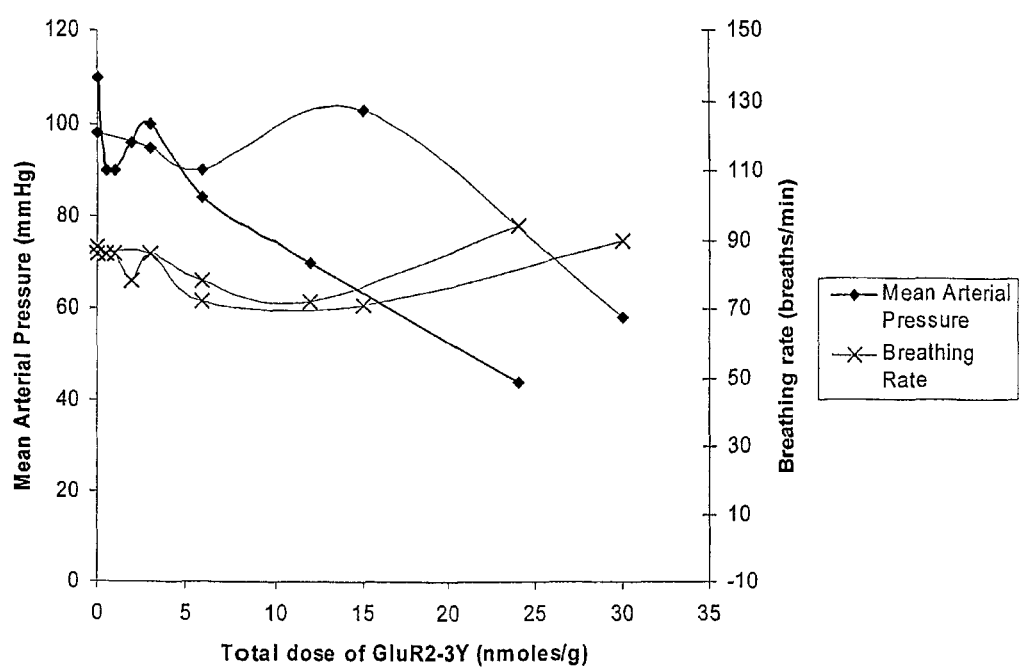
FIG. 15. Dose tolerance curve to serial doses of Tat-GluR2-3Y. Two adult male Sprague-Dawley rats were given serial doses of Tat-GluR2-3Y and the basic vital parameters were monitored. Doses of up to 6 nmoles/g evoked little response in the parameters monitored; however, higher doses resulted in a large decrease in mean arterial pressure and a concurrent increase in breathing rate. Both animals showed no sign of altered behaviour after coming out of anesthesia.

In order to determine the maximum dose that could be administered without adverse reaction, two male Sprague Dawley rats were injected with serial doses of Tat-GluR2-3Y ranging from 0.5 nmoles/g to 30 nmoles/g and basic vital parameters were monitored. It was found that the drug was tolerated up to a dose of ~12 nmoles/g after which there was a large decline in blood pressure concurrent with an increase in breathing rate (FIG. 15) and corresponding changes in $pO_2$, and $pCO_2$. Both animals were revived following the dose response curve and showed no signs of mental depression or other behavioural changes. Based on these results the dose of 3 nmoles/g was chosen for subsequent in vivo experiments. Assuming complete dispersion of the peptide in the animal, this dose corresponds roughly to a concentration of 3 μM.

Figure 16:
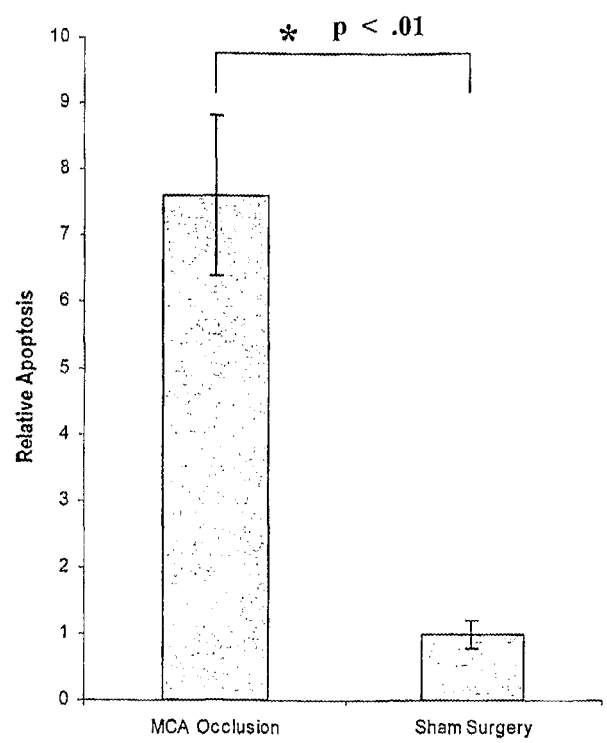
FIG. 16. Transient middle cerebral artery occlusion results in increased apoptosis. Two adult male Sprague-Dawley rats were subjected to either 90 min of MCA occlusion or surgery without MCA occlusion (sham). At 24 h, the rats were sacrificed, and 12 µm brain slices were TUNEL stained. The number of TUNEL positive nuclei was counted for 3 visual fields and are presented as mean±SEM (B). *p<0.01, Student's t-test.

As the proposed mechanism of neuroprotection for Tat-GluR2-3Y is the prevention of apoptosis, it was first necessary to demonstrate and quantify apoptosis in the model of transient focal ischemia. Two male Sprague-Dawley rats were subjected to either 90 min of MCA occlusion, or sham surgery without occlusion. Using TUNEL staining of brain slices obtained 24 h after surgery, MCA occlusion was shown to cause significant apoptosis (FIG. 16).

Figure 17A:
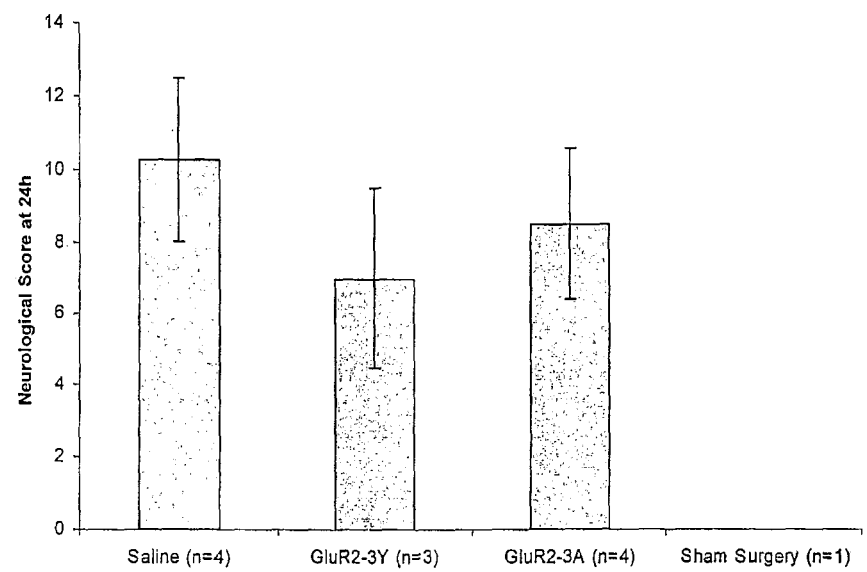
FIGS. 17A-B. The effect Tat-GluR2-3Y on apoptosis in a rat model of transient focal ischemia. Adult male Sprague-Dawley rats were pretreated for 1 h with either saline, or 3 nmol/g of Tat-GluR2-3Y or Tat-GluR2-3A and then subjected to 60 min of MCA occlusion. The rats were given a neurological exam before sacrifice at 24 h (A). 12 µm coronal brain slices were TUNEL stained and the number of TUNEL positive cells were counted for each section (B). Data are normalized to a sham surgery control and are expressed as mean values±SEM. The peptide reduced apoptosis by 55% with respect to the control.
Figure 17B:
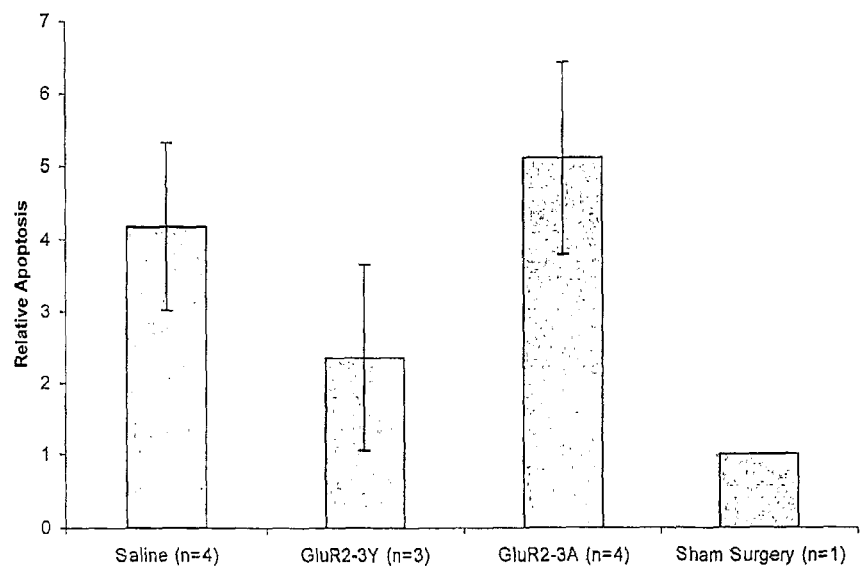

Given the evidence that Tat-GluR2-3Y pretreatment was able to block AMPAR receptor endocytosis and reduce OGD-induced apoptosis in vitro, the ability of peptide pretreatment to prevent neurological deficit and penumbral apoptosis in transient focal ischemia was investigated. 15 male Sprague-Dawley rats were pretreated with either 3 nmoles/g of Tat-GluR2-3Y or Tat-GluR2-3A or saline for 60 min, after which, the right MCA was occluded for 60 min. The rats were given a neurological examination 45 min into the MCA occlusion and at sacrifice (~24 h). No significant difference was noted in the neurological scores at 24 h (FIG. 17A) or during occlusion. Following sacrifice, 12 coronal sections were stained with TUNEL and the number of TUNEL positive cells in the cortex of the affected hemisphere was scored (FIG. 17B). Pretreatment with Tat-GluR2-3Y resulted in a ~55% decrease in apoptosis with respect to the saline control, while pretreatment with Tat-GluR2-3A resulted in a ~22% increase in apoptosis, however, due to the small sample size and high variability, these differences did not reach statistical significance. It was noted during the surgery that pretreatment with Tat-GluR2-3Y and Tat-GluR2-3A versus saline resulted in significantly lower mean arterial blood pressure (MABP) 10 min prior to MCA occlusion; p<0.05 Tukey-Kramer Test.

Example 10

Treatment of Stress-Related Disorders Using the Glu R2-CT Peptide

Stress is known to prime the induction of LTD[123] and to results in stress-related disorders such as memory impairment[124], anxiety and depression[125]. Thus, the GluR2-3Y peptide, by blocking regulated endocytosis and hence LTD, may have therapeutic effects for these stress-related disorders. As an example, we have therefore tested the effect of the peptide against stress-induced anxiety using a well-established animal anxiety model[126]. Rats (n=4) were injected with either 10 nM/g GluR2-3Y or equal volume of vehicle ACSF (IP). They were given 30 minutes in a dark room post injection. After that they were placed on an elevated platform for 30 minutes as a stressor and then placed on the elevated plus maze for 5 minutes[74]. The GluR2-3Y injected rats spent more time on the open arms than the ACSF rats. The ACSF rats spent most of their time in the corners of the closed arms or rearing to look over the walls. Thus, GluR2$_{3Y}$ peptide blocked stress induced anxiety (FIG. 19). These results strongly suggest that facilitated AMPAR endocytosis and hence the expression of LTD play an indispensable role in the expression of stress-induced behaviors and that LTD blockers such as the GluR2$_{3Y}$ peptide may be used as therapeutics to treat stress-related brain disorders, including anxiety, post-traumatic syndrome and depression.

Example 11

Prevention of Drug Addiction Relapse and Treatment of Psychotic Disorders Using GluR2-CT Peptides Relapse induced by presentation of a priming dose of drug or conditional stimuli paired previously with amphetamine or heroin infusions is a critical phase of addictive behaviour. A rat model of intravenous drug self administration is used, coupled with extinction of drug-seeking behaviour prior to tests of relapse[73]. The Tat-GluR23Y peptide, the mutated control peptide GluR23A, and vehicle is injected intravenously prior to tests of relapse. After demonstration of success in preventing relapse, a battery of behavioural control experiments are conducted to ensure that treatment with the Tat-GluR2 peptides does not produce generalized deficits in learning and memory. This protocol uses tests of recognition and spatial and temporal-order memory used routinely, along with a standard neurological test battery to ensure normal sensory and motor function (FIG. 18A-B). The effects of the GluR23Y peptide on specific tests in rats that model psychotic symptoms in humans including pre-pulse inhibition, PCP-induced hyperactivity and social interaction is also examined. As blockade of the sensitization occurs without affecting AMPAR function and basal synaptic transmission, the adverse consequences of blocking transmitter receptors often associated with other currently available anti-psychotic drugs does not occur.

REFERENCES

The following publications are incorporated herein by reference.

1. Mattson M. P., Nat. Rev. Mol. Cell Biol. 1, 120-129 (2000).
2. Graham S. H. and J. Chen, J. Cereb. Blood Flow Metab 21, 99-109 (2001).
3. Yu S. P., L. M. Canzoniero, D. W. Choi, Curr. Opin. Cell Biol. 13, 405-411 (2001).
4. Nicotera P. etc. and S. A. Lipton, J. Cereb. Blood Flow Metab 19, 583-591 (1999).
5. G. E. Hardingham, Y. Fukunaga, H. Bading, Nat. Neurosci. (2002).
6. H. Y. Man, W. Ju, G. Ahmadian, Y. T. Wang, Cell Mol. Life Sci. 57, 1526-1534 (2000).
7. R. Malinow and R. C. Malenka, Annu. Rev. Neurosci. 25, 103-126 (2002).
8. A. V. Vieira, C. Lamaze, S. L. Schmid, Science 274, 2086-2089 (1996).
9. A. Kiselev et al., Neuron 28, 139-152 (2000).
10. P. G. Alloway, L. Howard, P. J. Dolph, Neuron 28, 129-138 (2000).
11. K. L. Pierce and R. J. Lefkowitz, Nat. Rev. Neurosci. 2, 727-733 (2001).
12. S. L. Budd, L. Tenneti, T. Lishnak, S. A. Lipton, Proc. Natl. Acad. Sci. U.S.A 97, 6161-6166 (2000).
13. S. H. Hansen, K. Sandvig, B. van Deurs, J. Cell Biol. 121, 61-72 (1993).
14. H. Y. Man et al., Neuron 25, 649-662 (2000).
15. B. Marks and H. T. McMahon, Curr. Biol. 8, 740-749 (1998).
16. S. S. Okamoto et al., Proc. Natl. Acad. Sci. U.S.A 99, 3974-3979 (2002).
17. H. Dudek et al., Science 275, 661-665 (1997).
18. E. Chalecka-Franaszek and D. M. Chuang, Proc. Natl. Acad. Sci. U.S.A 96, 8745-8750 (1999).
19. P. J. Coffer, J. Jin, J. R. Woodgett, Biochem. J. 335 (Pt 1), 1-13 (1998).
20. J. W. Lin et al., Nat. Neurosci. 3, 1282-1290 (2000).
21. M. D. Ehlers, Neuron 28, 511-525 (2000).
22. E. C. Beattie et al., Nat. Neurosci. 3, 1291-1300 (2000).
23. M. C. Morris, J. Depollier, J. Mery, F. Heitz, G. Divita, Nat. Biotechnol. 19, 1173-1176 (2001).
24. C. Luscher et al., Neuron 24, 649-658 (1999).
25. Y. T. Wang and D. J. Linden, Neuron 25, 635-647 (2000).
26. Y. T. Wang and M. W. Salter, Nature 369, 233-235 (1994).
27. Benke, T. A., Luthi, A., Isaac, J. T., and Collingridge, G. L. (1998) Modulation of AMPA receptor unitary conductance by synaptic activity. Nature, 393, 793-797.
28. Bonifacino, J. S. and Dell'Angelica, E. C. (1999) Molecular bases for the recognition of tyrosine-based sorting signals. J. Cell Biol., 145, 923-926.
29. Boxall, A. R., Lancaster, B., and Garthwaite, J. (1996) Tyrosine kinase is required for long-term depression in the cerebellum. Neuron, 16, 805-813.
30. Carroll, R. C., Beattie, E. C., Xia, H., scher, C., Altschuler, Y., Nicoll, R. A., Malenka, R. C., and von Zastrow, M. (1999) Dynamin-dependent endocytosis of ionotropic glutamate receptors. Proc. Natl. Acad. Sci. U.S.A, 96, 14112-14117.
31. Chung, H. J., Xia, J., Scannevin, R. H., Zhang, X., and Huganir, R. L. (2000) Phosphorylation of the AMPA receptor subunit GluR2 differentially regulates its interaction with PDZ domain-containing proteins. J. Neurosci., 20, 7258-7267.

32. Daw, M. I., Chittajallu, R., Bortolotto, Z. A., Dev, K. K., Duprat, F., Henley, J. M., Collingridge, G. L., and Isaac, J. T. (2000) PDZ proteins interacting with C-terminal GluR2/3 are involved in a PKC-dependent regulation of AMPA receptors at hippocampal synapses. *Neuron*, 28, 873-886.
33. Derkach, V.; Barria, A., and Soderling, T. R. (1999) Ca2+/calmodulin-kinase II enhances channel conductance of alpha-amino-3-hydroxy-5-methyl-4-isoxazolepropionate type glutamate receptors. *Proc. Natl. Acad. Sci. U.S.A*, 96, 3269-3274.
34. Greengard, P., Jen, J., Nairn, A. C., and Stevens, C. F. (1991) Enhancement of the glutamate response by cAMP-dependent protein kinase in hippocampal neurons. *Science*, 253, 1135-1138.
35. Hayashi, Y., Shi, S. H., Esteban, J. A., Piccini, A., Poncer, J. C., and Malinow, R. (2000) Driving AMPA receptors into synapses by LTP and CaMKII: requirement for GluR1 and PDZ domain interaction. *Science*, 287, 2262-2267.
36. Hollmann, M. and Heinemann, S. (1994) Cloned glutamate receptors. *Annu. Rev. Neurosci.*, 17, 31-108.
37. Karoor, V., Wang, L., Wang, H. Y., and Malbon, C. C. (1998) Insulin stimulates sequestration of beta-adrenergic receptors and enhanced association of beta-adrenergic receptors with Grb2 via tyrosine 350. *J. Biol. Chem.*, 273, 33035-33041.
38. Kim, C. H., Chung, H. J., Lee, H. K., and Huganir, R. L. (2001) Interaction of the AMPA receptor subunit GluR2/3 with PDZ domains regulates hippocampal long-term depression. *Proc. Natl. Acad. Sci. U.S.A*, 98, 11725-11730.
39. Lau, L. F. and Huganir, R. L. (1995) Differential tyrosine phosphorylation of N-methyl-D-aspartate receptor subunits. *Journal of Biological Chemistry*, 270, 20036-20041.
40. Lee, S. H., Liu, L., Wang, Y. T., and Sheng, M. (2002) Clathrin adaptor AP2 and NSF interact with overlapping sites of GluR2 and play distinct roles in AMPA receptor trafficking and hippocampal LTD. *Neuron*, 36, 661-674.
41. Liang, F. and Huganir, R. L. (2001) Coupling of agonist-induced AMPA receptor internalization with receptor recycling. *J. Neurochem.*, 77, 1626-1631.
42. Lu, W., Man, H., Ju, W., Trimble, W. S., MacDonald, J. F., and Wang, Y. T. (2001) Activation of synaptic NMDA receptors induces membrane insertion of new AMPA receptors and LTP in cultured hippocampal neurons. *Neuron*, 29, 243-254.
43. Luscher, C., Nicoll, R. A., Malenka, R. C., and Muller, D. (2000) Synaptic plasticity and dynamic modulation of the postsynaptic membrane. *Nat. Neurosci.*, 3, 545-550.
44. Luthi, A., Chittajallu, R., Duprat, F., Palmer, M. J., Benke, T. A., Kidd, F. L., Henley, J. M., Isaac, J. T., and Collingridge, G. L. (1999) Hippocampal LTD expression involves a pool of AMPARs regulated by the NSF-GluR2 interaction [see comments]. *Neuron*, 24, 389-399.
45. Malinow, R., Mainen, Z. F., and Hayashi, Y. (2000) LTP mechanisms: from silence to four-lane traffic. *Curr. Opin. Neurobiol.*, 10, 352-357.
46. Matsuda, S., Launey, T., Mikawa, S., and Hirai, H. (2000) Disruption of AMPA receptor GluR2 clusters following long-term depression induction in cerebellar Purkinje neurons. *EMBO J.*, 19, 2765-2774.
47. Nishimune, A., Isaac, J. T., Molnar, E., Noel, J., Nash, S. R., Tagaya, M., Collingridge, G. L., Nakanishi, S., and Henley, J. M. (1998) NSF binding to GluR2 regulates synaptic transmission. *Neuron*, 21, 87-97.
48. Osten, P., Srivastava, S., Inman, G. J., Vilim, F. S., Khatri, L., Lee, L. M., States, B. A., Einheber, S., Milner, T. A., Hanson, P. I., and Ziff, E. B. (1998) The AMPA receptor GluR2 C terminus can mediate a reversible, ATP-dependent interaction with NSF and alpha- and beta-SNAPs. *Neuron*, 21, 99-110.
49. Passafaro, M., Piech, V., and Sheng, M. (2001) Subunit-specific temporal and spatial patterns of AMPA receptor exocytosis in hippocampal neurons. *Nat. Neurosci.*, 4, 917-926.
50. Pickard, L., Duckworth, J. K., Fitzjohn, S. M., Henley, J. M., Collingridge, G. L., and Molnar, E. (2001) Transient synaptic activation of NMDA receptors leads to the insertion of native AMPA receptors at hippocampal neuronal plasma membranes. *Neuropharmacology*, 41, 700-713.
51. Song, I., Kamboj, S., Xia, J., Dong, H., Liao, D., and Huganir, R. L. (1998) Interaction of the N-ethylmaleimide-sensitive factor with AMPA receptors. *Neuron*, 21, 393-400.
52. Stern-Bach, Y., Russo, S., Neuman, M., and Rosenmund, C. (1998) A point mutation in the glutamate binding site blocks desensitization of AMPA receptors. *Neuron*, 21, 907-918.
53. Wenthold, R. J., Petralia, R. S., Blahos, J., II, and Niedzielski, A. S. (1996) Evidence for multiple AMPA receptor complexes in hippocampal CA1/CA2 neurons. *Journal of Neuroscience*, 16, 1982-1989.
54. Xia, J., Chung, H. J., Wihler, C., Huganir, R. L., and Linden, D. J. (2000) Cerebellar long-term depression requires PKC-regulated interactions between GluR2/3 and PDZ domain-containing proteins. *Neuron*, 28, 499-510.
55. Krammer et al. (1991) "Apoptosis in the APO-1 System", Apoptosis: The Molecular Basis of Cell Death, pp. 87-99 Cold Spring Harbor Laboratory Press.
56. Harlow and Lane Antibodies; A Laboratory Manual, Cold Spring Harbor Laboratory, Cold Spring Harbor, N.Y., 1988.
57. Eisenberg et al *J. Mol. Bio.* 179:125-142, 184.
58. Sambrook, et al. Molecular Cloning: A Laboratory Manual. 2nd ed., Cold Spring Harbor Laboratory, Cold Spring Harbor Laboratory Press, Cold Spring Harbor, N.Y., 1989.
59. Ausubel et al. Current Protocols in Molecular Biology, John Wiley & Sons, 1994.
60. Berke, J. D. & Hyman, S. E. (2000). Addiction, dopamine and the molecular mechanisms of memory. *Neuron*, 25, 515-532.
61. Robinson, T. E. & Berridge, K. L. (1993). The neural basis of drug craving: an incentive-sensitization theory of addiction. *Brain Res., Brain Res. Rev.*, 18, 247-291.
62. Jarousse, N. and Kelly, R. B. (2000) Selective inhibition of adaptor complex-mediated vesiculation. Traffic 1:378-384.
63. Altschul, S. F. 1991. "Amino acid substitution matrices from an information theoretic perspective." Journal of Molecular Biology, 219: 555-665.
64. Dayhoff, M. O., Schwartz, R. M., Orcutt, B. C. 1978. "A model of evolutionary change in proteins." In "Atlas of Protein Sequence and Structure" 5(3) M. O. Dayhoff (ed.), 345-352, National Biomedical Research Foundation, Washington.
65. States, D. J., Gish, W., Altschul, S. F. 1991. "Improved Sensitivity of Nucleic Acid Database Search Using Application-Specific Scoring Matrices" Methods: A companion to Methods in Enzymology 3(1): 66-77.

66. Steven Henikoff and Jorja G. Henikoff. 1992 "Amino acid substitution matrices from protein blocks." Proc. Natl. Acad. Sci. USA. 89(biochemistry): 10915-10919.
67. M. S. Johnson and J. P. Overington. 1993. "A Structural Basis of Sequence Comparisons: An evaluation of scoring methodologies." Journal of Molecular Biology. 233: 716-738.
68. Steven Henikoff and Jorja G. Henikoff. 1993. "Performance Evaluation of Amino Acid Substitution Matrices." Proteins: Structure, Function, and Genetics. 17: 49-61.
69. Karlin, S. and Altschul, S. F. 1990. "Methods for assessing the statistical significance of molecular sequence features by using general scoring schemes" Proc. Natl. Acad. Sci. USA. 87: 2264-2268.
70. Longa E Z, Weinstein P R, Carlson S, Cummins R: Reversible middle cerebral artery occlusion without craniectomy in rats. *Stroke* 20:84-91, 1989.
71. Reglodi D, Tamas A, Lengvari I: Examination of sensorimotor performance following middle cerebral artery occlusion in rats. *Brain Res Bull* 59:459-466, 2003.
72. Kan R K, Pleva C M, Backof D R, Hamilton T A, Petrali J P: Free-floating cryostat sections for immunoelectron microscopy: Bridging the gap from light to electron microscopy. *Microsc Res Tech* 54:246-253, 2001.
73. Taepavarapruk P and AG Phillips: Neurochemical correlates of relapse to D amphetamine self-administration by rats induced by stimulation of the ventral subiculum, *Psychopharmacology,* 168:99-108, 2003.
74. Chaki S, A Nakazato, L Kennis, M Nakamura, C Mackie, M Sugiura, P Vinken, D Ashton, X Langlois, and T Steckler, Anxiolytic- and antidepressant-like profile of a new CRF1 receptor antagonist, R278995/CRA0450, European Journal of Pharmacology 485 145-158, 2004.
75. Davis S M, Lees K R, Albers G W, Diener H C, Markabi S, Karlsson G, Norris J: Selfotel in acute ischemic stroke: possible neurotoxic effects of an NMDA antagonist. *Stroke* 31:347-354, 2000.
76. Lees K R: Cerestat and other NMDA antagonists in ischemic stroke. *Neurology* 49:S66-69, 1997.
77. Sacco R L, DeRosa J T, Haley E C, Jr., Levin B, Ordronneau P, Phillips S J, Rundek T, Snipes R G, Thompson J L: Glycine antagonist in neuroprotection for patients with acute stroke: GAIN Americas: a randomized controlled trial. *Jama* 285:1719-1728, 2001.
78. Albers G W, Goldstein L B, Hall D, Lesko L M: Aptiganel hydrochloride in acute ischemic stroke: a randomized controlled trial. *Jama* 286:2673-2682, 2001.
79 Clark W M, Raps E C, Tong D C, Kelly R E: Cervene (Nalmefene) in acute ischemic stroke: final results of a phase III efficacy study. The Cervene Stroke Study Investigators. *Stroke* 31:1234-1239, 2000.
80. Diener H C, Hacke W, Hennerici M, Radberg J, Hantson L, De Keyser J: Lubeluzole in acute ischemic stroke. A double-blind, placebo-controlled phase II trial. Lubeluzole International Study Group. Stroke 27:76-81, 1996.
81. Clark W M, Wechsler L R, Sabounjian L A, Schwiderski U E: A phase III randomized efficacy trial of 2000 mg citicoline in acute ischemic stroke patients. *Neurology* 57:1595-1602, 2001.
82. Horn J, Limburg M: Calcium antagonists for ischemic stroke: a systematic review. *Stroke* 32:570-576, 2001.
83. Use of anti-ICAM-1 therapy in ischemic stroke: results of the Enlimomab Acute Stroke Trial. *Neurology* 57:1428-1434, 2001.
84. Lyden P, Shuaib A, Ng K, Levin K, Atkinson R P, Rajput A, Wechsler L, Ashwood T, Claesson L, Odergren T, Salazar-Grueso E: Clomethiazole Acute Stroke Study in ischemic stroke (CLASS-I): final results. *Stroke* 33:122-128, 2002.
85. Becker-Hapak M, McAllister S S, Dowdy S F: TAT-mediated protein transduction into mammalian cells. *Methods* 24:247-256, 2001.
86. Lau E, Bungard T J, Tsuyuki R T: Stroke prophylaxis in institutionalized elderly patients with atrial fibrillation. *J Am Geriatr Soc* 52:428-433, 2004.
87. Furlan A, Higashida R, Wechsler L, Gent M, Rowley H, Kase C, Pessin M, Ahuja A, Callahan F, Clark W M, Silver F, Rivera F: Intra-arterial prourokinase for acute ischemic stroke. The PROACT II study: a randomized controlled trial. Prolyse in Acute Cerebral Thromboembolism. *Jama* 282:2003-2011, 1999.
88. Ahmed N, Nasman P, Wahlgren N G: Effect of intravenous nimodipine on blood pressure and outcome after acute stroke. *Stroke* 31:1250-1255, 2000.
89. Osborne K A, Shigeno T, Balarsky A M, Ford I, McCulloch J, Teasdale G M, Graham DI: Quantitative assessment of early brain damage in a rat model of focal cerebral ischaemia. *J Neurol Neurosurg Psychiatry* 50:402-410, 1987.
90. Williams L S, Rotich J, Qi R, Fineberg N, Espay A, Bruno A, Fineberg S E, Tierney W R: Effects of admission hyperglycemia on mortality and costs in acute ischemic stroke. *Neurology* 59:67-71, 2002.
91. Lin B, Ginsberg M D, Busto R: Hyperglycemic exacerbation of neuronal damage following forebrain ischemia: microglial, astrocytic and endothelial alterations. *Acta Neuropathol (Berl)* 96:610-620, 1998.
92. Takano K., Carano R A, Tatlisumak T, Meiler M, Sotak C H, Kleinert H D, Fisher M: Efficacy of intra-arterial and intravenous prourokinase in an embolic stroke model evaluated by diffusion-perfusion magnetic resonance imaging. *Neurology* 50:870-875, 1998.
93. Wang Y, Lim L L, Levi C, Heller R F, Fisher J: Influence of admission body temperature on stroke mortality. *Stroke* 31:404-409, 2000.
94. Thornhill J, Corbett D: Therapeutic implications of hypothermic and hyperthermic temperature conditions in stroke patients. *Can J Physiol Pharmacol* 79:254-261, 2001.
95. Miguel-Hidalgo J J, Alvarez X A, Cacabelos R, Quack G: Neuroprotection by memantine against neurodegeneration induced by beta-amyloid(1-40). *Brain Res* 958: 210-221, 2002.
96. Doraiswamy P M: Alzheimer's disease and the glutamate NMDA receptor. *Psychopharmacol Bull* 37:41-49, 2003.
97. Cheramy A, Barbeito L, Godeheu G, Glowinski J: Riluzole inhibits the release of glutamate in the caudate nucleus of the cat in vivo. *Neurosci Lett* 147:209-212, 1992.
98. Zuddas A, Oberto G, Vaglini F, Fascetti F, Fornai F, Corsini G U: MK-801 prevents 1-methyl-4-phenyl-1,2,3, 6-tetrahydropyridine-induced parkinsonism in primates. *J Neurochem* 59:733-739, 1992.
99. Doble A: The role of excitotoxicity in neurodegenerative disease: implications for therapy. *Pharmacol Ther* 81:163-221, 1999.
100. Bensimon G, Lacomblez L, Meininger V: A controlled trial of riluzole in amyotrophic lateral sclerosis. ALS/Riluzole Study Group. *N Engl J Med* 330:585-591, 1994.
101. Berke J D, Hyman S E (2000) Addiction, dopamine and the molecular mechanisms of memory. *Neuron* 25: 515-532.

102. Everitt, B J, Dickinson A, Robbins T W (2001) The neuropsychological basis of addictive behaviour. *Brain Res Rev* 36:129-138.
103. Everitt B J, Wolf M E (2002) Psychomotor stimulant addiction: a neural systems perspective. *J Neurosci* 22(9): 3312-3320.
104. Hyman S E, Malenka R C (2001) Addiction and the brain: the neurobiology of compulsion and its persistence. *Nat Rev Neurosci* 2:695-703.
105. Koob G F, LeMoal M (1997) Drug abuse: Hedonic homeostatic dysregulation *Science* 278:52-58.
106. Koob G F, LeMoal M (2001) Drug addiction, dysregulation of reward, and allostasis. *Neuropsychopharmacology* 24:97-129.
107. Ellenbroek BA (2003), Animal models in the genomic era: possibilities and limitations with special emphasis on schizophrenia. *Behav Pharmacol* 14(5-6): 409-17.
108. Geyer M A et al (2001) Pharmacological studies of prepulse inhibition models of sensorimotor gating deficits in schizophrenia: a decade in review. *Psychopharmacology (Berl)* 156(2-3): 117-54.
109. Geyer M A, Ellenbroek B (2003) Animal behavior models of the mechanisms underlying antipsychotic atypicality. *Prog Neuropsychopharmacol Biol Psychiatry* 27(7): 1071-9.
110. Honer W G et al (2002) Abnormalities of SNARE mechanism proteins in anterior frontal cortex in severe mental illness. *Cereb Cortex* 12(4): 349-56.
111. Mimics K et al (2000), Molecular characterization of schizophrenia viewed by microarray analysis of gene expression in prefrontal cortex. *Neuron* 28(1): 53-67.
112. Thomas M J, C Beurrier, A Bonci, and RC Malenka (2001), Long-term depression in the nucleus accumbens: a neural correlate of behavioral sensitization to cocaine. *Nat. Neurosci.* 4:1217-1223.
113. Metzler M, Li B, Gan L, Georgiou J, Gutekunst C A, Wang Y, Torre E, Devon RS, Oh R, Legendre-Guillemin V, Rich M, Alvarez C, Gertsenstein M, McPherson P S, Nagy A, Wang Y T, Roder J C, Raymond L A, Hayden M R: Disruption of the endocytic protein HIP1 results in neurological deficits and decreased AMPA receptor trafficking. *Embo J* 22:3254-3266, 2003.
114. Kabouridis, P S, Biological Applications of Protein Transduction Technology *TIES* 21: 498503, 2003.
115. Yen W, Williamson J, Bertram E H, Kapur J. A comparison of three NMDA receptor antagonists in the treatment of prolonged status epilepticus. Epilepsy Res. 2004 March; 59(1):43-50.
116. Kaul M, Lipton SA. Signaling pathways to neuronal damage and apoptosis in human immunodeficiency virus type 1-associated dementia: Chemokine receptors, excitotoxicity, and beyond, J Neurovirol. 2004; 10 Suppl 1:97-101.
117. Li J, Pelletier M R, Perez Velazquez J L, Carlen P L. Reduced cortical synaptic plasticity and GluR1 expression associated with fragile X mental retardation protein deficiency. Mol Cell Neurosci. 2002 February; 19(2):138-51.
118. Johnston M V, Jean O H, Pevsner J, Blue M E, Naidu S. Neurobiology of Rett syndrome: a genetic disorder of synapse development. Brain Dev. 2001 December; 23 Suppl 1:S206-13.
119. Arundine M, Tymianski M. Molecular mechanisms of calcium-dependent neurodegeneration in excitotoxicity. Cell Calcium. 2003 October-November; 34(4-5):325-37.
120. Corona J C, Tapia R. AMPA receptor activation, but not the accumulation of endogenous extracellular glutamate, induces paralysis and motor neuron death in rat spinal cord in vivo. J Neurochem. 2004 May; 89(4):988-97.
121. Rolling, F. Recombinant AAV-mediated gene transfer to the retina: gene therapy perspectives, Gene Ther. 2004 October; 11 Suppl 1:S26-32.
122. Geoffroy M C, Epstein A L, Toublanc E, Moullier P, Salvetti A. Herpes Simplex Virus Type 1 ICP0 Protein Mediates Activation of Adeno-Associated Virus Type 2 rep Gene Expression from a Latent Integrated Form, J Virol. 2004 October; 78(20):10977-86.
123. X. Lin et al, Behavioural stress facilitates the induction of long-term depression in the hippocampus, Nature 387: 497, 1997.
124. F. J. Dominique et al, Stress and glucocorticoids impair retrieval of long-term spatial memory, Nature 394:787, 1998.
125. Ordyan N E, Pivina S G. Characteristics of the behavior and stress-reactivity of the hypophyseal-adrenal system in prenatally stressed rats. Neurosci Behav Physiol. 2004 July; 34(6):569-74.
126. Pellow S, Chopin P, File S E, Briley M. Validation of open:closed arm entries in an elevated plus-maze as a measure of anxiety in the rat. J Neurosci Methods. 1985 August; 14(3):149-67.

Other Embodiments

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Accession numbers, as used herein, refer to Accession numbers from multiple databases, including GenBank, the European Molecular Biology Laboratory (EMBL), the DNA Database of Japan (DDBJ), or the Genome Sequence Data Base (GSDB), for nucleotide sequences, and including the Protein Information Resource (PIR), SWISSPROT, Protein Research Foundation (PRF), and Protein Data Bank (PDB) (sequences from solved structures), as well as from translations from annotated coding regions from nucleotide sequences in GenBank, EMBL, DDBJ, or RefSeq, for polypeptide sequences. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A method of treating neurological damage or dysfunction in a subject in need thereof, the method comprising administering an effective amount of an inhibitor of alpha-Amino-3-hydroxy-5-methyl-4-isoxazoleproprionic acid (AMPA) receptor endocytosis to the subject, wherein: the inhibitor consists of the amino acid sequence YREGYNVYGIE (SEQ ID NO:1), YKEGYNVYGIE (SEQ ID NO:2); or YGRKKRRQRRRYKEGYNVYGIE (SEQ ID NO:504).

2. The method of claim 1, wherein the inhibitor is administered in an amount effective to inhibit regulated AMPA receptor endocytosis.

3. The method of claim 1, wherein the neurological damage comprises cerebral ischemia.

4. The method of claim 1, wherein the neurological damage occurs as a result of excessive activation of NMDA receptors or due to changes in AMPA receptor endocytosis.

5. The method of claim 1, wherein the neurological damage or dysfunction occurs as a result of at least one of a disorder selected from the group consisting of stress, anxiety, depression, hypoglycemia, cardiac arrest, epilepsy, cerebral ischemia, brain trauma, Alzheimer's disease, Parkinson's disease, Huntington's disease; neuropathic pain; amyotrophic lateral sclerosis (ALS); Hutchinson Gilford syndrome; diabetes; ataxia; mental retardation; dementias, disorders associated with smoking or obesity, high blood pressure, disorders associated with defects or dysfunction in learning or memory, psychiatric disorders, autism, schizophrenia, fragile X syndrome, and disorders associated with substance abuse or addiction to a drug.

6. The method of claim 5, wherein the drug is selected from at least one of the group consisting of nicotine, alcohol, opiates, heroin, codeine, morphine pethidine, methadone, marijuana, phenyclidene, psychostimulants, amphetamines, cocaine, barbiturates, pentobarbitone, quinalbarbitone, benzodiazepines, temazepam, diazepam and flunitrazepam.

* * * * *